US008597660B2

(12) United States Patent (10) Patent No.: US 8,597,660 B2
Pant et al. (45) Date of Patent: Dec. 3, 2013

(54) THERAPEUTIC APPROACH TO NEURODEGENERATIVE DISORDERS USING A TFP5-PEPTIDE

(75) Inventors: Harish C. Pant, Rockville, MD (US); Ya-li Zheng, Yinchuan (CN); Niranjana D. Amin, Clarksburg, MD (US); Philip Grant, Washington, DC (US); Parvathi Rudrabhatla, Washington, DC (US); Varsha Shukla, Rockville, MD (US); Sashi Kesavapany, Singapore (SG)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/249,003

(22) Filed: Sep. 29, 2011

(65) Prior Publication Data

US 2012/0115790 A1 May 10, 2012

Related U.S. Application Data

(60) Provisional application No. 61/387,839, filed on Sep. 29, 2010.

(51) Int. Cl.
*A61K 39/385* (2006.01)
*A61K 39/00* (2006.01)
*A61K 38/00* (2006.01)
*A01N 37/18* (2006.01)

(52) U.S. Cl.
USPC .................. 424/193.1; 424/198.1; 530/350; 514/17.8; 514/17.5; 514/21.3

(58) Field of Classification Search
None
See application file for complete search history.

(56) References Cited

U.S. PATENT DOCUMENTS 6,693,166 B1 * 2/2004 Wang et al. ................... 530/324

FOREIGN PATENT DOCUMENTS

WO      WO 00/21550      4/2000

OTHER PUBLICATIONS

Amin et al., "Cyclin-Dependent Kinase 5 Phosphorylation of Human Septin SEPT5 (hCDCrel-1) Modulates Exocytosis," *The Journal of Neuroscience*, 28(14): 3631-3643, 2008.
Cardone et al., "Evaluation of the interaction of cyclin dependent kinase 5 with activator p25 and with p25-derived inhibitor CIP," *J. Comput. Biol.*, 17(5): 707-721, 2010.
Kanungo et al., "Cloning and characterization of zebrafish (*Danio rerio*) Cyclin-dependent kinase 5," *Neurosci Lett.*, 412(3): 233-238, 2007.

Kanungo et al., "Cyclin-dependent kinase 5 influences Rohon-Beard neuron survival in zebrafish," *Journal of Neurochemistry*, 99: 251-259, 2006.
Kesavapany et al., "Inhibition of Pin1 Reduces Glutamate-induced Perikaryal Accumulation of Phosphorylated Neurofilament-H in Neurons," *Molecular Biology*, 18: 3645-3655, 2007.
Kesavapany et al., "Neuronal Nuclear Organization Is Controlled by Cyclin-Dependent Kinase 5 Phosphorylation of Ras Guanine Nucleotide Releasing Factor-1," *Neurosignals*, 15: 157-173, 2006.
Kesavapany et al., "Peptides derived from Cdk5 activator p35, specifically inhibit deregulated activity of Cdk5," *Biotechnol.*, 2: 978-987, 2007.
Kino et al., "Cyclin-Dependent Kinase 5 Differentially Regulates the Transcriptional Activity of the Glucocorticoid Receptor through Phosphorylation: Clinical Implications for the Nervous System Response to Glucocorticoids and Stress," *Molecular Endocrinology*, 21(7): 1552-1568, 2007.
Pant, "The Cyclin Dependent Kinase 5 Inhibitor (Cip & P5) Reduces a 1-42 and P25/Cdk5-Mediated Tau Hyperphosphorylation and Apoptosis in Neurons," *Neurodegenerative Disease*, 4(suppl. 1): 279, Abstract 840, 2007.
Pareek et al., "Cyclin-dependent kinase 5 modulates nociceptive signaling through direct phosphorylation of transient receptor potential vanilloid 1,"*PNAS*, 104(2): 660-665, 2007.
Sihag et al., "Role of Phosphorylation on the Structural Dynamics and Function of Types III and IV Intermediate Filaments," *Exp Cell Res.*, 313(10): 2098-2109, 2007.
Zheng et al., "A 24-Residue Peptide (p5), Derived from p35, the Cdk5 Neuronal Activator, Specifically Inhibits Cdk5-p25 Hyperactivity and Tau Hyperphosphorylation," *The Journal of Biological Chemistry*, 285(44): 34202-34212, 2010.
Zheng et al., "A Cdk5 inhibitory peptide reduces tau hyperphosphorylation and apoptosis in neuron," *The EMBO Journal*, 24: 209-220, 2005.
Zheng et al., "A peptide derived from cyclin-dependent kinase activator (p35) specifically inhibits Cdk5 activity and phosphorylation of tau protein in transfected cells," *Eur J. Biochem.*, 269: 4427-4434, 2002.
Zheng et al., "Cdk5 Modulation of Mitogen-activated Protein Kinase Signaling Regulates Neuronal Survival," *Molecular Biology*, 18: 404-413, 2007.
Amin et al., "Cyclin-dependent kinase 5 (cdk5) activation requires interaction with three domains of p35", *J. Neurosci. Res.* 67: 354-362, 2002.
Kanungo et al., "Targeting Cdk5 activity in neuronal degeneration and regeneration," *Cell Mol. Neurobiol.*, 29(8): 1073-1080, 2009.
Kesavapany et al., "Cyclin-dependent kinase 5 in neurofilament function and regulation," *Neuorosignals*, 12(4-5): 252-264, 2003.
Kesavapany et al., "Neuronal cyclin-dependent kinase 5: role in nervous system function and its specific inhibition by the Cdk5 inhibitory peptide,"*Biochim. Biophys. Acta.*, 11:1697(1-2): 143-153, 2004.

* cited by examiner

*Primary Examiner* — Olga N Chernyshev
(74) *Attorney, Agent, or Firm* — Klarquist Sparkman, LLP

(57) ABSTRACT

Disclosed herein are isolated peptides, pharmaceutical compositions and methods for use of such for treating subjects with a neurodegenerative disease, such as Alzheimer's. In an example, an isolated polypeptide includes a cyclin dependent kinase 5 (Cdk5) inhibitory domain that has at least 95% sequence identity to the amino acid sequence set forth as SEQ ID NO: 1, wherein the Cdk5 inhibitory domain is linked to a protein transduction domain. Methods of reducing or inhibiting one or more symptoms associated with a neurodegenerative disease by administering a therapeutically effective amount of a pharmaceutical composition including one or more disclosed peptides are also provided.

18 Claims, 21 Drawing Sheets

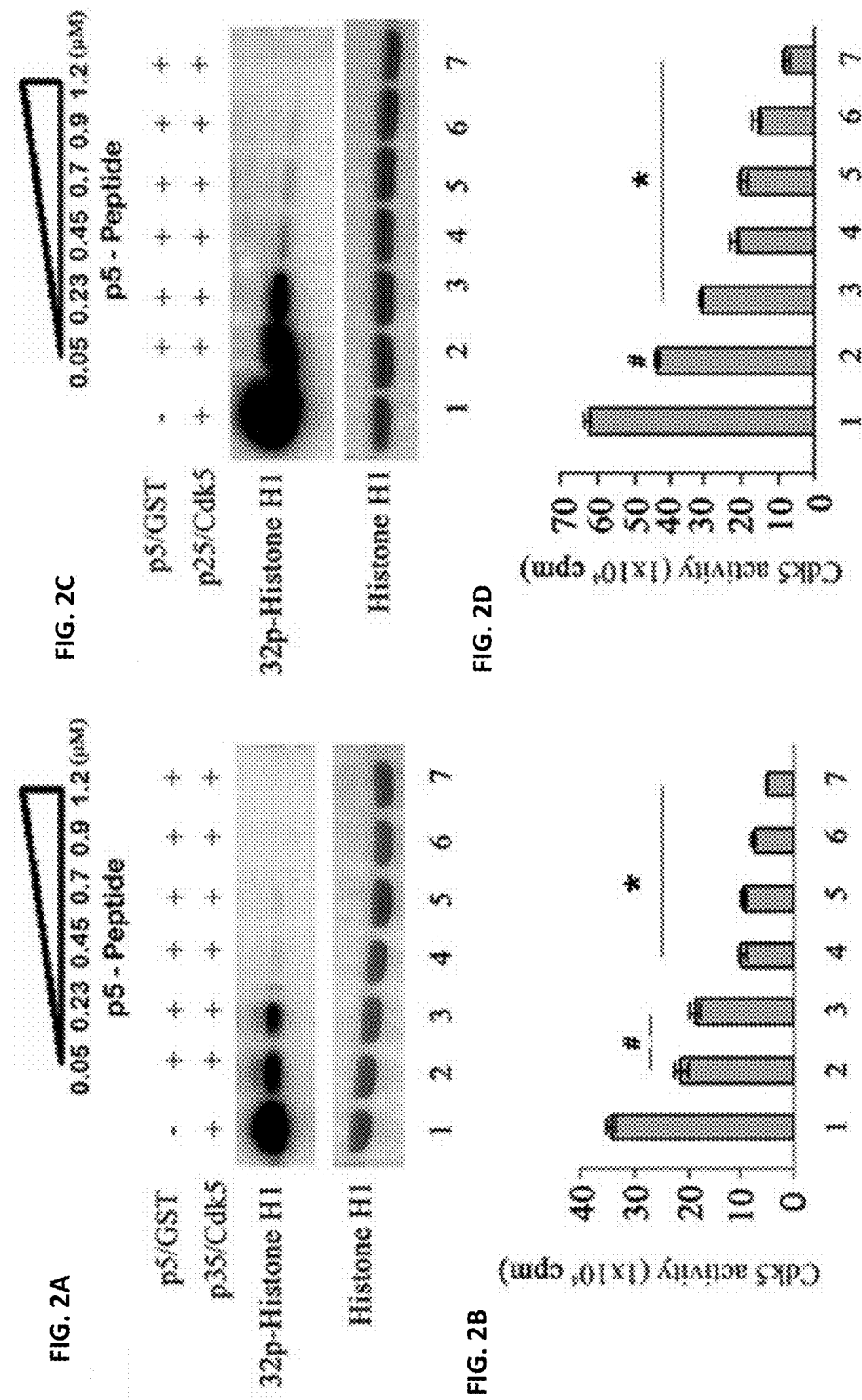

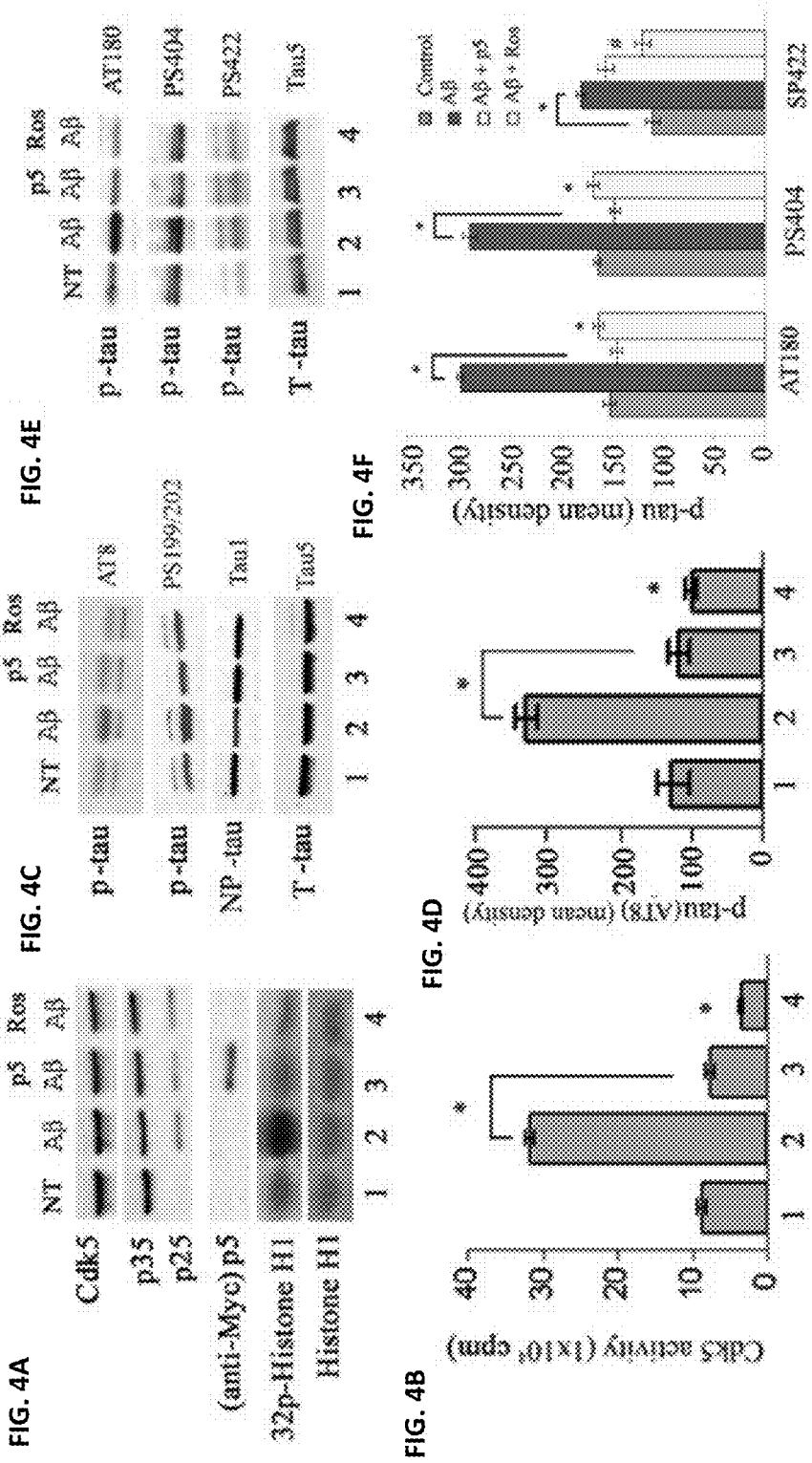

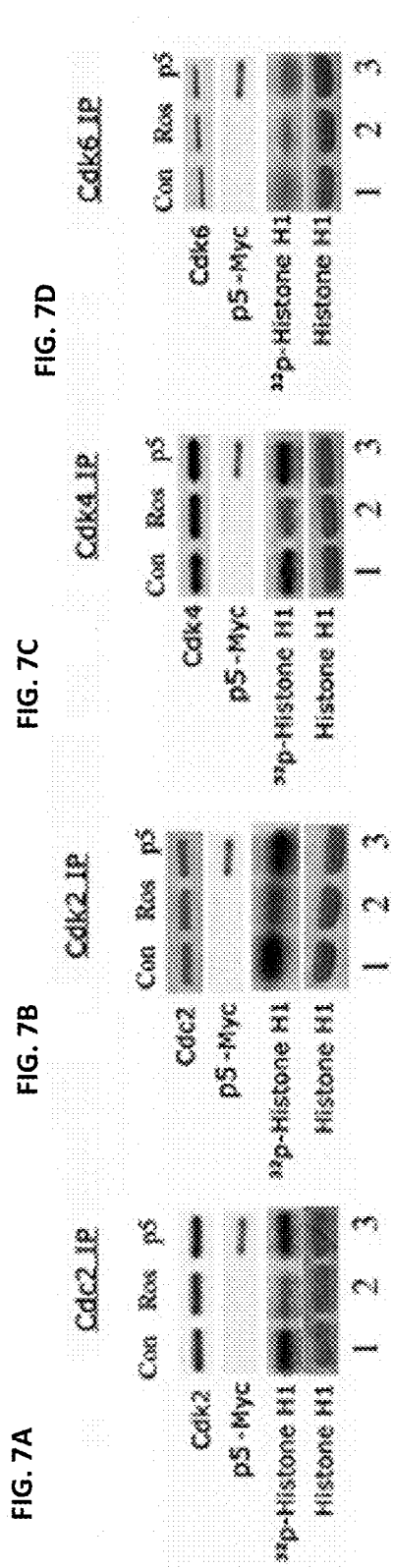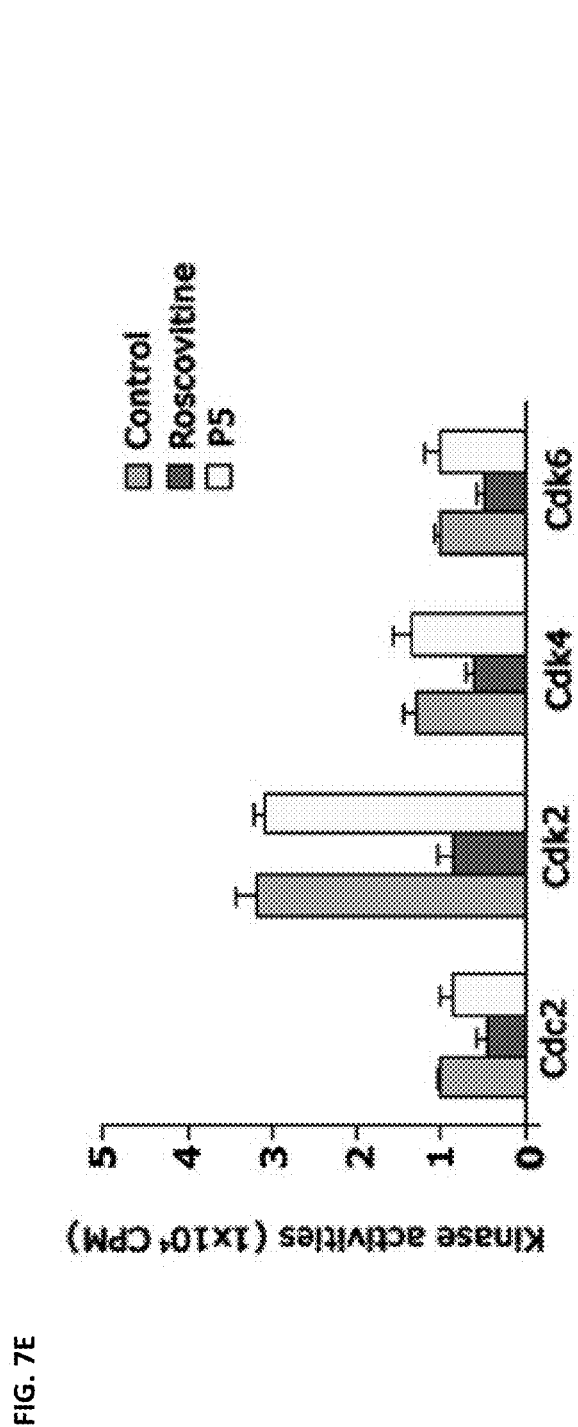
FIG. 7A
FIG. 7B
FIG. 7C
FIG. 7D
FIG. 7E

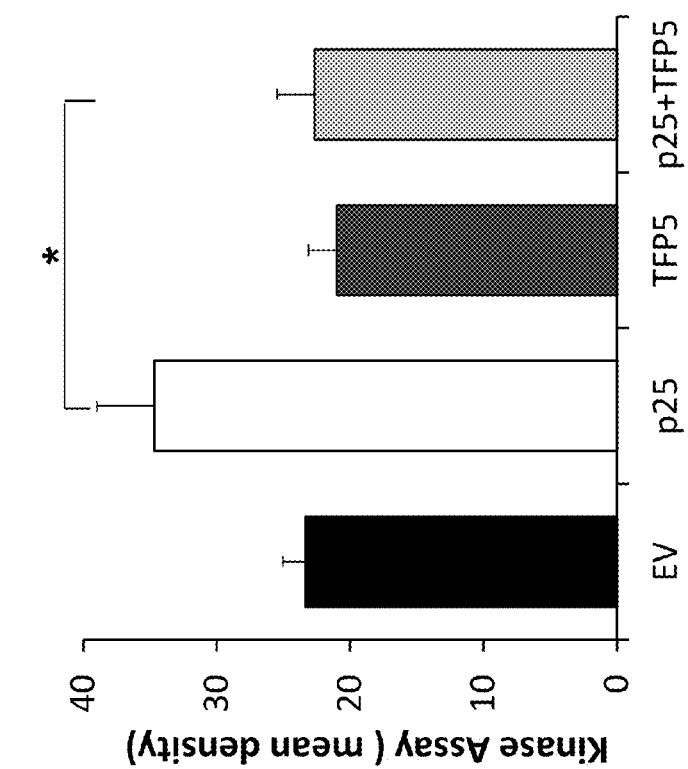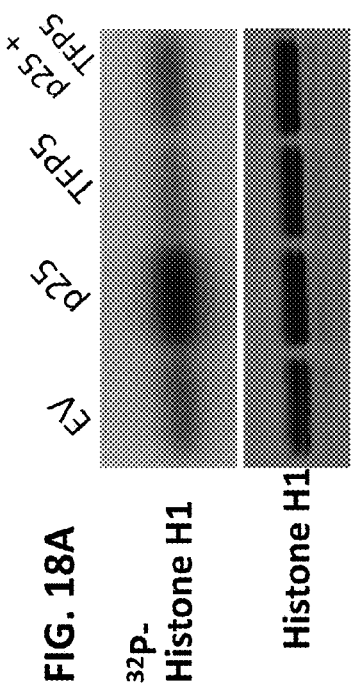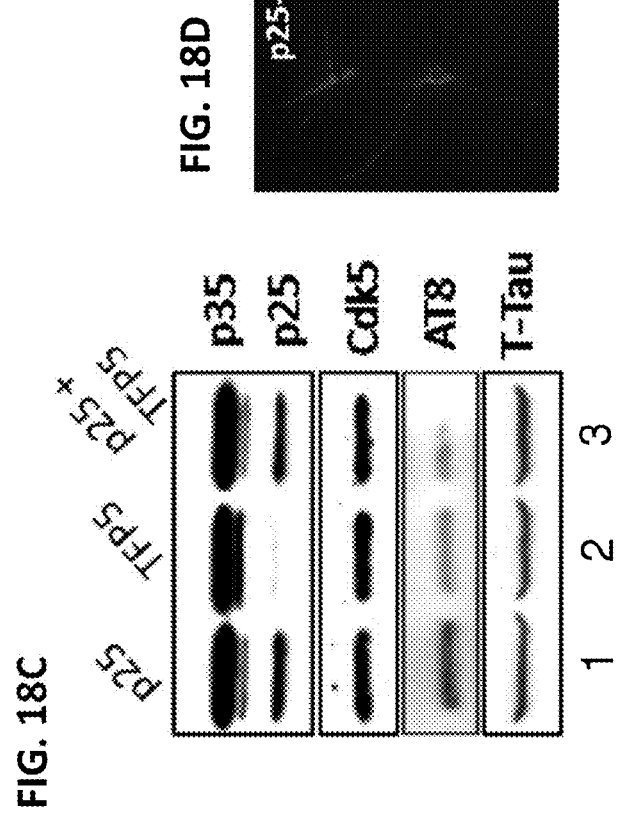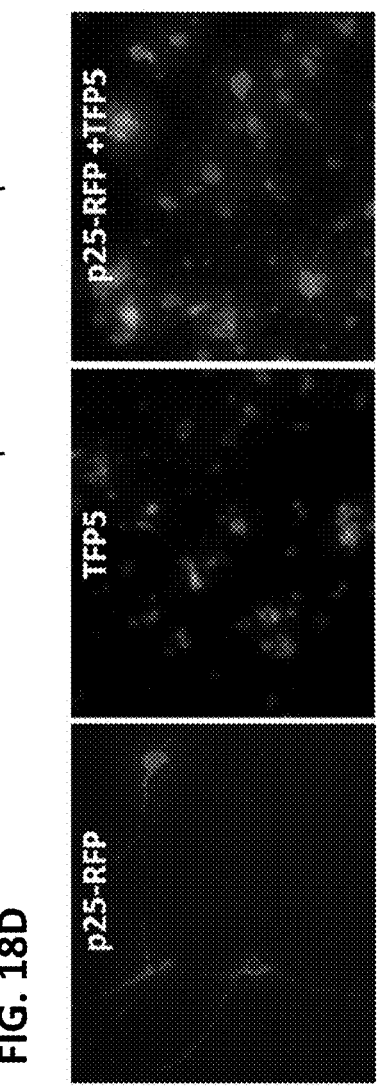
FIG. 18A
FIG. 18B
FIG. 18C
FIG. 18D

SEQUENCE LISTING

<160> NUMBER OF SEQ ID NOS: 17

<210> SEQ ID NO 1
<211> LENGTH: 24
<212> TYPE: PRT
<213> ORGANISM: Homo sapiens

<400> SEQUENCE: 1

Lys Glu Ala Phe Trp Asp Arg Cys Leu Ser Val Ile Asn Leu Met Ser
1               5                   10                  15

Ser Lys Met Leu Gln Ile Asn Ala
            20

<210> SEQ ID NO 2
<211> LENGTH: 35
<212> TYPE: PRT
<213> ORGANISM: Artificial Sequence
<220> FEATURE:
<223> OTHER INFORMATION: homo sapiens and human immunodeficiency virus
      fusion peptide

<400> SEQUENCE: 2

Lys Glu Ala Phe Trp Asp Arg Cys Leu Ser Val Ile Asn Leu Met Ser
1               5                   10                  15

Ser Lys Met Leu Gln Ile Asn Ala Tyr Ala Arg Ala Ala Arg Arg Ala
            20                  25                  30

Ala Arg Arg
        35

<210> SEQ ID NO 3
<211> LENGTH: 11
<212> TYPE: PRT
<213> ORGANISM: Human immunodeficiency virus

<400> SEQUENCE: 3

Tyr Gly Arg Lys Lys Arg Arg Gln Arg Arg Arg
1               5                   10

<210> SEQ ID NO 4
<211> LENGTH: 11
<212> TYPE: PRT
<213> ORGANISM: Human immunodeficiency virus

<400> SEQUENCE: 4

Tyr Ala Arg Ala Ala Arg Arg Ala Ala Arg Arg
1               5                   10

<210> SEQ ID NO 5
<211> LENGTH: 9
<212> TYPE: PRT
<213> ORGANISM: Human immunodeficiency virus

<400> SEQUENCE: 5

Arg Lys Lys Arg Arg Gln Arg Arg Arg
1               5

<210> SEQ ID NO 6
<211> LENGTH: 9
<212> TYPE: PRT
<213> ORGANISM: Human immunodeficiency virus

<400> SEQUENCE: 6

Lys Lys Lys Lys Lys Lys Lys Lys Lys

-continued

```
1               5

<210> SEQ ID NO 7
<211> LENGTH: 9
<212> TYPE: PRT
<213> ORGANISM: Human immunodeficiency virus

<400> SEQUENCE: 7

Arg Arg Arg Arg Arg Arg Arg Arg Arg
1               5

<210> SEQ ID NO 8
<211> LENGTH: 32
<212> TYPE: DNA
<213> ORGANISM: Artificial Sequence
<220> FEATURE:
<223> OTHER INFORMATION: synthetic oligonucleotide primer

<400> SEQUENCE: 8
tttgcggccg ccatgggcac ggtgctgtcc ct                              32

<210> SEQ ID NO 9
<211> LENGTH: 29
<212> TYPE: DNA
<213> ORGANISM: Artificial Sequence
<220> FEATURE:
<223> OTHER INFORMATION: synthetic oligonucleotide primer

<400> SEQUENCE: 9
tttgatatct taccgatcca ggcctagga                                  29

<210> SEQ ID NO 10
<211> LENGTH: 35
<212> TYPE: DNA
<213> ORGANISM: Artificial Sequence
<220> FEATURE:
<223> OTHER INFORMATION: synthetic oligonucleotide primer

<400> SEQUENCE: 10
tttgcggccg ccatggccca gcccccaccg gccca                           35

<210> SEQ ID NO 11
<211> LENGTH: 35
<212> TYPE: DNA
<213> ORGANISM: Artificial Sequence
<220> FEATURE:
<223> OTHER INFORMATION: synthetic oligonucleotide primer

<400> SEQUENCE: 11
tttgcggccg ccatgcagaa atacgagaaa ctgga                           35

<210> SEQ ID NO 12
<211> LENGTH: 29
<212> TYPE: DNA
<213> ORGANISM: Artificial Sequence
<220> FEATURE:
<223> OTHER INFORMATION: synthetic oligonucleotide primer

<400> SEQUENCE: 12
tttgatatct tagggcggac agaagtcgg                                  29

<210> SEQ ID NO 13
<211> LENGTH: 31
<212> TYPE: DNA
<213> ORGANISM: Artificial Sequence
<220> FEATURE:
<223> OTHER INFORMATION: synthetic oligonucleotide primer
```

<400> SEQUENCE: 13
tttgcggccg ccatggcatc aatgcagaag c                                      31

<210> SEQ ID NO 14
<211> LENGTH: 43
<212> TYPE: DNA
<213> ORGANISM: Artificial Sequence
<220> FEATURE:
<223> OTHER INFORMATION: synthetic oligonucleotide primer

<400> SEQUENCE: 14
tgatctcaga ggaggacctg atgaaggagg cctttttggga ccg                        43

<210> SEQ ID NO 15
<211> LENGTH: 34
<212> TYPE: DNA
<213> ORGANISM: Artificial Sequence
<220> FEATURE:
<223> OTHER INFORMATION: synthetic oligonucleotide primer

<400> SEQUENCE: 15
tttgatatct taggcattta tctgcagcat cttt                                    34

<210> SEQ ID NO 16
<211> LENGTH: 307
<212> TYPE: PRT
<213> ORGANISM: Homo sapiens

<400> SEQUENCE: 16

Met Gly Thr Val Leu Ser Leu Ser Pro Ser Tyr Arg Lys Ala Thr Leu
1               5                   10                  15

Phe Glu Asp Gly Ala Ala Thr Val Gly His Tyr Thr Ala Val Gln Asn
            20                  25                  30

Ser Lys Asn Ala Lys Asp Lys Asn Leu Lys Arg His Ser Ile Ile Ser
        35                  40                  45

Val Leu Pro Trp Lys Arg Ile Val Ala Val Ser Ala Lys Lys Lys Asn
    50                  55                  60

Ser Lys Lys Val Gln Pro Asn Ser Ser Tyr Gln Asn Asn Ile Thr His
65                  70                  75                  80

Leu Asn Asn Glu Asn Leu Lys Lys Ser Leu Ser Cys Ala Asn Leu Ser
                85                  90                  95

Thr Phe Ala Gln Pro Pro Ala Gln Pro Ala Pro Pro Ala Ser
            100                 105                 110

Gln Leu Ser Gly Ser Gln Thr Gly Gly Ser Ser Ser Val Lys Lys Ala
        115                 120                 125

Pro His Pro Ala Val Thr Ser Ala Gly Thr Pro Lys Arg Val Ile Val
    130                 135                 140

Gln Ala Ser Thr Ser Glu Leu Leu Arg Cys Leu Gly Glu Phe Leu Cys
145                 150                 155                 160

Arg Arg Cys Tyr Arg Leu Lys His Leu Ser Pro Thr Asp Pro Val Leu
                165                 170                 175

Trp Leu Arg Ser Val Asp Arg Ser Leu Leu Leu Gln Gly Trp Gln Asp
            180                 185                 190

Gln Gly Phe Ile Thr Pro Ala Asn Val Val Phe Leu Tyr Met Leu Cys
        195                 200                 205

Arg Asp Val Ile Ser Ser Glu Val Gly Ser Asp His Glu Leu Gln Ala
    210                 215                 220

Val Leu Leu Thr Cys Leu Tyr Leu Ser Tyr Ser Tyr Met Gly Asn Glu

-continued

```
                225                 230                 235                 240

Ile Ser Tyr Pro Leu Lys Pro Phe Leu Val Glu Ser Cys Lys Glu Ala
                245                 250                 255

Phe Trp Asp Arg Cys Leu Ser Val Ile Asn Leu Met Ser Ser Lys Met
                260                 265                 270

Leu Gln Ile Asn Ala Asp Pro His Tyr Phe Thr Gln Val Phe Ser Asp
            275                 280                 285

Leu Lys Asn Glu Ser Gly Gln Glu Asp Lys Lys Arg Leu Leu Leu Gly
        290                 295                 300

Leu Asp Arg
305

<210> SEQ ID NO 17
<211> LENGTH: 38
<212> TYPE: PRT
<213> ORGANISM: Artificial Sequence
<220> FEATURE:
<223> OTHER INFORMATION: synthetic peptide

<400> SEQUENCE: 17

Gly Gly Gly Lys Glu Ala Phe Trp Asp Arg Cys Leu Ser Val Ile Asn
1               5                   10                  15

Leu Met Ser Ser Lys Met Leu Gln Ile Asn Ala Tyr Ala Arg Ala Ala
                20                  25                  30

Arg Arg Ala Ala Arg Arg
                35
```

THERAPEUTIC APPROACH TO NEURODEGENERATIVE DISORDERS USING A TFP5-PEPTIDE

CROSS REFERENCE TO RELATED APPLICATION

This application claims the benefit of U.S. Provisional Application No. 61/387,839, filed Sep. 29, 2010, which is incorporated herein by reference.

FIELD OF THE DISCLOSURE

This disclosure relates to the field of neurodegenerative diseases, specifically to cyclin dependent kinase 5 (Cdk5) inhibitory peptides and their use in the treatment of neurodegenerative diseases, such as Alzheimer's disease, amyotrophic lateral sclerosis and Parkinson's disease.

INCORPORATION-BY-REFERENCE OF MATERIAL SUBMITTED AS AN ASCII TEXT FILE

A Sequence Listing is submitted herewith as an ASCII compliant text file named "Replacement Sequence Listing.txt", created on Jan. 18, 2012, and having a size of 6.61 kilobytes, as permitted under 37 CFR 1.821(c). The material in the aforementioned file is hereby incorporated by reference in its entirety.

BACKGROUND

Neurodegenerative disorders leading to dementia, such as Alzheimer's disease (AD), are chronic, long term processes resulting from an accumulation of various lesions and insults. Among the latter are oxidative stress, inflammation, hormonal deficits, abnormal cholesterol metabolism and excitotoxic stress. Such defects result in synaptic function deficits, neuronal death and dementia. The hallmark pathologies of neurodegenerative diseases (such as AD, amyotrophic lateral sclerosis (ALS) and Parkinson's disease (PD)) are brain lesions containing aberrantly phosphorylated cytoskeletal proteins, the accumulation of which leads to cell death. In particular, the extracellular aggregation of amyloid peptides and the intracellular hyperphosphorylation of tau and neurofilament proteins at specific epitopes are pathological hallmarks of AD, ALS and Parkinson's disease PD. Often neurodegeneration begins long before any symptoms are manifested. As such, diagnosis of a neurodegenerative disease tends to occur after the patient has already suffered the majority of the neural damage. Moreover, few therapies are available for the treatment of most neurodegenerative diseases even once the disease has been identified.

SUMMARY OF THE DISCLOSURE

Disclosed herein is a therapeutic approach to neurodegenerative disorders (such as AD, ALS and PD) using one or more peptides, derived from the Cdk5 activator P35, which specifically inhibits the deregulated activity of Cdk5 responsible for neuronal pathology, thereby rescuing the cortical neuron abnormal phenotypes in vitro and in vivo. As such, provided herein are isolated peptides including a Cdk5 inhibitory domain that has at least 95% sequence identity to the amino acid sequence set forth as SEQ ID NO: 1, wherein the Cdk5 inhibitory domain is linked to a protein transduction domain (PTD), such as a trans-activator of transcription (TAT) domain with at least 95% sequence identity to the amino acid sequence set forth as one of SEQ ID NO: 3, 4, 5, 6 or 7. Also disclosed are pharmaceutical compositions comprising a therapeutically effective amount of one or more of the disclosed polypeptides in a pharmaceutically acceptable carrier. Methods of using such polypeptides and pharmaceutical compositions are provided. For example, methods for preventing or reducing a neurodegenerative disorder are disclosed. These methods include administering a composition comprising one or more of the isolated polypeptides or pharmaceutical compositions at a therapeutically effective concentration to inhibit one or more symptoms associated with the neurodegenerative disorder, thereby preventing or reducing the neurodegenerative disorder. Also provided are methods for modulating Cdk5 activity, comprising contacting a cell (such as a neuronal cell) with a therapeutically effective amount of one or more disclosed polypeptides or pharmaceutical compositions, wherein the pharmaceutical composition modulates the activity of Cdk5 in the treated cell relative to Cdk5 activity in an untreated cell, thereby reducing or inhibiting at least one symptom of a Cdk5-mediated neurodegenerative disease. Additionally, kits are disclosed for reducing or inhibiting one or more symptoms associated with a neurodegenerative disease, comprising one or more disclosed polypeptides or pharmaceutical compositions and one or more protease or proteasome inhibitors. In some examples, the neurodegenerative disease is AD, PD, ALS or a combination thereof.

The foregoing and other features of the disclosure will become more apparent from the following detailed description of a several embodiments which proceeds with reference to the accompanying figures.

BRIEF DESCRIPTION OF THE FIGURES

FIGS. 2A-2D illustrate that P5 equally inhibits both Cdk5/P25 and Cdk5/P35 activities in vitro. Activated Cdk5/P35 and Cdk5/P25 were used in a comparative test tube assay of the inhibitory effect of P5 with histone H1 as the substrate. P5 as P5-GST was added at a range of concentrations from 0.05 to 1.2 µM. After SDS PAGE, autoradiographs were prepared as shown in FIGS. 2A and 2C and pad assay scintillation counts quantified from three separate experiments as summarized in the bar graphs (FIGS. 2B and 2D). Note that initially, the Cdk5/P25 activity is twice that of the Cdk5/P35 activity. The levels of inhibition, however, are almost similar although it might appear from the autoradiograms that the Cdk5/P35 activity is more sensitive since it seems completely inhibited at 0.45 µM whereas Cdk5/P25 activity is evident at least to 0.9 µM in the sample shown. This is due to the initially higher activity of the Cdk5/P25 complex. The quantitative data (FIGS. 2B and 2D), however, show that P5 equally inhibits each Cdk5 complex in a dose-dependent manner when compared to lanes 1 in FIGS. 2B and 2D, respectively; at 0.05 µM (lane 2) P5 peptide inhibits 36% of Cdk5/P35 activity and approximately 33% of Cdk5/P25 activity, while 0.7 µM (lane 5) inhibits both complexes approximately 70%, and finally at 1.2 μM (lane 6) both are inhibited approximately 90% (*p<0.01, # p<0.05).

FIG. 3B is a series of digital images illustrating the expression level of cells infected with P25 (a), P35 (b), Cdk5 (c), and P5 (d) adenovirus genes. FIG. 3C illustrates Cdk5 activity observed in Cdk5 immunoprecipitates from lysates of these infected cells (from FIG. 3A) using histone H1 as a substrate. The top panel is the autoradiograph and the bottom panel shows the corresponding Coomassie-stained histone H1 bands. FIG. 3D is a histogram showing quantitative scintillation count data in counts per minute (cpm) from corresponding pad assays of kinase activities from the same lysates. Data represent means±SE of three separate studies. (*p<0.01)

FIGS. 4A-4F illustrate that Abeta amyloid (Aβ)-mediated Cdk5 deregulated phosphorylation of tau is inhibited by P5 in cortical neurons. Seven days in culture (DIC) cortical neurons from E-18 rat brain were infected with P5 (MycP5) and treated with 10 μM Aβ1-42 for six hours, lysed and prepared for Cdk5 immunoprecipitation, Western blot analysis and kinase assays. FIG. 4A is a digital image of a Western blot showing the formation of P25 from P35 as a result of the stress induced by Aβ, (lanes 2-4)) accompanied by a significant increase in histone phosphorylation (compare lane 2 with lane 1). In the presence of P5, however, the activity is decreased by 70% to control levels although P25 is still present (compare lane 3 with lane 2). Neurons treated with 20 μM roscovitine show almost complete inhibition (lane 4). FIG. 4B is a bar graph of the scintillation count results of three separate pad assay studies of the above lysates (plotted as means±SE). FIG. 4C is a digital image of Western blot analyses of these same Aβ-treated cells infected with and without P5 exhibit Aβ induced tau phosphorylation, at PHF (paired helical filament) tau sites, Ser-202, Thr-205 and Ser199 as detected by AT8 antibody (Porzig et al., *Biochem Biophys Res Comm* 358:644-649, 2007; compare lanes 1 and 2). Cells infected with P5, however, show baseline levels of tau phosphorylation comparable to that produced by roscovitine (lanes 3 and 4) indicating P5 rescue from Aβ-induced tau hyperphosphorylation. Another tau antibody specific for sites Ser199/Ser 202 is also shown confirming the above result. Tau 1 recognizes nonphosphorylated tau whereas tau 5 identifies total tau, phosphorylated as well as non-phosphorylated. FIG. 4D is a histogram of optical density data of phosphorylation by AT8 prepared from three separate experiments. FIG. 4E is a digital image of a Westerns blots of similarly treated lysates immunoreacted with PHF antibodies AT180 (pThr-231), pSer404, and antibody pSer422. Comparison of lanes 1 and 2 shows significantly elevated Aβ-induced phosphorylation at sites Thr 231, Ser404, with lower levels at Ser422. Addition of P5 reduces phosphorylation at Thr 231 and Ser404 with only a modest affect on Ser 422 (compare lanes 2 and 3). These studies show that several other phosphorylated tau sites were rescued by P5. FIG. 4F is a bar graph including data from three separate studies (*p<0.01, # p<0.05).

FIG. 5B is a bar graph of the data provided in FIG. 5A showing virtually all P5 transfected cells were protected from Aβ-induced apoptosis. The percentage of GFP and TUNEL-expressing neurons was determined by counting at least 100 DAPI staining nuclei in each of five fields. Data from three studies are shown. FIG. 5C is a digital of a Western blot. Cortical neurons infected with or without P5 were treated with Aβ for six hours, lysed and prepared for Western blots using caspase 3 and cleaved caspase-3 antibody expression as a measure of apoptosis. Cells infected with P5 show a marked reduction in cleaved caspase 3 expression compared to Aβ treated cells without P5 (compare lanes 2 and 3) (panel 2) to a level comparable to the effect of roscovitine, lane 4. The uncleaved caspase 3 is lower in Aβ-induced cells (panel 1, lane 2), while higher in cells treated with P5 or roscovitine. FIG. 5D is a bar graph from three studies expressed in a bar graph as means±SE (*p<0.01).

FIG. 6B is a line graph showing Cdk5/P25 activities induced by Aβ were inhibited by P5 in a dose-dependent manner with virtually most of the inhibition (90%) exhibited at 0.05 μM, the lowest concentration. Data represent means±SE from three studies (*p<0.01).

FIGS. 7A-7E show that P5 does not inhibit the activity of cell cycle Cdks. To study the effect of P5 on cycling cells, a group of proliferating HEK293 cells was infected with P5-myc, the second were infected with empty vector (EV) as control and third infected with EV but treated with 20 μM roscovitine. Cell lysates from each group were immunoprecipitated with specific antibodies to Cdc2, Cdk2, Ckd4, and Cdk6 respectively. The IPs were used for Western blotting and kinase assays with histone H1 as substrate. The expression of P5-Myc, the specific kinases as seen in blots (panels 1 and 2), and the phosphorylating activities (presented as radio-autographs, panel 3) are shown in FIGS. 7A-7D. The scintillation count data (means±SE) from three pad assay studies in each case are quantified in the bar graphs shown in FIG. 7E. Roscovitine inhibits approximately 50% of endogenous Cdk activity (compare lanes 2 with 1), whereas P5 has virtually no effect, as evident from the bar graph (FIG. 7E) (comparing lanes 3 with 1).

FIG. 8A is a digital image of radioautographs showing the phosphorylating activities at different concentrations of P5 (lanes 1-6) and 20 µM roscovitine (positive control, lane 7) for each Cdk. Except for roscovitine, activities in the presence of P5 are relatively unaffected. FIG. 8B is a bar graph summarizing scintillation count data from three experiments (means±SE) of histone H1 phosphorylation. Note that only roscovitine had a significant effect on Cdk endogenous activities (approx. 50%, compare lane 7 with lane 1) whereas P5, even at the highest concentration of 1.8 µM, exhibits virtually no inhibition. (*p<0.01)

FIGS. 11A and 11B show the hyperactivation of Cdk5 upon P25 infection is reduced by TFP5 treatment. FIG. 11C illustrates the localization of TFP5 and P25 with FITC- (fluorescein isothiocyanate) and GFP- (green fluorescent protein) labeling, respectively.

FIGS. 12B and 12D are a higher magnification (40×) of FIGS. 12A and 12C (10×), respectively, showing nuclear staining with DAPI. Scale bar=5 µm.

FIG. 13A is a digital image illustrating Cdk5 immunoprecipitated using Cdk5 antibody from the respective lysates and then subjected to in vitro kinase assay using histone H1 as a substrate. FIG. 13B is a bar graph illustrating mean optical density measurements of phosphor-histone ($^{32}$P-histone H1) autoradiograph shown in FIG. 13A. Each data column represents the mean±SEM of three separate studies.

FIGS. 18A-18D illustrate that hyperactivation of Cdk5 induced by p25 is inhibited by TFP5 treatment without affecting endogenous Cdk5/p35 in cortical neurons. As shown in FIG. 18A, kinase assays were performed on day 7 in culture on lysates of rat cortical neurons after transfection with either empty vector (EV) or p25 for 48 hours. Cells were treated with 0.05 µM TFP5, 2 hours post transfection (FIG. 18A). Quantitation of kinase activities shows significant reduction in Cdk5 activity in p25 transfected cells when treated with TFP5 but endogenous Cdk5/p35 activity was unaffected. Data represent mean of three independent experiments; SEM (*p≤0.05; FIG. 18B). Western blot analysis on the lysate of cortical neurons was performed after transfection with and without p25-RFP (red fluorescent protein) using various antibodies (FIG. 18C). No p25 is observed in non-transfected cortical neurons (lane 2). Phospho-tau levels were elevated in p25 transfected to non-p25 transfected neuronal lysates. After TFP5 treatment; the phospho-tau level was reduced to that of non-transfected cells (compare lane 1, 2, and 3). Total tau antibody was used as a marker for equal loading. FIG. 18D is a digital image illustrating the localization of TFP5 and p25 with FITC and Red Fluorescent Protein (RFP), respectively, in cortical neurons.

SEQUENCE LISTING

Figure 1A:
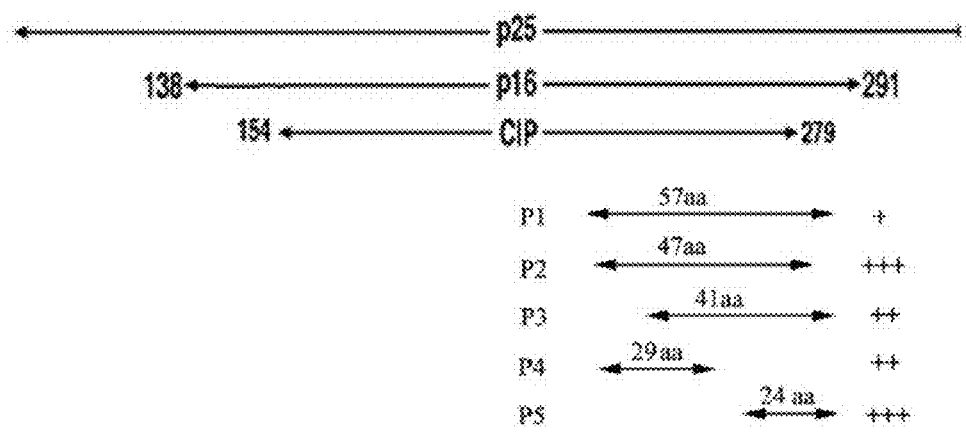
FIG. 1A is a schematic diagram of P25 truncated peptides showing the CIP peptide from which five short peptides (P1-P5) were derived. P5 was the shortest and most effective inhibitor of Cdk5/P25 in an in vitro assay with histone H1 as substrate.

The nucleic and amino acid sequences listed herein and/or in the associated Sequence Listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The disclosed sequences include the following:

SEQ ID NO: 1 is the amino acid sequence for P5.
SEQ ID NO: 2 is the amino acid sequence for P5 linked to a PTD amino acid sequence.
SEQ ID NOs: 3-7 are amino acid sequences for exemplary TAT amino acid sequence.
SEQ ID NOs: 8-15 are nucleic acid sequences for synthetic oligonucleotide primers.
SEQ ID NO: 16 is the amino acid sequence for human P35.
SEQ ID NO: 17 is the amino acid sequence for P5 linked to three glycine residues on the P5 amino terminal end and a TAT amino acid sequence on the P5 carboxy terminal end.

DETAILED DESCRIPTION OF SEVERAL EMBODIMENTS

I. Overview of Several Embodiments

Neurodegenerative diseases such as Alzheimer's disease (AD), amyotrophic lateral sclerosis (ALS) and Parkinson's disease (PD) are characterized by brain lesions containing aberrantly phosphorylated cytoskeletal proteins, the accumulation of which leads to cell death. In particular, the extracellular aggregation of amyloid peptides and the intracellular hyperphosphorylation of tau and neurofilament proteins at specific epitopes are pathological hallmarks of these diseases.

The activity of Cdk5, a multifunctional serine/threonine kinase, plays a role in neuronal development and synaptic activity; it sustains neurite outgrowth, neuronal migration, cortical lamination and survival. Its activity depends on the binding of its neuron specific, cyclin-related activators, P35 and P39. Cdk5 has also been implicated as a player in learning and memory. Normally, Cdk5 activity is tightly regulated, but under conditions of neuronal stress it is deregulated leading to hyperactivity, neuronal pathology and cell death. Accordingly, Cdk5 may be involved in certain neurodegenerative disorders such as AD. A model of Cdk5's role in neurodegeneration suggests that a stress induced influx of calcium ions into neurons activates calpain, a $Ca^{2+}$-activated protease, which cleaves P35 into P25 and a P10 fragment. P25, in turn, forms a more stable Cdk5/P25 hyperactive complex, that hyperphosphorylates tau and induces cell death. Indeed, increased levels of P25 and Cdk5 activity have been reported in AD brains. That P25 may be toxic comes from studies of cortical neurons treated with Abeta amyloid (Aβ), a key marker of AD pathology, where P35 is converted to P25 accompanied by activated Cdk5, tau hyperphosphorylation and apoptosis. Expression of the Cdk5/P25 complex seems to be primarily responsible for the tau pathology and suggests that a therapeutic approach directed specifically at this target might prove successful. For most of these studies, however, the focus has been on aminothiazol compounds resembling roscovitine, a kinase inhibitor that competes with the ATP binding site in Cdk5 and other kinases. These drugs do not act specifically on Cdk5/P25, but also inhibit Cdk5/P35 and other Cdks essential for normal development and function. This could be responsible for serious secondary side effects and thereby compromise any therapeutic value.

The therapeutic approach disclosed herein, however, is based on studies identifying a peptide (referred to as CIP) having 125 amino acid (aa) residues of P35 that inhibited Cdk5/P25 activity and rescued cortical neurons from Aβ-induced apoptosis without affecting Cdk5/P35 activity. For a therapy to be effective, however, it must be small enough to pass the blood-brain barrier (BBB). To address this problem, a smaller peptide derived from CIP with equivalent specificity is disclosed herein. Based on an analysis of Cdk5/P25 structure and molecular dynamics, several smaller peptides were produced and tested. A 24 residue peptide, called P5, has been identified which effectively inhibited Cdk5/P25 activity in cortical neurons without affecting endogenous Cdk5/P35, or other Cdks. The small size of the P5 peptide and its specificity of Cdk5 inhibition suggests its use as a therapeutic agent to treat a neurodegenerative disease, such as AD, ALS, PD, or a combination thereof.

Disclosed herein is the discovery that peptides (for example, TFP5) including at least a portion of P35 (such as P5, SEQ ID NO: 1) and a protein transduction domain (PTD) (such as a TAT protein transduction domain, such as provided by SEQ ID NOs: 3-7) can specifically inhibit deregulated activity of Cdk5 responsible for neuronal pathology and rescue the cortical neuron abnormal phenotype, both in vitro and in vivo. In particular, TFP5 treatment of rat cortical neurons reduced hyperactivation of Cdk5 induced by P25. Following intraperitoneal (i.p.) injection, TFP5 was capable of crossing the BBB and localizing within the brain. Treatment with TFP5 was found to rescue memory deficits in 5XFAD mice (amyloid precursor protein/presenilin 1 (APP/PS1) double transgenic AD mouse model), which exhibit elevated expression of p25, Cdk5 activity, AD pathologies, and synaptic/behavioral abnormalities. Further, no toxic effects were observed with treatment of three AD mice with TFP5 ip for 10 weeks. Treatment did not alter the role of the P35/Cdk5 complex, which is involved in brain development and survival.

Based on these findings, disclosed herein are isolated peptides, isolated nucleic acids, pharmaceutical compositions and methods of using such to treat neurodegenerative diseases. In one embodiment, an isolated peptide comprises a Cdk5 inhibitory peptide domain and a PTD. For example, an isolated peptide comprises a Cdk5 inhibitory domain that has at least 95% sequence identity to the amino acid sequence set forth as SEQ ID NO: 1, wherein the Cdk5 inhibitory domain is linked to a PTD. In one example, the Cdk5 inhibitory domain comprises the amino acid sequence set forth as SEQ ID NO: 1. In another example, the Cdk5 inhibitory domain consists of the amino acid sequence set forth as SEQ ID NO: 1. In some examples, the PTD comprises a trans-activator of transcription (TAT) domain with at least 95% sequence identity to the amino acid sequence set forth as one of SEQ ID NO: 3, 4, 5, 6 or 7. In one example, the TAT domain comprises the amino acid sequence set forth as one of SEQ ID NO: 3, 4, 5, 6 or 7. In another example, the TAT domain consists of the amino acid sequence set forth as one of SEQ ID NO: 3, 4, 5, 6 or 7.

In some embodiments, a disclosed isolated polypeptide has an amino acid sequence with at least 95% sequence identity to the amino acid sequence set forth as SEQ ID NO: 2. In one example, the isolated polypeptide comprises the amino acid sequence set forth as SEQ ID NO: 2. In other examples, the isolated polypeptide consists of the amino acid sequence set forth as SEQ ID NO: 2.

Also provided are pharmaceutical compositions including any of the disclosed peptides and a pharmaceutically acceptable carrier. In one example, the pharmaceutical composition is for use in the manufacture of a medicament or for use as a medicament.

Isolated nucleic acids are also disclosed that encode the disclosed polypeptides.

Methods of use of the disclosed peptides are also disclosed. In one example, a method of reducing or inhibiting one or more symptoms associated with a neurodegenerative disease is disclosed. The method includes administering to the subject (for example via ip administration) a therapeutically effective amount of one or more of the disclosed peptides or pharmaceutical compositions, thereby reducing or inhibiting one or more symptoms associated with the neurodegenerative disease. Improvement can include a decrease in Cdk5 phosphorylation activity as compared to Cdk5 phosphorylation activity prior to administration of the therapeutically effective amount of one or more disclosed pharmaceutical composition. In some embodiments, an improvement can include altering a behavior, such as an improvement in memory, including increase in a subject's short term or long term memory recall.

Also disclosed is a method for modulating Cdk5 activity including contacting a cell, such as a neuronal cell (e.g., a neuronal cell present in a mammal, such as a human) with a therapeutically effective concentration of one or more disclosed peptides or pharmaceutical compositions in which the pharmaceutical composition modulates the activity of in the treated cell relative to Cdk5 activity in an untreated cell, thereby reducing or inhibiting Cdk5-mediated neurodegenerative disease. In one example, modulating activity of Cdk5 includes reducing and or inhibiting Cdk5 hyperphosphorylation. In an example, contacting the cell with one or more agents comprises administering the one or more agents to the mammal.

In some examples, the neurodegenerative disease is a disorder associated with aberrant Cdk5 activity, including hyperphosphorylation. Exemplary neurodegenerative diseases, include, but are not limited to, ALS, AD, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy Body dementia, MS, PD, tropical ataxic neuropathy, ALS/PD, lathyrsism, primary lateral sclerosis, spinal muscular atrophy or any combination thereof.

Kits for reducing or inhibiting one or more symptoms associated with a neurodegenerative disease including one or more of the disclosed pharmaceutical compositions are also disclosed. Additionally, kits can include additional compounds, such as protease and/or proteasome inhibitors. Pharmaceutical compositions can be used alone or in association with other combinations, such as protease and/or proteasome inhibitors.

II. Abbreviations and Terms

AA: amino acid
Aβ: Abeta amyloid
AD: Alzheimer's disease
ALS: amyotrophic lateral sclerosis
APP: amyloid precursor protein
BBB: blood brain barrier
BME: β-mercaptoethanol
CDK5: cyclin dependent kinase 5
CNS: central nervous system
CPM: counts per minute
DIC: days in culture
dn: dominant negative
EV: empty vector
FITC: fluorescein isothiocyanate
GFP: green fluorescent protein
GFAP: glial fibrillary acidic protein
HRP: horseradish peroxidase
ICC: immunocytochemistry
ip: intraperitoneal
MRI: magnetic resonance imaging
MS: multiple sclerosis
NF: neurofilament
NFH neurofilament protein H
NF-M/H: neurofilament protein M/H
NFP: neurofilament protein
NFT: neurofibrillary tangle
PBS: phosphate buffered saline
PCR: polymerase chain reaction
PD: Parkinson's disease
PHF: paired helical filament
PS: presenilin
PTD: Protein transduction domain
TAT: Trans-activator of Transcription
WT: wild-type The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

Additional terms commonly used in molecular genetics can be found in Benjamin Lewin, Genes V published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

All sequences associated with the GenBank Accession Nos. mentioned herein are incorporated by reference in their entirety as were present on Sep. 29, 2010 to the extent permissible by applicable rules and/or law.

Administration: To provide or give a subject an agent, such as a disclosed peptide or pharmaceutical composition, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes. A particular type of administration is intraperitoneal (ip).

Alzheimer's disease (AD): A progressive brain disorder that occurs gradually and results in memory loss, behavioral and personality changes, and a decline in mental abilities. These losses are related to the death of brain cells and the breakdown of the connections between them. The course of this disease varies from person to person, as does the rate of decline. On average, AD patients live for 8 to 10 years after they are diagnosed, though the disease can last up to 20 years. AD advances by stages, from early, mild forgetfulness to a severe loss of mental function. At first, AD destroys neurons in parts of the brain that control memory, especially in the hippocampus and related structures. As nerve cells in the hippocampus stop functioning properly, short-term memory fails. AD also attacks the cerebral cortex, particularly the areas responsible for language and reasoning.

Amyotrophic lateral sclerosis (ALS): A progressive, usually fatal, neurodegenerative disease caused by the degeneration of motor neurons. As a motor neuron disease, the disorder causes muscle weakness and atrophy throughout the body as both the upper and lower motor neurons degenerate, ceasing to send messages to muscles. Unable to function, the muscles gradually weaken, develop fasciculations (twitches) because of denervation, and eventually atrophy because of that denervation. The subject may ultimately lose the ability to initiate and control all voluntary movement except for the eyes. ALS is also known as Lou Gehrig's disease.

Blood-brain barrier (BBB): The barrier formed by epithelial cells in the capillaries that supply the brain and central nervous system. This barrier selectively allows entry of substances such as water, oxygen, carbon dioxide, and nonionic solutes such as glucose, alcohol, and general anesthetics, while blocking entry of other substances. Some small molecules, such as amino acids, are taken across the barrier by specific transport mechanisms.

Contacting: Placement in direct physical association; includes both in solid and liquid form. Contacting includes contact between one molecule and another molecule. Contacting can occur in vitro with isolated cells or tissue or in vivo by administering to a subject.

Cyclin dependent kinase 5 (Cdk5): A member of the cyclin dependent kinase (Cdk) family of serine/threonine kinases, most of which are key regulators of the cell cycle. Unlike mitotic Cdks, Cdk5 plays a primary role in brain development, neuronal migration, neurite outgrowth and axon patterning. Cdk5 activity is regulated through associating with its neuron-specific activators, P35 and P39. Cdk5 has also been implicated as a player in learning and memory. Normally, Cdk5 activity is tightly regulated but under conditions of neuronal stress it is deregulated leading to hyperactivity, neuronal pathology and cell death. Hyperactivity of Cdk5 may be involved in neurodegenerative disorders. As used herein, a cyclin dependent kinase 5 inhibitory domain, is a domain that reduces or inhibits one or more biological functions of Cdk5, such as kinase activity (phosphorylation).

Decrease: To reduce the quality, amount, or strength of something. In one example, a therapy decreases or reduces one or more symptoms associated with a neurodegenerative disease. For example, a therapy decreases or inhibits Cdk5 phosphorylation, for example by at least 2-fold, for example at least 3-fold, at least 4-fold, at least 5-fold, at least 10-fold as compared to a control (such as Cdk5 phosphorylation activity in the absence of the therapy or a reference value known to be representative of Cdk5 phosphorylation in a subject afflicted with a neurodegenerative disease). Such decreases can be measured using the methods disclosed herein including kinase activity assays.

Inhibiting or Treating a Disease: Inhibiting the full development of a disease or condition, for example, in a subject who is at risk for a disease such as a neurodegenerative disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease, such as a particular neurodegenerative disease.

Label: A detectable compound or composition that is conjugated directly or indirectly to another molecule to facilitate detection of that molecule, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, nitorimidazoles, enzyme substrates, cofactors, ligands, chemiluminescent agents, fluorophores, haptens, enzymes, and combinations thereof. Methods for labeling and guidance in the choice of labels appropriate for various purposes are discussed for example in Sambrook et al. (*Molecular Cloning: A Laboratory Manual*, Cold Spring Harbor, N.Y., 1989) and Ausubel et al. (In *Current Protocols in Molecular Biology*, John Wiley & Sons, New York, 1998).

In some embodiments, the label is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ. In some examples, a disclosed peptide is labeled.

Linker: A relatively short series of amino acids (for example, between 2 and 150 amino acids) that separates elements or domains of a fusion protein. Examples of specific linkers can be found, for instance, in Hennecke et al. (*Protein Eng.* 11:405-410, 1998); and U.S. Pat. Nos. 5,767,260 and 5,856,456.

Linkers may be repetitive or non-repetitive. One classical repetitive linker used in the production of single chain Fvs (SCFvs) is the $(Gly_4Ser)_3$ (or $(GGGGS)_3$ or $(G_4S)_3$) linker. Non-repetitive linkers also have been produced and methods for the random generation of such linkers are known (Hennecke et al., *Protein Eng.* 11:405-410, 1998). In addition, linkers may be chosen to have more or less secondary character (e.g. helical character, U.S. Pat. No. 5,637,481) depending on the conformation desired in the final fusion protein.

Modulate or modulating: To adjust, alter, regulate an activity, a degree or rate of such. Modulating can be increasing or a decreasing an activity. In one example, a pharmaceutical composition, including one or more of the disclosed Cdk5 inhibitory peptides, is administered to modulate (reduce or inhibit) one or more signs or symptoms of a neurodegenerative disorder or disease.

Multiple sclerosis (MS): A slowly progressive CNS disease characterized by disseminated patches of demyelination in the brain and spinal cord, resulting in multiple and varied neurological symptoms and signs, usually with remissions and exacerbation. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis is a clinical course of MS that is characterized by clearly defined, acute attacks with full or partial recovery and no disease progression between attacks. Secondary-progressive multiple sclerosis is a clinical course of MS that initially is relapsing-remitting, and then becomes progressive at a variable rate, possibly with an occasional relapse and minor remission. Primary progressive multiple sclerosis presents initially in the progressive form. A clinically isolated syndrome is the first neurologic episode, which is caused by inflammation/demyelination at one or more sites in the CNS.

Neurodegenerative disorder or disease: Refers to any type of disorder or disease that is characterized by the progressive deterioration of the nervous system. In some cases, a neurodegenerative disease is associated with axon damage. Axon damage includes axon degeneration and a reduction in axon density, for example in the white matter of the caudal spinal cord. White matter tissue damage includes axons undergoing Wallerian-like degeneration, reduced nerve fiber density, and demyelination. White matter tissue damage can be determined by histological examination of white matter, for example from the ventrolateral or dorsal thoracic spinal cord. White matter tissue damage may also be determined by MRI. Evidence of axonal damage can be inferred from presence of abnormal MRI signals, such as permanently decreased $T_1$ signals ("black holes"), decreased n-acetyl aspartate (NAA) and whole brain atrophy.

Axon damage also includes decreased neurofilament phosphorylation (NF-P) (see e.g. Trapp et al., *N. Engl. J. Med.* 338:278-285, 1998). Neurofilaments in myelinated axons are normally heavily phosphorylated. NF-P can be determined by immunohistochemical staining. A reduction in NF-P reflects demyelination and axon damage. Decreasing axon damage in a subject includes a reduction in white matter tissue damage as compared with an untreated subject, such as a reduction in the decrease in NF-P as compared with an untreated subject. Decreasing axon damage also encompasses preventing axon damage and repair of axon damage. Repair of axon damage in a subject includes a reduction in white matter tissue damage or a reduction in the decrease in NF-P as compared with an earlier time point, for example prior to beginning treatment with other compounds used to treat an axonal disorder, including a neurodegenerative disease.

In one example, a neurodegenerative disorder is a disorder associated with Cdk5 hyperphosphorylation. In some examples, a neurodegenerative disorder, such as AD, PD, ALS, or a combination thereof is associated with an increase in neurofilament phosphorylation (such as hyperphosphorylation of neurofilament protein M or H(NF-M/H), for example at least a 2 fold increase in neurofilament M or H phosphorylation as compared to phosphorylation levels in a control, or non-diseased sample). In some particular examples, AD is associated with a 5 to 8 fold increase in neurofilament M phosphorylation or a 2 to 8 fold increase in neurofilament H phosphorylation. In some examples, a neurodegenerative disorder is ALS, AD, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy Body dementia, MS, PD, tropical ataxic neuropathy, ALS/PD, lathyrsism, primary lateral sclerosis, spinal muscular atrophy or any combination thereof. In one example, a neurodegenerative disease is AD, ALS, PD or a combination thereof.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, for example a "recombinant polypeptide." A recombinant nucleic acid may serve a non-coding function (for example a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. (herein incorporated by reference).

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. In other examples, a molecule is "operably linked" to another molecule when the two molecules are connected by a linker, for example a linker connecting a peptide to another molecule, such as solid support or a detectable label, or linker connecting two peptides, such as two or more Cdk5 inhibitory domains disclosed herein.

Optional: A term used to indicate that the subsequently described event or circumstance can but need not occur, and that the description includes instances where said event or circumstance occurs and instances where it does not.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application. In one example, parenteral refers to intraperitoneal administration.

Parkinson's disease (PD): An idiopathic, slowly progressive, degenerative CNS disorder characterized by slow and decreased movement, muscular rigidity, resting tremor, and postural instability. The loss of substantia nigra neurons, which project to the caudate nucleus and putamen, results in the depletion of the neurotransmitter dopamine in these areas.

Peptide: Any compound composed of amino acids or amino acid analogs chemically bound together. Peptide as used herein includes oligomers of amino acids, amino acid analog, or small and large peptides, including polypeptides or proteins and any chain of amino acids, regardless of length or post-translational modification (such as glycosylation or phosphorylation). In one example, a peptide is two or more amino acids joined by a peptide bond. Typically, a peptide consists of fewer than fifty amino acids; for example, consisting of approximately 7 to approximately 40 amino acids, consisting of approximately 7 to approximately 30 amino acids, consisting of approximately 7 to approximately 20 amino acids. In one example, a peptide consists of 24 amino acids and is referred to as P5 (SEQ ID NO: 1).

"Peptide" applies to amino acid polymers to naturally occurring amino acid polymers and non-naturally occurring amino acid polymer as well as in which one or more amino acid residue is a non-natural amino acid, for example a artificial chemical mimetic of a corresponding naturally occurring amino acid.

A "polypeptide" is a polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

The term "soluble" refers to a form of a polypeptide that is not inserted into a cell membrane.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine. In some examples, one or more conservative amino acid substitutions are made to a Cdk5 inhibitory peptide, such as P5 (SEQ ID NO: 1).

Pharmaceutical composition: A chemical compound or composition capable of inducing a desired therapeutic or prophylactic effect when properly administered to a subject. A pharmaceutical composition can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In a particular example, a pharmaceutical agent is an agent that significantly reduces one or more symptoms associated with a neurodegenerative disease.

Pharmaceutically Acceptable Carriers or vehicles: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic compounds or molecules, such as one or more peptides provided herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In a particular embodiment the carrier is one that allows the therapeutic compound to cross the blood-brain barrier. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Protease: An enzyme that catalyses the hydrolysis of peptide bonds, for example peptide bonds in a protein. Examples of proteolytic enzymes include endoproteases, such as trypsin, chymotrypsin, endoprotease ArgC, endoprotease aspN, endoprotease gluC, thermolysin, and endoprotease lysC. The specific bonds cleaved by an endoprotease or a chemical protein cleavage agents may be more specifically referred to as "endoprotease cleavage sites" and "chemical protein cleavage agent sites," respectively. Proteins typically contain one or more intrinsic protein cleavage agent sites recognized by one or more protein cleavage agents by virtue of the amino acid sequence of the protein. A protease inhibitor is an agent that inhibits the activity of a protease.

Protein transduction domain (PTD): A polypeptide, polynucleotide, carbohydrate, or organic or inorganic compound that facilitates traversing a cell membrane, including the blood brain barrier (BBB). In one example, the protein transduction domain is an HIV trans-activator of transcription (TAT) protein transduction domain which facilitates the transport of one of the disclosed Cdk5 inhibitory peptides across the BBB. PTDs can be naturally occurring or synthetically produced.

Purified: The term "purified" does not require absolute purity; rather, it is intended as a relative term. Thus, for example, a purified polypeptide (such as a Cdk5 inhibitory polypeptide), protein or other active compound is one that is isolated in whole or in part from naturally associated proteins and other contaminants, in which the polypeptide or other active compound is purified to a measurable degree relative to its naturally occurring state, for example, relative to its purity within a cell extract or chemical synthesis checker.

In certain embodiments, the term "substantially purified" refers to a polypeptide, protein or other active compound that has been isolated from a cell, cell culture medium, or other crude preparation and subjected to fractionation to remove various components of the initial preparation, such as proteins, cellular debris, and other components. Such purified preparations can include materials in covalent association with the polypeptide, such as glycoside residues or materials admixed or conjugated with the polypeptide, which may be desired to yield a modified derivative or analog of the polypeptide or to produce a combinatorial therapeutic formulation, conjugate, fusion protein or the like. The term purified thus includes such desired products as peptide and protein analogs or mimetics or other biologically active compounds wherein additional compounds or moieties are bound to the polypeptide in order to allow for the attachment of other compounds and/or provide for formulations useful in therapeutic treatment or diagnostic procedures.

Generally, substantially purified polypeptides, proteins or other active compounds include more than 80% of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the polypeptide or other active compound is purified to represent greater than 90%, often greater than 95% of all macromolecular species present in a purified preparation prior to admixture with other formulation ingredients. In other cases, the purified preparation can be essentially homogeneous, wherein other macromolecular species are less than 1%.

Recombinant: A recombinant nucleic acid or polypeptide is one that has a sequence that is not naturally occurring or has a sequence that is made by an artificial combination of two otherwise separated segments of sequence. This artificial combination is often accomplished by chemical synthesis. One of ordinary skill in the art will appreciate that many different recombinant polynucleotides and recombinant polypeptides may be created by molecular engineering.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene* 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes human and non-human mammals.

Substitution: The replacement of one thing with another. With reference to an amino acid in a polypeptide "substitution" means replacement of one amino acid with a different amino acid. With reference to a nucleotide in a nucleic acid sequence "substitution" means replacement of one nucleotide with a different nucleotide.

Symptom and sign: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting a neurodegenerative disorder or disease. In one example, reducing or inhibiting one or more symptoms or signs associated with a neurodegenerative disease or disorder, includes reducing or inhibiting Cdk5 hyperphosphorylation by a desired amount, for example by at least 20%, at least 50%, at least 60%, at least 70%, at least 80%, at least 90%, at least 95%, at least 98%, or even 100%, as compared to the phosphorylation in the absence of one or more of the disclosed Cdk5 inhibitory peptides.

Therapeutically effective amount or concentration: An amount of a composition that alone, or together with an additional therapeutic agent(s) sufficient to achieve a desired effect in a subject, or in a cell, being treated with the agent. The effective amount of the agent will be dependent on several factors, including, but not limited to the subject or cells being treated, and the manner of administration of the therapeutic composition. In one example, a therapeutically effective amount or concentration is one that is sufficient to prevent advancement, delay progression, or to cause regression of a disease, or which is capable of reducing symptoms caused by the disease, such as a neurodegenerative disease.

In one example, a desired response is to reduce or inhibit one or more symptoms associated with the neurodegenerative disease. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even 100%, as compared to the sign or symptom in the absence of the conjugate. In one particular example, a desired response is to reduce or inhibit the Cdk5 phosphorylation by a desired amount, for example by at least 20%, at least 50%, at least 60%, at least 70%, at least 80%, at least 90%, at least 95%, at least 98%, or even 100%, as compared to the Cdk5 phosphorylation in the absence of the disclosed peptide.

A therapeutically effective amount of a disclosed pharmaceutical composition can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 100 μg-100 mg per kg body weight if administered intravenously. In some embodiments, a therapeutically effective amount is between 10 to 100 mg/kg body weight administered ip, including 20 to 80 mg/kg body weight, 30 to 70 mg/kg body weight, or 40 to 60 mg/kg, such as about 20 mg/kg, about 30 mg/kg, about 40 mg/kg, about 45 mg/kg, about 50 mg/kg, about 55 mg/kg, about 60 mg/kg, 70 mg/kg, about 80 mg/kg or about 90 mg/kg.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

III. Isolated Peptides

Disclosed herein are isolated peptides, such as isolated peptides for use to treat neurodegenerative diseases. A disclosed isolated peptide includes at least one Cdk5 inhibitory domain and a PTD. In some examples, an isolated peptide includes a Cdk5 inhibitory domain, a PTD and at least one spacer/linker moiety and/or one or more additional amino acids. In additional examples, an isolated peptide includes a PTD and multiple Cdk5 inhibitory domains. In further examples, the disclosed isolated peptide is labeled. In additional examples, an isolated peptide includes a PTD and at least one Cdk5 inhibitory domain that allows the isolated peptide to compete with hyperactive P25 regulatory molecule in binding to Cdk5 kinase.

The one of more Cdk5 inhibitory domains can be attached to the PTD either directly or by a linker/spacer moiety by methods known to those of skill in the art (and as described in more detail below). For example, recombinant DNA technology can be used to add the Cdk5 inhibitory domain to a PTD to produce a disclosed peptide. Details of suitable recombinant DNA technology can be found, for example, in Sambrook et al. (ed.), Molecular Cloning: A Laboratory Manual 2nd ed., vol. 1-3, Cold Spring Harbor Laboratory Press, Cold Spring, Harbor, N.Y., 1989. In one example, the PTD is added to the N-terminus of the Cdk5 inhibitory domain. In another example, the PTD is added to the C-terminus of Cdk5 inhibitory domain. In specific embodiments, the PTD is covalently linked to the N-terminus or to the C-terminus of a Cdk5 inhibitory domain.

In one example, a disclosed peptide includes a Cdk5 inhibitory domain that has at least 95% sequence identity to the amino acid sequence set forth as SEQ ID NO: 1 (P5) and has the ability to reduce or inhibit Cdk5 activity (such as phosphorylation). In another example, the disclosed peptide includes a Cdk5 inhibitory domain linked to a PTD, wherein the disclosed peptide has an amino acid sequence with at least 95% sequence identity to the amino acid sequence set forth as SEQ ID NO: 2 (P5 covalently linked to a PTD) and has the ability to reduce or inhibit Cdk5 activity (such as phosphorylation). In some examples, the isolated polypeptide comprises the amino acid sequence set forth as SEQ ID NO: 2. In other examples, the isolated polypeptide consists of the amino acid sequence set forth as SEQ ID NO: 2.

In some examples, the disclosed isolated peptides include a label to assist with the detection of the peptide. For example, a peptide includes a Cdk5 inhibitory domain, a PTD, at least one spacer (linker) moiety and/or additional amino acid, and a label. Any label known to one of skill in the art can be employed that allows for peptide detection without interfering with the delivery or activity of the peptide. In one example, the peptide includes a fluorescent label. In a particular example, the fluorescent label is fluorescein isothiocyanate (FITC). In another example, the disclosed isolated peptide has an amino acid sequence with at least 95% sequence identity to the amino acid sequence set forth as SEQ ID NO: 17 (a Cdk5 inhibitory domain and a PTD with a three glycine linker). In some examples, the isolated polypeptide comprises the amino acid sequence set forth as SEQ ID NO: 17. In other examples, the isolated polypeptide consists of the amino acid sequence set forth as SEQ ID NO: 17. In yet further examples, the isolated polypeptide having the amino acid sequence set forth as SEQ ID NO: 17 is linked to a detectable label. In a particular example, the isolated peptide is SEQ ID NO: 17 linked to FITC (also referred to as TFP5). The activity of the isolated polypeptide set forth as SEQ ID NO: 1 (P5) is not altered by the addition of a PTD, a linker molecule, and/or a detectable label. Thus, polypeptide sequences set forth as SEQ ID NO: 2, SEQ ID NO: 17, or SEQ ID NO: 17 linked to FITC (TFP5) have the ability to reduce or inhibit Cdk5 activity (such as phosphorylation).

Variant amino acid sequences may be 80, 85, 90, 93, 95, 98, or 99% identical to the amino acid sequences disclosed herein.

a. Cdk5 Inhibitory Domain

The disclosed peptide includes a Cdk5 inhibitory domain including at least 15 consecutive amino acids from residues 154-279 of P35 (SEQ ID NO: 16), for example at least 18, at least 20, at least 24, at least 30, at least 40, at least 50, such as between 15-100, 20-90, 40-60, 15-30, 20-27, 23-25, including 16, 17, 18, 19, 20, 21, 22, 23, 24, 25, 26, 27, 28 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids and has the ability to reduce or inhibit Cdk5 activity (such as phosphorylation). In one example, the disclosed Cdk5 inhibitory domain has at least 80%, such as 85%, 90%, 93%, 95%, 98%, 99% or greater sequence identity to the amino acid sequence set forth as SEQ ID NO: 1 and has the ability to reduce or inhibit Cdk5 activity (such as phosphorylation). In one example, the Cdk5 inhibitory domain is P5 and comprises the amino acid sequence set forth as SEQ ID NO: 1 (residues spanning 154-279 of SEQ ID NO: 16). In another example, the Cdk5 inhibitory domain consists of the amino acid sequence set forth as SEQ ID NO: 1. Additional Cdk5 inhibitory domains include P1 (spanning from E211-A277 of SEQ ID NO: 16), P2 (spanning M237-A277 of SEQ ID NO: 16), P3 (spanning E221-L267 of SEQ ID NO: 16), and P4 (spanning E221-L249 of SEQ ID NO: 16).

Additional Cdk5 inhibitory domains include at least 15 consecutive amino acids from residues 154-279 of P35, for example at least 18, at least 20, at least 24, at least 30, at least 40, at least 50, such as between 15-100, 20-90, 40-60, 15-30, 20-27, 23-25, including 16, 17, 18, 19, 20, 21, 22, 23, 24, 25, 26, 27, 28 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids, wherein the Cdk5 inhibitory domain includes at least E255, W259, A233 or a combination thereof and has the ability to reduce or inhibit Cdk5 activity (such as phosphorylation).

b. Protein Transduction Domain (PTD)

PTDs constitute a family of polypeptides that facilitate protein transduction across membranes in a receptor-independent manner (Wadia and Dowdy, Curr. Protein Pept. Sci. 4(2):97-104, 2003). This phenomena was originally described for the human immunodeficiency virus (HIV)-encoded transactivator of transcription (TAT) protein, which was shown to cross membranes and initiate transcription. It was then discovered that the portion of the TAT protein that was required for the transduction of the protein was only an 11 amino acid polypeptide: tyrosine (Y), glycine (G), arginine (R), lysine (K), lysine (K), arginine (R), arginine (R), glutamine (Q), arginine (R), arginine (R), arginine (R) (SEQ ID NO: 3), hereinafter referred to as the TAT peptide. When fused with other proteins, the TAT peptide has been demonstrated to deliver these proteins, varying in size from 15 to 120 kDa, into cells in tissue culture (Frankel and Pabo, Cell 55(6): 1189-93, 1988; Green and Loewenstein, J. Gen. Microbiol. 134(3):849-55, 1988; Vives et al., J. Biol. Chem. 272(25): 16010-7, 1997; Yoon et al., J. Microbiol. 42(4):328-35, 2004; Cai et al., Eur. J. Pharm. Sci. 27(4):311-9, 2006). As disclosed herein the TAT peptide facilitates a P5 peptide sequence to cross the BBB and localize in the brain.

Other TAT polypeptide sequences include, but are not limited to SEQ ID NO: 4, SEQ ID NO: 5, SEQ ID NO: 6, or SEQ ID NO: 7. The Cdk5 inhibitory polypeptides provided herein need not comprise a TAT polypeptide sequence having 100% identity to SEQ ID NO: 3, 4, 5, 6 or 7. The current disclosure contemplates use of a modified or variant TAT polypeptide sequence in which one or more amino acids differ from one of the TAT peptide sequences provided herein. However, the modified or variant TAT polypeptide sequence contemplated for use retains the capacity to facilitate protein transduction across membranes. Methods of preparing TAT fusion proteins and expression vectors comprising TAT fusion proteins are well known in the art (see, for example, U.S. Pat. Nos. 7,094,407 and 7,060,673, herein incorporated by reference in their entirety). Thus, as described herein, TAT polypeptides are useful to facilitate delivery of Cdk5 inhibitory peptides across the BBB. Provided herein are TAT polypeptides fused to Cdk5 inhibitory peptides to allow the fusion proteins to cross the BBB and localize within the brain.

Other PTDs are known in the art and can be used in the compositions and methods described herein. Examples of such PTDs include, but are not limited to, peptides from the VP22 protein of herpes simplex virus (HSV) type 1 (Elliott et al., Cell 88:223-233, 1997); the UL-56 protein of HSV-2 (U.S. Pre-Grant Publication No. 2006/0099677); the Vpr protein of HIV-1 (U.S. Pre-Grant Publication No. 2005/0287648); the third helix of the Drosophila Antennapedia homebox gene (Derossi et al., J. Biol. Chem. 269:10444-10450, 1994; Schwarze et al., Trends Pharmacol. Sci. 21:45-48, 2000); the transportan protein (Pooga, FASEB J. 12:67-77, 1998; Hawiger, Curr. Opin. Chem. Biol. 3:89-94, 1999). A number of artificial peptides also are known to function as PTDs, such as poly-arginine, poly-lysine and others (see, for example, U.S. Pre-Grant Publication Nos. 2006/0106197; 2006/0024331; 2005/0287648; and 2003/0125242; Zhibao et al., Mol. Ther. 2:339-347, 2000; and Laus et al., Nature Biotechnol. 18:1269-1272, 2000). Each of the above-listed publications, and PTD sequences disclosed therein, is herein incorporated by references in its entirety.

c. Optional Spacer/Linker Moieties

According to the present disclosure, a disclosed Cdk5 inhibitory peptide or variant thereof may be attached, such as covalently attached to another Cdk5 inhibitory peptide through an appropriate linker or spacer. For example, an optional spacer/linker moiety and/or additional amino acid may be added to any region of the isolated peptide, including, but not limited to, the N- or C-terminus of the P5 peptide or TAT provided that such moieties do not interfere with conjugate delivery and/or function.

Depending on such factors as the molecules to be linked, and the conditions in which the peptide is being administered (such as if the peptide is being used in a method of detection), the linker can vary in length and composition for optimizing such properties as flexibility, and stability. The linker is a peptide heterologous to the Cdk5 inhibitory peptide or PTD (for example, TAT) sequence. In some examples, a linker is a peptide such as poly-lysine, poly-glutamine, poly-glycine, poly-proline or any combination thereof. In some examples, the peptide linker can be designed to be either hydrophilic or hydrophobic in order to enhance the desired inhibitory activity of the Cdk5 inhibitory peptide sequence, thereby inhibiting Cdk5 hyperphosphorylation. The peptide linker and the individual units of P5 (such as the individual units set forth as SEQ ID NO: 1), and/or a PTD (such as provided in SEQ ID NOs: 3-7) or another protein transduction domain can be encoded as a single fusion polypeptide such that the peptide linker and the individual units of P5 and/or protein transduction domains are joined by peptide bonds.

In some examples, the linker acts as a molecular bridge to link the PTD (for example, TAT) to a detectable label. The linker or spacer can serve, for example, simply as a convenient way to link the two entities, as a means to spatially separate the two entities, to provide an additional functionality to the peptide, or a combination thereof. For example, it may be desirable to spatially separate the PTD and the detectable label to prevent the detectable label from interfering with the activity of the PTD and/or vice versa. The linker can also be used to provide a stability sequence, a molecular tag, or various combinations thereof. In one example, the linker is one or more glycines, such as 2-10 or 4-6, including 2, 3, 4, 5, 6, 7, 8, 9 or 10 glycine residues.

The selected linker can be bifunctional or polyfunctional, e.g., contains at least a first reactive functionality at, or proximal to, a first end of the linker that is capable of bonding to, or being modified to bond to, P5 or TFP5 or variants thereof and a second reactive functionality at, or proximal to, the opposite end of the linker that is capable of bonding to, or being modified to bond to a PTD, such as a TAT PTD. The two or more reactive functionalities can be the same (i.e., the linker is homobifunctional) or they can be different (i.e., the linker is heterobifunctional). A variety of bifunctional or polyfunctional cross-linking agents are known in the art that are suitable for use as linkers (for example, those commercially available from Pierce Chemical Co., Rockford, Ill.). Alternatively, these reagents can be used to add the linker to a Cdk5 inhibitory peptide and/or PTD domain, such as a TAT PTD.

The length and composition of the linker/spacer can be varied considerably provided that it can fulfill its purpose as a molecular bridge. The length and composition of the linker are generally selected taking into consideration the intended function of the linker, and optionally other factors such as ease of synthesis, stability, resistance to certain chemical and/or temperature parameters, and biocompatibility. For example, the linker or spacer should not significantly interfere with the delivery of the Cdk5 inhibitory peptide, such as the delivery of the Cdk5 inhibitory peptide to the brain, or with the activity of the peptide relating to regulating one or more signs or symptoms of a neurodegenerative disease.

Linkers suitable for use according to the present disclosure may be branched, unbranched, saturated, or unsaturated hydrocarbon chains, including peptides as noted above. Furthermore, the linker can be attached to P5 or TFP5 and/or PTD using recombinant DNA technology. Such methods are well-known in the art and details of this technology can be found, for example, in Sambrook et al., supra.

In one embodiment of the present disclosure, the linker is a branched or unbranched, saturated or unsaturated, hydrocarbon chain having from 1 to 100 carbon atoms, wherein one or more of the carbon atoms is optionally replaced by —O— or —NR— (wherein R is H, or C1 to C6 alkyl), and wherein the chain is optionally substituted on carbon with one or more substituents selected from the group of (C1-C6) alkoxy, (C3-C6) cycloalkyl, (C1-C6) alkanoyl, (C1-C6) alkanoyloxy, (C1-C6) alkoxycarbonyl, (C1-C6) alkylthio, amide, azido, cyano, nitro, halo, hydroxy, oxo (=O), carboxy, aryl, aryloxy, heteroaryl, and heteroaryloxy.

Examples of suitable linkers include, but are not limited to, peptides having a chain length of 1 to 100 atoms, and linkers derived from groups such as ethanolamine, ethylene glycol, polyethylene with a chain length of 6 to 100 carbon atoms, polyethylene glycol with 3 to 30 repeating units, phenoxyethanol, propanolamide, butylene glycol, butyleneglycolamide, propyl phenyl, and ethyl, propyl, hexyl, steryl, cetyl, and palmitoyl alkyl chains.

In one example, the linker is a branched or unbranched, saturated or unsaturated, hydrocarbon chain, having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (=O), carboxy, aryl and aryloxy.

In another example, the linker is an unbranched, saturated hydrocarbon chain having from 1 to 50 carbon atoms, wherein one or more of the carbon atoms is optionally replaced by O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (=O), carboxy, aryl and aryloxy.

In a specific example, the linker is a peptide having a chain length of 1 to 50 atoms. In another embodiment, the linker is a peptide having a chain length of 1 to 40 atoms. As known in the art, the attachment of a linker or spacer to a peptide need not be a particular mode of attachment or reaction. Various reactions providing a product of suitable stability and biological compatibility are acceptable.

d. Detectable Label(s)

The disclosed peptides and pharmaceutical compositions can include one or more labels, for example to permit detection of a target nucleic acid molecule using the disclosed probes. In various applications, a disclosed Cdk5 inhibitory peptide or pharmaceutical composition includes a label (e.g., a detectable label). A "detectable label" is a molecule or material that can be used to produce a detectable signal that indicates the presence or concentration of the peptide or composition in a sample. Thus, a labeled peptide or composition provides an indicator of the presence or concentration of such in a sample. The disclosure is not limited to the use of particular labels, although examples are provided.

A label associated with a Cdk5 inhibitory peptide or composition can be detected either directly or indirectly. A label can be detected by any known or yet to be a discovered mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Invitrogen, e.g., see, *The Handbook—A Guide to Fluorescent Probes and Labeling Technologies*, Invitrogen Detection Technologies, Molecular Probes, Eugene, Oreg.). Examples of particular fluorophores that can be attached (for example, chemically conjugated) to a Cdk5 inhibitory peptide or composition are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron®. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Invitrogen Detection Technologies, Molecular Probes (Eugene, Oreg.) and including the ALEXA FLUOR® series of dyes (for example, as described in U.S. Pat. Nos. 5,696,157, 6,130, 101 and 6,716,979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from QuantumDot Corp, Invitrogen Nanocrystal Technologies, Eugene, Oreg.; see also, U.S. Pat. Nos. 6,815,064, 6,682,596 and 6,649,138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et al. (1998) *Science* 281:2013-6, Chan et al. (1998) *Science* 281:2016-8, and U.S. Pat. No. 6,274,323.

Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 nm, 655 nm, 705 nm, or 800 nm emission wavelengths), which are suitable as fluorescent labels in the probes disclosed herein are available from Invitrogen (Carlsbad, Calif.).

Additional labels include, for example, radioisotopes (such as $^3$H), metal chelates such as DOTA and DPTA chelates of radioactive or paramagnetic metal ions like $Gd^{3+}$, and liposomes.

Detectable labels that can be used with the disclosed Cdk5 peptides and pharmaceutical compositions also include enzymes, for example horseradish peroxidase, alkaline phosphatase, acid phosphatase, glucose oxidase, β-galactosidase, β-glucuronidase or β-lactamase. Where the detectable label includes an enzyme, a chromogen, fluorogenic compound, or luminogenic compound can be used in combination with the enzyme to generate a detectable signal (numerous of such compounds are commercially available, for example, from Invitrogen Corporation, Eugene Oreg.). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

e. Other Modifications

The present disclosure contemplates further modifications of a P5 and PTD composition that do not affect the ability of the peptide to selectively target neuronal cells and reduce or inhibit one or more symptoms associated with a neurodegenerative disorder. Such modifications include amino acid substitutions, insertions or deletions, and modifications, for example, to reduce antigenicity of the peptide, to enhance the stability of the peptide and/or to improve the pharmacokinetics of the peptide. In one example, further modifications result in a polypeptide that differs by only a small number of amino acids. Such modifications include insertions (for example, of 1-3 or more residues), or substitutions that do not interfere with the ability of the peptide to selectively target and modulate a neuronal cell.

Various modifications to reduce immunogenicity and/or improve the half-life of therapeutic proteins are known in the art. For example, the peptides can undergo glycosylation, isomerization, or deglycosylation according to standard methods known in the art. Similarly, the peptides can be modified by non-naturally occurring covalent modification for example by addition of polyethylene glycol moieties (pegylation) or lipidation. In one example, the compositions are conjugated to polyethylene glycol to improve their pharmacokinetic profiles. Conjugation can be carried out by techniques known to those skilled in the art (see, for example, Deckert et al., *Int. J. Cancer* 87: 382-390, 2000; Knight et al., *Platelets* 15: 409-418, 2004; Leong et al., *Cytokine* 16: 106-119, 2001; and Yang et al., *Protein Eng.* 16: 761-770, 2003). In one example, antigenic epitopes can be identified and altered by mutagenesis. Methods of identifying antigenic epitopes are known in the art (see for example, Sette et al., *Biologicals* 29:271-276, 2001), as are methods of mutating such antigenic epitopes. In one example, modifications are incorporated to decrease the toxicity of the disclosed peptides. The general toxicity of the peptides according to the present disclosure can be tested according to methods known in the art. For example, the overall systemic toxicity of a disclosed peptide can be tested by determining the dose that kills 100% of neuronal cells (i.e., LD100) following a single treatment.

f. Additional Domains

Optionally, a polypeptide of the present disclosure further includes a series of consecutive amino acids encoding a domain (a protein tag; for example, a myc- or his-tag) that facilitates the isolation and purification of the polypeptide. An "isolated" polypeptide or polynucleotide means a polypeptide or polynucleotide that has been either removed from its natural environment, produced using recombinant techniques, or chemically or enzymatically synthesized. In one embodiment, a polypeptide or polynucleotide of this disclosure is purified, i.e., essentially free from any other polypeptide or polynucleotide and associated cellular products or other impurities. For instance, domains that are useful in the isolation of a polypeptide that has glycosylase activity, such as glycosylase/AP lyase activity, include a histidine domain (which can be isolated using nickel-chelating resins), an S-peptide domain (which can be isolated using an S-protein, see Kim et al. *Protein Sci.* 2:348-356, 1993), and a chitin binding domain (which can bind to chitin beads, see Chong et al. *Gene* 192:271-281, 1997; and Watanabe et al. *J. Bacteriol.* 176:4465-4472, 1994). In one embodiment, the domain is present at the carboxy terminal end of the polypeptide. In one embodiment, the domain can be cleaved from the remainder of the polypeptide (e.g., the polypeptide having pyrimidine glycosylase activity, such as pyrimidine glycosylase/AP lyase activity, fused to a targeting sequence, such as an exogenous targeting sequence) by the use of a protease or self-cleaving sequence.

IV. Nucleic Acids Encoding Cdk5 Inhibitory Polypeptides

The present disclosure also concerns nucleic acid constructs including polynucleotide sequences that encode the isolated peptides disclosed herein, such as isolated nucleic acid molecules and vectors including such nucleic acid molecules. These polynucleotides include DNA, cDNA and RNA sequences, which encode the polypeptide of interest. Thus, this disclosure encompasses polynucleotides encoding the amino acid sequences comprising any of the Cdk5 inhibitory peptides described above, for example peptides comprising a Cdk5 inhibitory peptide (such as P5) and a PTD.

The nucleic acid constructs can include polynucleotides that encode heterologous polypeptides in addition to those set forth above, including SEQ ID NO: 1 or SEQ ID NO: 2, for example peptides that include peptide linkers or other moieties to aid in the purification, detection (such as heterologous fluorescent protein sequences, such as green fluorescent protein and the like), and/or attachment of the peptides to a solid surface (such as GST, biotin, avidin or streptavidin).

The coding region may be altered by taking advantage of the degeneracy of the genetic code to alter the coding sequence such that, while the nucleotide sequence is altered, it nevertheless encodes a peptide having an amino acid sequence the same as the disclosed peptide sequences, for example for optimization of expression in a host cell, such as a bacterial host cell, such as *E. coli*. Based upon the degeneracy of the genetic code, variant DNA molecules may be derived from encoding sequences disclosed herein using standard DNA mutagenesis techniques as described above, or by synthesis of DNA sequences.

To produce such nucleic acid constructs, polynucleotide sequences encoding peptides are inserted into a suitable expression vector, such as a plasmid expression vector. Procedures for producing polynucleotide sequences encoding the peptides disclosed herein and for manipulating them in vitro are well known to those of skill in the art, and can be found (see for example, Sambrook et al., *Molecular Cloning, a Laboratory Manual,* 2nd edition, Cold Spring Harbor Press, Cold Spring Harbor, N.Y., 1989, and Ausubel et al., *Current Protocols in Molecular Biology,* Greene Publishing Associates and John Wiley & Sons, New York, N.Y., 1994).

A wide variety of cloning and in vitro amplification methodologies are well known to persons skilled in the art. A nucleic acid encoding a polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). Methods for the manipulation and insertion of the nucleic acids of this disclosure into vectors are well known in the art (see for example, Sambrook et al., *Molecular Cloning, a Laboratory Manual,* 2nd edition, Cold Spring Harbor Press, Cold Spring Harbor, N.Y., 1989, and Ausubel et al., *Current Protocols in Molecular Biology,* Greene Publishing Associates and John Wiley & Sons, New York, N.Y., 1994). PCR methods are described in, for example, U.S. Pat. No. 4,683,195; Mullis et al., Cold Spring Harbor Symp. *Quant. Biol.* 51:263, 1987; and Erlich, ed., *PCR Technology,* (Stockton Press, NY, 1989).

A polynucleotide sequence encoding the disclosed peptides can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (ATG) in front of a protein-encoding gene, splicing signal for introns, maintenance of the correct reading frame of that gene to permit proper translation of mRNA, and stop codons. A promoter is an array of nucleic acid control sequences that directs transcription of a nucleic acid. A promoter includes necessary nucleic acid sequences (which can be) near the start site of transcription, such as in the case of a polymerase II type promoter (a TATA element). A promoter also can include distal enhancer or repressor elements, which can be located as much as several thousand base pairs from the start site of transcription. Both constitutive and inducible promoters are included (see, for example, Bitter et al., *Methods in Enzymology* 153:516-544, 1987).

The polynucleotides include a recombinant DNA can be incorporated into a vector into an autonomously replicating plasmid or virus or into the genomic DNA of a prokaryote or eukaryote, or which exists as a separate molecule (for example a cDNA) independent of other sequences. Typically, the nucleic acid constructs encoding the peptides of this disclosure are plasmids. However, other vectors (for example, viral vectors, phage, cosmids, etc.) can be utilized to replicate the nucleic acids. In the context of this disclosure, the nucleic acid constructs typically are expression vectors (for example, prokaryotic, eukaryotic, or mammalian expression vectors) that contain a promoter sequence, which facilitates the efficient transcription of the inserted genetic sequence of the host. The expression vector typically contains an origin of replication, a promoter, as well as specific nucleic acid sequences (encoding, for example, a selectable marker) that allow phenotypic selection of the transformed cells.

DNA sequences encoding the peptides of this disclosure can be expressed in vitro by DNA transfer into a suitable host cell. Thus, also disclosed are host cells that include vectors encoding the peptides of this disclosure. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Transformation of a host cell with recombinant DNA can be carried out by conventional techniques as are well known to those skilled in the art. Where the host is prokaryotic, such as *E. coli*, competent cells, which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, methods of transfection of DNA such as calcium phosphate precipitation, conventional mechanical procedures such as microinjection, electroporation, insertion of a plasmid encased in liposomes, or virus vectors can be used. Eukaryotic cells can also be co-transformed with polynucleotide sequences encoding the polypeptide of interest, and a second foreign DNA molecule encoding a selectable phenotype (selectable marker). Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

V. Pharmaceutical Compositions

Provided herein are pharmaceutical compositions including any of the disclosed compounds, such as the disclosed peptides or nucleic acids, and a pharmaceutically acceptable carrier. In particular embodiments, the pharmaceutical composition includes the polypeptide set forth as SEQ ID NO: 2, SEQ ID NO: 17, or SEQ ID NO: 17 covalently linked to a detectable label such as FITC (for example, TFP5). The pharmaceutical composition may also include one or more agents or drugs as known to be therapeutically active in the treatment of a neurodegenerative disorder or disease. In a further embodiment these agents may be selected from the group consisting of steroid, anti-inflammatory compound, immunosuppressive compound, and antioxidant compound. In one embodiment, the pharmaceutical composition is administered intraperitoneally. In other embodiments, the pharmaceutical composition is administered orally. Additional routes of administration may include transdermal, venous, intranasal, and inhalation routes. Inhalational preparations can include aerosols, particulates, and the like. In general, the goal for particle size for inhalation is about 1 µm or less in order that the pharmaceutical reach the alveolar region of the lung for absorption. For administration by inhalation, the pharmaceutical compositions are conveniently delivered in the form of an aerosol spray presentation from pressurized packs or a nebulizer, with the use of a suitable propellant, for instance, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Methods for preparing pharmaceutical compositions are known to those skilled in the art (see Remington's Pharmaceutical Science, 19th ed., Mack Publishing Company, Easton, Pa., 1995). Preparations for parenteral (including intraperitoneal) administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In several embodiments, the composition includes a carrier which facilitates the peptide to cross the blood-brain barrier.

Pharmaceutical compositions for oral use can be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavoring agents, coloring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatin or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monostearate or glyceryl distearate may be employed. Pharmaceutical compositions for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium such as peanut oil, liquid paraffin or olive oil.

Pharmaceutical compositions can include pharmaceutically acceptable salts of the disclosed conjugates. Pharmaceutically acceptable salts of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Description of suitable pharmaceutically acceptable salts can be found in Handbook of Pharmaceutical Salts, Properties, Selection and Use, Wiley VCH (2002).

The peptides described herein can be administered to a subject for therapeutic treatment of a neurodegenerative disorder, such as a neurodegenerative disease. Thus, a therapeutically effective amount of a composition comprising one or more of the disclosed peptides is administered to a subject already suffering from a neurodegenerative disorder, including a neurodegenerative disease (such as ALS, AD, PD or a combination thereof), in an amount sufficient to improve a sign or a symptom of the disorder. Generally a suitable dose is about 1 milligram per kilogram (mg/kg) to about 50 mg/kg, such as a dose of about 1 mg/kg, about 2 mg/kg, about 5 mg/kg, or about 20 mg/kg administered parenterally, for example intraperitoneally (ip), or orally. For example, a suitable dose is about 1 mg/kg to about 100 mg/kg, such as a dose of about 1 mg/kg, about 10 mg/kg, about 20 mg/kg, about 50 mg/kg, or about 100 mg/kg administered ip. Unit dosage forms are also possible, for example 50 mg, 100 mg, 150 mg or 200 mg, or up to 400 mg per dose. However, other higher or lower dosages also could be used, such as from about 0.001 mg/kg to about 1 g/kg, such as about 0.1 to about 500 mg/kg, including about 0.5 mg/kg to about 200 mg/kg.

Single or multiple administrations of the composition comprising one or more of the disclosed conjugates can be carried out with dose levels and pattern being selected by the treating physician. Generally, multiple doses are administered. In a particular example, the composition is administered parenterally, for example intraperitoneally, once per day. However, the composition can be administered twice per day, three times per day, four times per day, six times per day, every other day, twice a week, weekly, or monthly. In some examples, the composition is administered parenterally, for example intraperitoneally, for two or more consecutive days, for example for 3, 4, 5, 6, 7, 8, 9, 10, or more consecutive days. In other examples, the composition is administered parenterally, for example intraperitoneally, once per day for two or more consecutive days. In a specific example, the composition is administered parenterally, for example intraperitoneally, once per day for at least three consecutive days. Treatment can continue for at least a month, for example for two or three months, sometimes for six months or a year, and may even continue indefinitely, i.e., chronically. Repeat courses of treatment are also possible.

In one embodiment, the pharmaceutical composition is administered without sequential or concurrent administration of a second agent for the treatment of a neurodegenerative disorder. In one specific, non-limiting example, one or more of the disclosed peptides is administered without sequential or concurrent administration of other agents, such as without sequential or concurrent administration of an additional agent also known to target the neurodegenerative disorder. In other specific non-limiting examples, a therapeutically effective amount of a disclosed pharmaceutical composition is administered sequentially or concurrently with an additional agent, including an additional neurodegenerative disorder therapy (such as, but not limited to, monoclonal antibodies, an anti-inflammatory agent, such as glatiramer acetate, an anti-oxidant, such as lipoic acid). For example, the disclosed compounds are administered in combination with (sequentially or concurrently) protease and/or proteasome inhibitors, antioxidants, anti-inflammatory drugs or combinations thereof.

VI. Methods of Use

It is shown herein that reducing or inhibiting Cdk5/P25 activity reduces or inhibits one or more symptoms associated with neurodegenerative diseases, such as AD, ALS, or PD. For example, the reducing or inhibiting deregulated Cdk5/P25 activity rescued cortical neurons from Aβ toxicity, tau pathology and cell death. It is also shown herein that the disclosed molecules are able to successfully cross the blood-brain barrier and be specifically translocated to neuronal locations, including neuronal/axonal circuitries. In some embodiments, this is accomplished by ip administration.

Based on these observations, methods of treatment to reduce or eliminate one or more symptoms or signs associated with a neurodegenerative disease are disclosed. For example, a method includes administering to the subject a therapeutically effective amount of one or more of the disclosed pharmaceutical compositions, thereby reducing or inhibiting one or more symptoms associated with the neurodegenerative disease.

In a particular example, the compound or a pharmaceutical composition comprising one or more of the disclosed compounds, for example one or more of the disclosed peptides, readily penetrates the blood-brain barrier when peripherally administered. In some examples, the pharmaceutical composition comprises a compound of the disclosure and a pharmaceutically acceptable carrier, such as one that also facilitates transport across the BBB.

In certain examples, Cdk5 activity (such as hyperphosphorylation) is reduced or decreased as compared to Cdk5 activity prior to administration of the therapeutically effective amount of the pharmaceutical composition.

Also disclosed is a method for modulating Cdk5 activity including contacting a cell, such as a neuronal cell (e.g., a neuronal cell present in a mammal, such as a human) with a therapeutically effective amount of one or more of the disclosed peptide-containing pharmaceutical compositions in which the composition modulates the activity of Cdk5 in the treated cell relative to Cdk5 activity in an untreated cell, thereby reducing or inhibiting a Cdk5-mediated neurodegenerative disorder or disease. In one example, modulating the activity of Cdk5 includes reducing and or inhibiting Cdk5 phosphorylation as compared to Cdk5 phosphorylation in an untreated cell. In some examples, modulating activity of Cdk5 includes modulating Cdk5/P25 activity or Cdk5/P35 activity. In an example, contacting the cell with one or more agents comprises administering the one or more agents to the mammal, such as a human.

In some examples, the methods of use can include selecting a subject in need of treatment. For example, studies can be performed to identify a subject as being afflicted with a neurodegenerative disorder or disease, including, but not limited to, any of the disorders/diseases described herein. Methods of detecting a neurodegenerative disorder/disease are known to those of skill in the art and can include methods of detecting Cdk5 activity or Cdk5 expression, as described herein.

Therapeutically Effective Concentration

In the methods disclosed herein, a therapeutically effective amount of a pharmaceutical composition including a disclosed peptide or pharmaceutical composition described herein is administered to a subject with, or at risk of developing, a neurodegenerative disease, such as AD, ALS, PD or a combination thereof. Assays to determine a therapeutically effective amount of a disclosed pharmaceutical composition for preventing, inhibiting or reducing one or more signs or symptoms associated with a neurodegenerative disorder/disease are well known in the art.

In some examples, a therapeutic effective amount of a disclosed pharmaceutical composition is one in which one or more signs or symptoms associated with a neurodegenerative disorder is reduced or inhibited, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, less than activity in the absence of the composition.

For example, a therapeutic effective amount of a disclosed pharmaceutical composition is one in which Cdk5 activity (such as kinase activity levels) is reduced or inhibited, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to such activity in the absence of the composition. Methods of assessing Cdk5 activity are known to one skilled in the art, including those described herein.

In some examples, a therapeutically effective amount of a disclosed pharmaceutical composition is one in which tau phosphorylation is decreased, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, less than phosphorylation in the absence of the composition.

In some examples, a therapeutically effective amount of a disclosed pharmaceutical composition is one in which motor performance is increased, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, more than activity in the absence of the composition.

In other examples, a therapeutic effective amount of a disclosed pharmaceutical composition is one in which β-amyloid levels are decreased, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, relative to such levels in the absence of the composition. Methods of assessing β-amyloid levels are known to one skilled in the art, including those described in the Examples below.

Dosages, routes of administration of the disclosed pharmaceutical compositions for the methods of treatment are known to those of skill in the art and include, but are not limited to those described herein.

Exemplary Neurodegenerative Disorders/Diseases

Exemplary neurodegenerative disorders, include, but are not limited to, neuropathies associated with production of protein adducts molecules (such as gamma-keto-aldehydes, oxidative metabolites of arachidonic acid), amyotrophic lateral sclerosis (Lou Gehrig's disease), Alzheimer's disease, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy Body dementia, MS, PD, tropical ataxic neuropathy, ALS/PD, lathyrism, primary lateral sclerosis, spinal muscular atrophy or any combination thereof. In some examples, the axonal disorder is ALS, AD, or PD. In one particular example, the axonal disorder is ALS. In some examples, the axonal disorder is a disorder associated with proximal giant axonopathy.

VII. Kits

Provided by this disclosure are kits that can be used to diagnose, prognose, or treat a neurodegenerative disorder/disease. For example, a kit is disclosed herein for preventing or inhibiting a neurodegenerative disorder, such as a neurodegenerative disease including but not limited to AD, ALD, PD or a combination thereof, by reducing or inhibiting one or more symptoms associated with a neurodegenerative disorder/disease in which the kit includes at least one of the disclosed pharmaceutical compositions. The disclosed kits can include instructional materials disclosing means of use of the compositions in the kit. The instructional materials can be written, in an electronic form (such as a computer diskette or compact disk) or can be visual (such as video files). For example, instructions indicate to first perform a baseline measurement of a particular activity, such as measuring Cdk5 activity, such as Cdk5-mediated phosphorylation. Then, administer a disclosed peptide or pharmaceutical composition according to the teachings herein. Administration is followed by re-measuring the particular activity. The activity level prior to treatment is compared to activity observed following treatment. A decrease in activity by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to such activity in the absence of the composition indicates an effective treatment. In a particular embodiment, a greater than 50% reduction indicates an effective treatment. In other embodiments, a greater than 40%, greater than 60%, greater than 70%, greater than 80%, greater than 90%, greater than 95%, reduction indicates an effective treatment. An effective treatment can include, but is not limited to, an increase in patient survival, a slowing of the progression of the particular neurodegenerative disorder, a good prognosis, or a prevention of further neurodegeneration.

Kits are provided that can be used in the therapy assays disclosed herein. For example, kits can include one or more of the disclosed compounds or pharmaceutical compositions, agents (such as antibodies) capable of detecting one or more neurodegenerative biomarkers (for example, measuring Cdk5 activity), or combinations thereof. One skilled in the art will appreciate that the kits can include other agents to facilitate the particular application for which the kit is designed.

In one example, a kit is provided for treating a neurodegenerative disease, such as AD, ALS, PD or a combination thereof. For example, such kits can include one or more of the disclosed pharmaceutical compositions including one or more of the disclosed peptides.

In some examples, a kit is provided for detecting one or more neurodegenerative biomarkers in a biological sample. Kits for detecting neurodegenerative disorder-related molecules can include one or more probes that specifically bind to the molecules. In an example, a kit further includes one or more controls, such as positive and negative controls. In other examples, kits include a Cdk5 inhibitor that is labeled (for example, with a fluorescent, radioactive, or an enzymatic label). Such a diagnostic kit can additionally contain means of detecting a label (such as enzyme substrates for enzymatic labels, filter sets to detect fluorescent labels, appropriate secondary labels such as a secondary antibody, or the like), as well as buffers and other reagents routinely used for the practice of a particular diagnostic method.

In certain examples, kits include additional compounds, such as protease and/or proteasome inhibitors. Pharmaceutical compositions can be used alone or in association with other compounds, such as protease and/or proteasome inhibitors.

The present disclosure is illustrated by the following non-limiting Examples.

EXAMPLES

Example 1

Materials and Methods

This example provides the materials and methods utilized to perform the studies described in Examples 2-10.

Materials:

P35 (C-19) polyclonal antibody, Cdk5 (C-8) polyclonal antibody, Cdk5 (J-3) monoclonal antibody at 1:500 dilutions, Cdc2 Anti-PSTAIR antibody, Cdk2, Cdk4, Cdk6, antibodies were obtained from Santa Cruz Biotechnology Inc (Santa Cruz, Calif.), all used at 1:300-500 dilutions. Phospho-tau-S199/202, PHF1, Tau1 and Tau-5 monoclonal antibodies were obtained from Biosource International Inc. (Camarillo, Calif.) and used at 1:1000 and 1:500 dilutions respectively. AT-8 and AT180 antibodies were purchased from Thermo Scientific (Rockford, Ill.) and used at 1:500. Phosphotau-S422 was purchased from GenScrip (Piscataway, N.J.) and used at 1:1000. Other antibodies include caspase 3 and cleaved caspase-3 obtained from Cell Signaling Technologies (Beverly, Mass.) and used at 1:1000 dilutions, while β-Tubulin antibody from Sigma (St. Louis, Mo.) was used at 1:2000. Secondary horseradish peroxidase conjugated antibodies were obtained from Amersham Biosciences (Piscataway, N.J.) and used at 1:2000. Secondary fluorescence conjugated Oregon Green and Texas Red antibodies, Invitrogen (Carlsbad, Calif.) were used at 1:400. Cdk5 inhibitor roscovitine was obtained from Biomol Research Laboratories, Inc. (Plymouth Meeting, Pa.). P5 peptide was synthesized by 21 Century Biochemicals (Marlsboro, Mass.).

Plasmids and Generation of Recombinant Adenoviruses:

AdEasy system was kindly provided by Dr. Bert Vogelstein, Howard Hughes Medical Institute and Molecular Genetics Laboratory, Johns Hopkins Oncology Center, Baltimore, Md. A serial of Cdk5 related genes were generated by PCR with the following primers with additional restriction enzymes (Not1 and ECORV) sequence underlined and Myc-tag sequence capitalized: 1. P35, forward primer, tttgcggccgccAtgggcacggtgctgtccct (SEQ ID NO: 8), reverse primer, tttgatatcttaccgatccaggcctagga (SEQ ID NO: 9); 2. P25 forward primer, tttgcggccgccAtggcccagccccaccggccca (SEQ ID NO: 10), reverse primer is the same as P35; 3. Cdk5, forward primer, tttgcggccgccAtgcagaaatacgagaaactgga (SEQ ID NO: 11), reverse primer, tttgatatcttagggcggacagaagtcgg (SEQ ID NO: 12); 4. P5, forward primer tttgcggccgccATGGCATCAATGCAGAAGC (SEQ ID NO: 13), TGATCTCAGAGGAGGACCTGAtgaaggagg ccttttgggaccg (SEQ ID NO: 14), reverse primer, tttgatatcttaggcatttatctgcagcatcttt (SEQ ID NO: 15). Recombinant adenoviruses were generated according to the protocol (He et al., *Proc Natl Acad Sci USA* 95(5), 2509-2514, 1998). Briefly, all PCR fragments were cloned into a shuttle vector, pAdTrack-CMV. The resultant plasmids were linearized and subsequently co-transformed into *E. coli* BJ5183 cells with an adenoviral backbone plasmid pAdEasy-1 (Strategy Com.). Recombinants were linearized and transfected into 293-1 cells (Strategy Com.) to generate the recombinant adenoviruses. High viral titers were purified by CsCl banding and mixed with 2× Storage Buffer (10 mM Tris, pH 8.0, 100 mM NaCl, 0.1% BSA, and 50% glycerol, filter sterilized). Viruses were stored as stocks at −20° C. or −70° C. The titers of virus were checked by GFP when infected with related cells.

Cell Culture, Transfection and Infection:

Primary cultures of rat cortical neurons were prepared from E-18 rat fetuses as described previously (Zheng et al., *J Biol Chem* 278(26), 24026-24032, 2003). After 7 days, cells were infected independently or co-infected with empty vector (EV), the constructs of P5, P25, P35, wild-type Cdk5 and dominant negative Cdk5 (changing Lys33 to Thr33) using the Adenoviral vector (pAdTrack-CMV) packaging system as described above. After 48 hours, cells were treated with roscovitine (20 μM) for 1 hour, and/or for 6 hours with 10 μM Aβ1-42 (incubated at 37° C. for seven days before use). The cells were fixed for immunocytochemistry analyses (ICC) or lysed with lysis buffer for immunoprecipitation and Western blot analyses. Cortical neuron cultures were prepared and plated on the cover slips as described. Human embryo kidney cells (HEK293) were grown as described previously (Zheng et al., *Eur J Biochem* 269(18), 4427-4434, 2002). In these studies HEK293 cells on day 1, or neurons on day 5, were transfected with or without Myc-P5-GFP using Lipofectamine 2000 following the manufacturer's instructions.

Western Blot Analysis:

Western blot analysis was performed as previously described (Zheng et al., *Eur J Biochem* 269(18), 4427-4434, 2002). In brief, an equal amount of total protein (20 μg/lane) was resolved on a 4-20% SDS polyacrylamide gel and blotted onto a polyvinylidene difluoride membrane. This membrane was incubated in blocking buffer containing 20 mM Tris-HCl (pH 7.4), 150 mM NaCl, and 0.1% (vol/vol) Tween 20 (TTBS) plus 5% dry milk (w/v) for 1 hour at room temperature followed by incubation overnight at 4° C. in primary antibodies (see antibodies). The membranes were then washed four times in TTBS (5 minutes/each) followed by incubation in secondary antibody (goat-antimouse or goat anti-rabbit IgG (H+L)-horseradish peroxidase (HRP) conjugate at a dilution of 1:3000) for 1 hour at room temperature. Western blots were analyzed using the Amersham Enhanced Chemiluminescence (ECL) kit following the manufacturer's instructions (GE Healthcare, Piscataway, N.J.).

Immunoprecipitation and Kinase Assays:

Kinase assays were performed as previously described (Veeranna, et al., *J Neurosci* 18(11), 4008-4021, 1998). Briefly, 7 days in culture (7 DIC) primary rat cortical neurons were infected with P25, P35, Cdk5 wild-type, dominant negative-Cdk5 and P5 using the lentiviral gene delivery as described earlier. Cdk5 was immunoprecipitated using the polyclonal C8 antibody overnight at 4° C. and immunoglobulin isolated using Protein A sepharose beads for 2 hours at 4° C. Immunoprecipitates were washed three times with lysis buffer and then once with 1× kinase buffer containing 20 mM Tris-Cl pH 7.4, 1 mM EDTA, 1 mM EGTA, 10 mM MgCl2, 10 mM sodium fluoride and 1 mM sodium orthovanadate. Endogenous Cdks were immunoprecipitated from HEK 293 cells using their respective antibodies and treated as above. Kinase assays were performed in the same buffer containing 1 mM DTT, 0.1 mM ATP and 0.185 MBq [γ-32P] ATP with 20 μg of histone H1 as the substrate. Phosphorylation was performed in a final volume of 50 μA incubated at 30° C. for 60 minutes, stopped by the addition of 10% SDS sample buffer and heating at 95° C. for 5 minutes. Samples were separated by SDS-PAGE, gels were stained with Coomassie, destained, dried and exposed to autoradiography. In pad assays, 25 μl aliquots of the incubation mixture were placed on a Whatman p80 paper square, washed and dried and placed in a scintillation vial for counting.

Effect of Tubulin Polymerization on Cdk5 Activity:

Tubulin polymerization was performed as detailed in a previous report (Hou et al., *J. Biol. Chem.*, 282(26), 18666-18670, 2007). Briefly, active kinase Cdk5/P35 (2 ng/μL) or active Cdk5/P25 (1 ng/μL) were incubated with β-tubulin (enzyme: tubulin at 1:100) in the PEM buffer (80 mM PIPES, 2 mM MgCl2, 1 mM EGTA PH 7.0) supplemented with 1 mM GTP at 35° C. for 45 minutes. Following the incubation, Cdk5 kinase assays were performed with or without the addition of 0.45 μM or 0.90 μM P5.

Immunocytochemistry:

Immunocytochemistry (ICC) was performed as previously described (Zheng et al., *EMBO Journal* 24(1), 209-220, 2005). Briefly, cells were fixed on cover slips for 30 minutes at room temperature in 4% paraformaldehyde in PBS, then permeabilized and blocked in 5% FBS with 0.1% Triton X-100 in 1×PBS for 1 hour. The cover slips were incubated overnight at 4° C. with primary antibodies diluted in blocking buffer. After a wash in PBS (three times, 15 minutes each) the cover slips were incubated with fluorescein goat anti-mouse IgG or Texas Red goat anti-rabbit IgG, and secondary antibody for 1 hour at room temperature. This was followed by washing three times with PBS, and mounting in an aqueous medium. Fluorescent images were obtained with a Zeiss LSM-510 laserscanning confocal microscope. Images were processed and merged by Adobe Photoshop software.

TUNEL Assay for Apoptosis:

Primary cortical neuron cells were cultured for 5 days on glass coverslips coated with poly-L-lysine, and transfected with or without P5 using Lipofectamine 2000. After 24 hours, TUNEL staining was done according to the manufacturer's instructions. Cells were washed three times in PBS, fixed for 1 hour at room temperature in fresh 4% paraformaldehyde in PBS, and permeabilized (0.1% Triton X-100 in 0.1 sodium citrate) for 2 minutes on ice. After washing 2× with PBS, TUNEL reaction mixture (50 µl) was added and incubated in a humidified atmosphere at 37° C. for 1 hour. TUNEL staining and fluorescent images were visualized with a Zeiss LSM-510 laser-scanning confocal microscope. Images were processed and merged by Adobe Photoshop software.

Example 2

Identification of Cdk5 Inhibitory Peptides Derived from P35

This example provides the identity of a Cdk5 inhibitory peptides derived from P35.

Figure 1B:
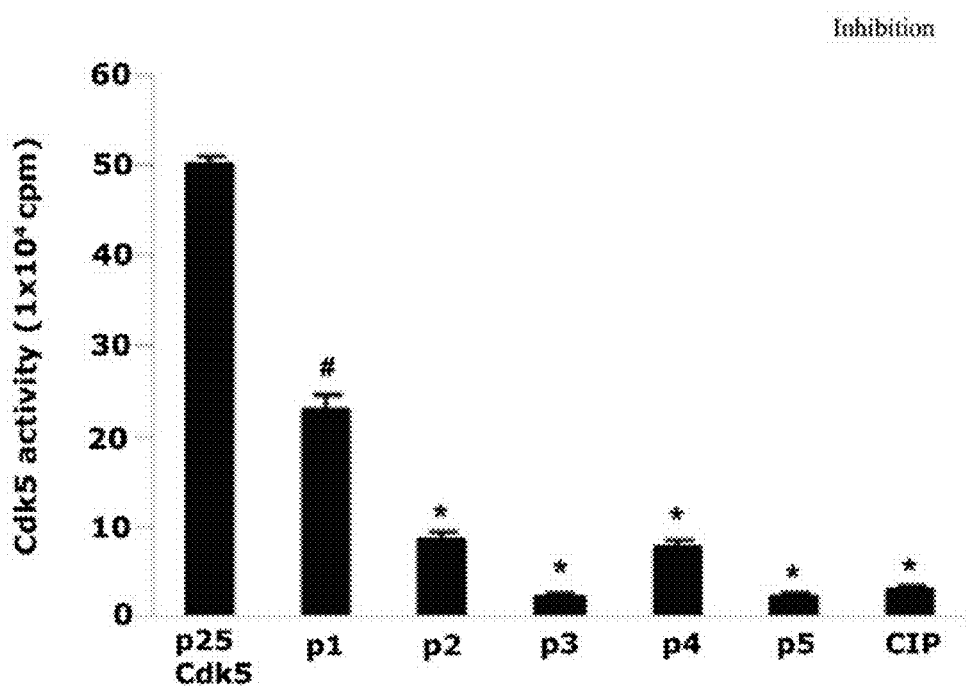
FIG. 1B is a histogram summary comparison of the inhibitory effects of peptides derived from CIP in a standard in vitro pad assay of Cdk5/P25 activity. P3 and P5 were the most effective inhibitors under these conditions, reducing activity more than 90%. Data represent the mean±SE of three independent studies (*p<0.01).
Figure 10:
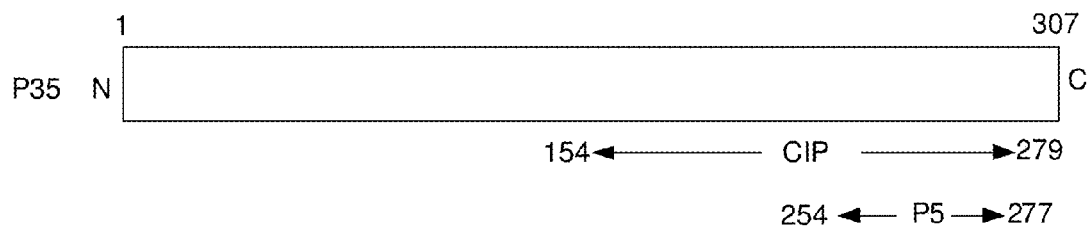
FIG. 10 is a schematic, illustrating the overlap among P35, CIP and P5.

CIP, a 125-amino acid truncated peptide from P35 (residues 154-279 of SEQ ID NO: 16, human P35 GenBank Accession No. CAA56587, which is hereby incorporated by reference in its entirety as available on Sep. 29, 2010) is a highly effective and specific inhibitor of Cdk5/P25 activity. CIP reduces tau hyperphosphorylation and protects transfected HEK cells and neurons from apoptosis induced by Cdk5/P25. To produce a smaller and more effective inhibitory peptide of Cdk5/P25 for potential therapeutic use, five short peptides in GST vectors were designed and constructed as shown in FIG. 1A. These are GST-P1 (E211-A277 of SEQ ID NO: 16), 67 amino acid residues; GST-P2 (M237-A277), 41 residues; GST-P3 (E221-L267 of SEQ ID NO: 16), 47 residues; GST-P4 (E221-L249 of SEQ ID NO: 16), 29 residues and GST-P5 (K254-A277 of SEQ ID NO: 16) 24 residues. Each was incubated with active Cdk5/P25 in a kinase assay in vitro. The results indicated that all short peptides inhibited Cdk5/P25 activities significantly, but only P3 and P5 are more effective inhibitors than CIP (FIG. 1B). Although both exhibit almost 100% inhibition in vitro, P5 was evaluated further. FIG. 10 provides a comparison of P5 and CIP, relative to P35. Moreover, molecular dynamics simulations revealed that residues E255, W259 and A233 of the P5 peptide bind to the PSSALRE motif of Cdk5, further supporting a potent inhibitor role for P5.

Example 3

P5 In Vitro Inhibition of Cdk5/P25 and Cdk5/P35

This example shows P5 inhibition of both Cdk5/P25 and Cdk5/P35 activities in vitro.

In a dose-dependent kinase assay the effective inhibitory concentration of P5 for both the Cdk5/P25 and Cdk5/P35 complexes was evaluated. His-P5 peptide was added at different concentrations to the in vitro assay containing 100 µM [γ32-P] ATP and histone H1. The results are shown in FIG. 2. Inhibition increased progressively with increasing P5 concentration in both complexes (Compare FIGS. 2A, 2B with 2C, 2D). Although Cdk5/P25 activity is significantly greater, the kinetics of inhibition was similar for both enzyme complexes. For example, at 0.05 µM P5, activities of both Cdk5/P35 and Cdk5/P25 were inhibited at about 30%, (compare lanes 2 in FIGS. 2B and 2D) while 1.2 µM P5 virtually eliminated activity in both cases (compare lanes 7, FIGS. 2B and 2D). Under these in vitro conditions, P5 inhibition was not specific for Cdk5/P25.

Example 4

P5 Inhibition of Cdk5/P25 Without Affecting Endogenous Cdk5/P35

This example shows P5 inhibits Cdk5/P25 activity without affecting endogenous Cdk5/P35 activity in cortical neurons.

Figure 3A:
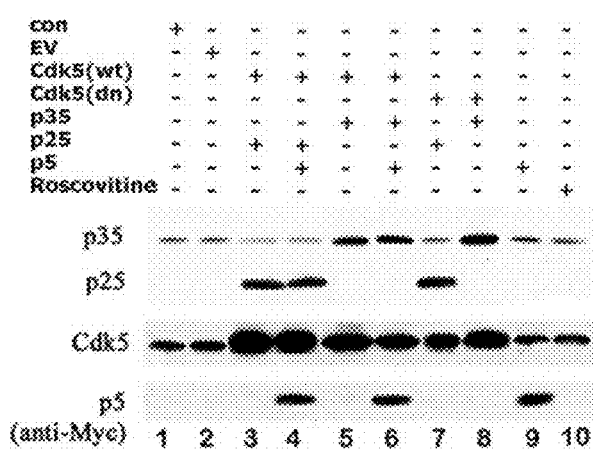
FIGS. 3A-3D illustrate that P5 inhibits Cdk5/P25 activity without affecting endogenous Cdk5/P35 activity in cortical neurons. To determine the effect of P5 on Cdk5/P35 and Cdk5/P25 activity in infected neurons, E-18 rat cortical neurons after 5 DIC were infected with different gene constructs using adenoviral vector as follows: co-infected with Cdk5/P25, Cdk5/P35, double-negative (dn) Cdk5/P25, dnCdk5/P35 or triply infected with GFP-myc-P5, except for cells that were infected with GFP-myc-P5 alone, and one group of uninfected cells treated with 20 μM roscovitine as a control. After SDS-PAGE and Western analysis with the specific antibodies, the expression level of each of the constructs is shown in the digital image provided in FIG. 3A.
Figure 3B:
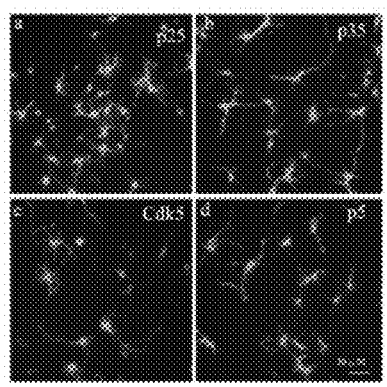
Figure 3C:
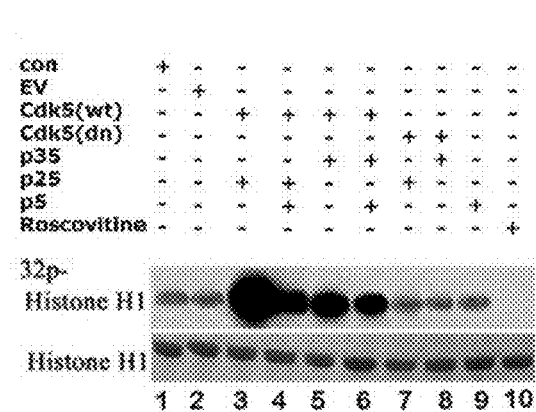

If specificity of P5 inhibition is not evident in vitro, is it present in cortical neurons? To address this question, E-18 rat cortical neurons were co-infected with Cdk5 and P5, P35 or PP5 in various constructs. The AdEasy based viral infection system, used to introduce the appropriate genes into cortical neurons, typically yielded approximately 60-70% efficiency (FIG. 3B). Western blotting with the appropriate antibodies was used to examine the expression of Cdk5, P35 and P25 genes in cortical neurons (FIGS. 3A and 3B). Neurons were infected at day 5 in culture (5-DIC) and lysates were harvested after 48 hours to ensure proper integration, infection rates and high expression levels. As seen in FIG. 3A, infected Cdk5 showed dramatically higher expression (lane 3-8) compared to controls (con), empty vector (EV) (lane 1, 2) and P5 only (lane 9). Infected P35 and P25 also showed robust increases in the amounts of expressed protein (lanes 5, 6 and 8 and lanes 3, 4, and 7, respectively). Endogenous P35 (lanes 1-4, 7, 9, and 10) was expressed at much lower levels when compared to endogenous Cdk5, (lane 1, 2, 9, 10) while P25 showed no endogenous expression. To determine the specificity of P5 inhibition in cortical neurons, Cdk5 immunoprecipitates were prepared from each infected culture and kinase activity was assayed in vitro (FIG. 3C radioautographs, 3D pad assay). Endogenous basal levels of Cdk5 activity were shown in control (non-infected cells) and vector (EV) infected neurons (lanes 1, 2). Neurons infected with Cdk5/P25 showed remarkably high activity (lane 3); when co-infected with P5, however, activity decreased more than 90% (p<0.01 compare lane 4 with lane 3). Activity in neurons co-infected with Cdk5/P35, though much lower than Cdk5/P25, exhibited only 10-20% inhibition when co-infected with P5 (p>0.05 compare lane 6 with 5). These results suggest that P5 affects Cdk5/P35 activity within infected neurons as much as it inhibits Cdk5/P25 activity. Cells infected only with P5, exhibited no reduction in activity (compare lanes 1 and 2 with lane 9). Complete inhibition, however, occurred in the presence of roscovitine (lane 10) suggesting that P5 does not inhibit endogenous Cdk5/P35 activity. Cells infected with dnCdk5, as negative controls, exhibit endogenous levels of activity (lanes 7, 8). Summarizing, P5 does not inhibit Cdk5/P35 activity in neuronal cells to the same extent as Cdk5/P25.

Example 5

P5 Inhibition of Aβ-Mediated Cdk5/P25 and Aβ-Mediated Tau Hyperphosphorylation

This example shows P5 inhibits Aβ-mediated Cdk5/P25 hyperactivity and Aβ-mediated tau hyperphosphorylation.

Amyloid plaques and neurofibrillary tangles, pathological hallmarks of several neurodegenerative disorders, are linked to deregulated Cdk5 and neuronal death. According to one model, β amyloid, being toxic, may evoke abnormal calcium influx into neurons which activates calpains. These proteases cleave P35 to P25 which forms a more stable and hyperactive complex with Cdk5. Hyperactivation of Cdk5, leads to the aberrant phosphorylation of tau and neurofilaments in a number of neurodegenerative diseases including AD and ALS. For example, primary cortical neurons, when treated with Aβ1-42 are induced to form Cdk5/P25 complexes, hyperactive Cdk5 activity, hyperphosphorylation of tau, and neuronal apoptosis. To determine whether P5 will inhibit endogenous tau phosphorylation induced by Aβ treatment in cortical neurons, 7 day old cortical neurons, infected with empty vector (EV) or with P5 were treated with Aβ for 6 hours, lysed and prepared for Cdk5 immunoprecipitation and kinase assay. The data are shown in FIG. 4. Aβ treatment causes an approximate 3-fold increase in endogenous Cdk5 activity as visualized by histone H1 phosphorylation (FIG. 4A, panel 5, lane 2; FIG. 4B). Infected P5, however, dramatically reduced Cdk5 activity in the Aβ treated neurons to basal levels (lane 3). Western blot assays of whole cell lysates from similarly transfected cortical neurons treated with Aβ revealed an up-regulation of the expression of P25 (FIG. 4A, panel 3, lanes, 2-4). The increased P25 expression was correlated with an increased level of endogenous tau phosphorylation at residues S199/202 as detected by two different phospho-tau antibodies, AT8 and p-Ser 199/202 (FIG. 4C, panels 1 and 2, lane 2; FIG. 4D), while infection of P5 inhibited the Aβ-mediated tau hyperphosphorylation restoring it to basal levels (lane 3).

In order to confirm that tau was hyperphosphorylated by Cdk5, and not by other kinases, a Cdk5 inhibitor, roscovitine, was used to co-treat cells with Aβ. The results showed that the tau phosphorylation was significantly inhibited ($p<0.01$) (FIG. 4C, panels 1 and 2, lane 4; FIG. 4D). To confirm these results, Tau1 antibody was used to detect the non-phosphorylated tau S199/202 (FIG. 4C, panel 3). The results showed that the non-phospho-tau was decreased in Aβ treated cells (lane 2, compare with lanes 3 and 4). Tau antibodies p-Ser404, PHF antibody AT180 (recognizes p-Thr231) and p-Ser422 antibodies were used to observe whether P5 affects other tau phosphorylation residues (FIGS. 4E, 4F). The results showed that Aβ-induced tau hyperphosphorylation can be detected with the above three antibodies in cortical neurons. P5 significantly inhibits tau phosphorylation at S404 and T231 (FIG. 4E panels 1 and 2, lane 3 compared with lane 2; FIG. 4F) ($p<0.01$), while the slight decrease of tau phosphorylation at the Ser422 site, is not significant (FIG. 4E, panel 3, lane 3 compared with lane 2) ($p>0.05$). However, roscovitine significantly inhibits tau phosphorylation at Ser422 site (panel 3, lane 4 compared with lane 2) ($p<0.05$). Tau 5 recognizes total tau, nonphosphorylated as well as phosphorylated. Summarizing, P5 effectively inhibits Cdk5 phosphorylation of tau sites identified in PHF tau that characterizes abnormal tangles in AD.

Example 6

P5 Inhibition of Aβ-Mediated Neuronal Apoptosis

This example shows that P5 inhibits Aβ-mediated neuronal apoptosis.

Figure 5A:
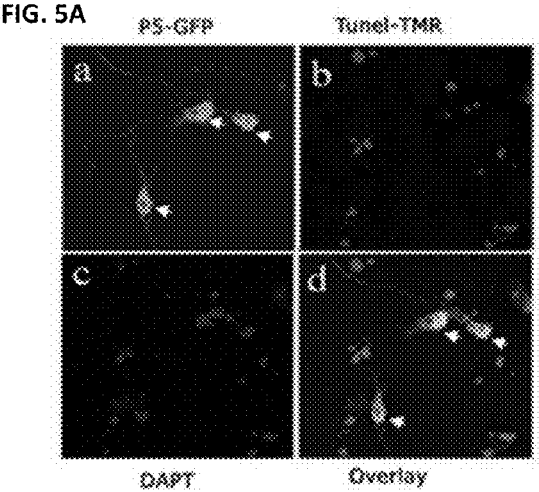
FIGS. 5A-5D illustrate that Aβ-induced apoptosis is prevented in the presence of P5. E-18 cortical neurons grown for 3 days were transfected with or without green fluorescent protein (GFP)-P5. After 24 hours they were treated with Aβ for 6 hours, fixed and prepared for a TUNEL apoptosis assay. As illustrated in digital images provided in FIG. 5A, P5 transfected neurons expressing GFP (panel a) are prevented from undergoing apoptosis as seen in the overlay in panel d.
Figure 5C:
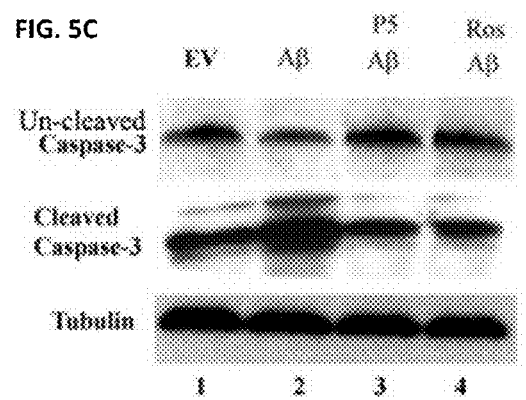
Figure 5B:
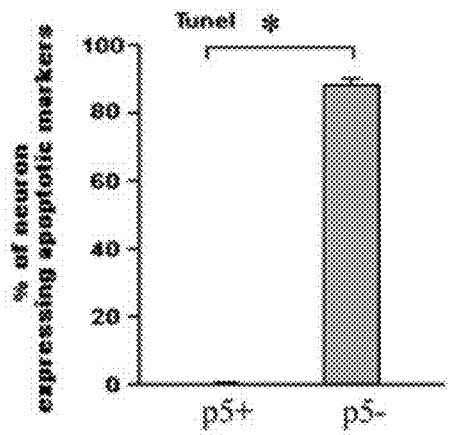
Figure 5D:
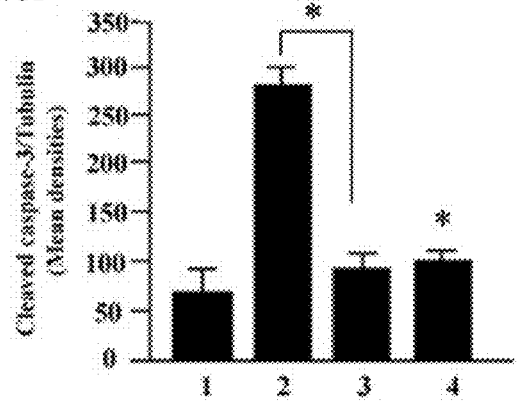

To determine whether P5 inhibited neuronal apoptosis induced by Aβ, primary cortical neurons (5 days in culture (DIC)) were transfected with P5-GFP using Lipofectamine 2000. After 24 hours, cells were exposed to Aβ for 6 hours. The neurons were fixed and subjected to TUNEL staining, while P5 was visualized by (green fluorescent protein) GFP. P5 clearly inhibited Aβ-mediated neuronal apoptosis in as much as the only TUNEL negative neurons were those infected with P5 (FIG. 5A, panels a-d arrows), whereas non-transfected neurons showed TUNEL positive and fragmented nuclei (FIG. 5A, panels a-d). The data are quantified in FIG. 5B. More than 85% of nontransfected neurons were apoptosis positive. To confirm these results, an independent method of assaying for cell death, the expression of cleaved caspase-3, was used. Cortical neurons infected with or without P5 and treated with Aβ for 6 hours were assayed for cleaved caspase 3 by Western blot analysis (FIG. 5C). As seen in the Figure, the infection of EV and treatment with Aβ caused elevated expression of cleaved caspase-3 (FIG. 5C, panel 2, lane 2), which was inhibited in those cells infected with P5 (FIG. 5C, panel 2, lane 3); cleaved caspase-3 expression was reduced to control EV levels. To confirm that the effect was mediated by activated Cdk5, cells treated with roscovitine exhibited reduced levels of cleaved caspase-3 comparable to that seen with P5 infection (FIG. 5C, panel 2, lane 4). To confirm the result, anti-caspase 3 was used to detect uncleaved caspase 3. The uncleaved caspase 3 is lower in Aβ-induced cells (FIG. 5C, panel 1, lane 2 compared with control cells) and the cells treated with P5 or roscovitine (FIG. 5C, panel 2, lane 1, 3, and 4). The data are quantified in FIG. 5D. In an independent apoptosis assay, caspase-3 cleavage assay, pre-treatment with P5 significantly rescued cortical neurons from apoptosis ($p<0.01$).

Example 7

P5 Inhibition of Cdk5 Hyperactivity Induced by Aβ

This example shows P5 at low doses inhibits Cdk5 hyperactivity induced by Aβ.

Figure 6A:
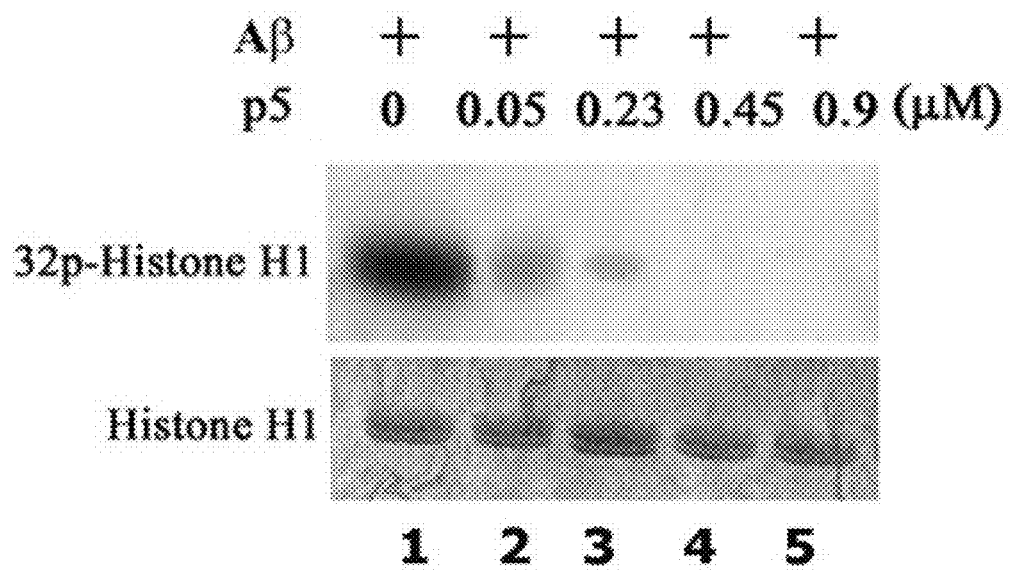
FIGS. 6A and 6B show that P5 at low concentrations inhibits Cdk5/P25 activity induced by Aβ in cortical neurons. Seven DIC cortical neurons were treated with 10 μM Aβ1-42 or PBS for 6 hours and the harvested cells were lysed for Cdk5 immunoprecipitation using anti-Cdk5 antibody. Immunoprecipitates were then used as enzyme in in vitro kinase assays with increasing concentrations of P5 peptide. The top panel of FIG. 6A is the autoradiograph and the bottom panel shows the corresponding Coomassie-stained histone H1 bands. High levels of induced activity are rapidly inhibited by the addition of P5.

To determine the minimum dose at which the P5 peptide is an efficient inhibitor of Cdk5/P25 hyperactivity under physiological conditions, cortical neurons were treated with Aβ1-42 to induce the expression of P25 and Cdk5 hyperactivation, Cdk5 immunoprecipitates were prepared and the effect of different concentrations of P5 was evaluated (FIG. 6). The results show that 0.05 µM of P5 peptide decreased Aβ1-42-induced Cdk5 hyperactivity more than 70% (compare lane 2 to lane 1) ($p<0.01$) and at P5 concentrations of 0.45 µM or above, activity was totally eliminated (lanes 4 and 5). These results indicate that P5 is effective at very low doses in successfully reducing Aβ-induced Cdk5/P25 activity.

Example 8

P5 Infection does not Inhibit Endogenous Cdk Activities

This example shows P5 infection does not inhibit endogenous Cdk activities.

If P5 is to function as an effective systemic therapeutic agent it should target brain neurons without secondarily affecting organs and tissues enriched in cycling cells (e.g., immune system, gastrointestinal tract, skin) containing cyclin dependent kinases such as Cdk2, Cdk4 and Cdk6. All, like Cdk5, are inhibited by roscovitine and may be sensitive to P5. To determine whether P5 inhibits other Cdks, three groups of HEK293 cells were prepared, a control group infected with vector only, a group treated with 20 µM roscovitine and a third group of cells infected with a cMyc-tagged P5. Aliquots of cell lysates from each group were subjected to immunoprecipitation respectively, using Cdc2, Cdk2, Cdk4, and Cdk6 antibodies. The respective immunoprecipitates were assayed for kinase activity (FIG. 7). The expression of infected P5 (myc) and endogenous cyclin kinase was detected by anti-Myc and the respective antibodies, (FIGS. 7A-7D, panels 1, 2). The activity data seen in panel 3 show varying degrees of inhibition by roscovitine whereas infected P5 exhibited no inhibition in all cases ($p>0.05$, compared all lane 3 with lane 1). The activity data, based on a kinase pad assay were quantified as the mean and standard error of three independent experiments in FIG. 7E. These results indicate that P5, a derivative of the P35 regulator, fails to inhibit cyclin dependent kinases in proliferating cells, although each is inhibited to varying degrees by roscovitine. It suggests that specificity of P5 inhibition of Cdk5/P25 resides in its interaction with the regulator while roscovitine affects the catalytic site (ATP binding site) in the cyclin kinase family. As a therapeutic agent used systemically, these data suggest that P5 may effectively protect stressed neurons without affecting proliferating tissues and producing secondary side effects.

Figure 6B:
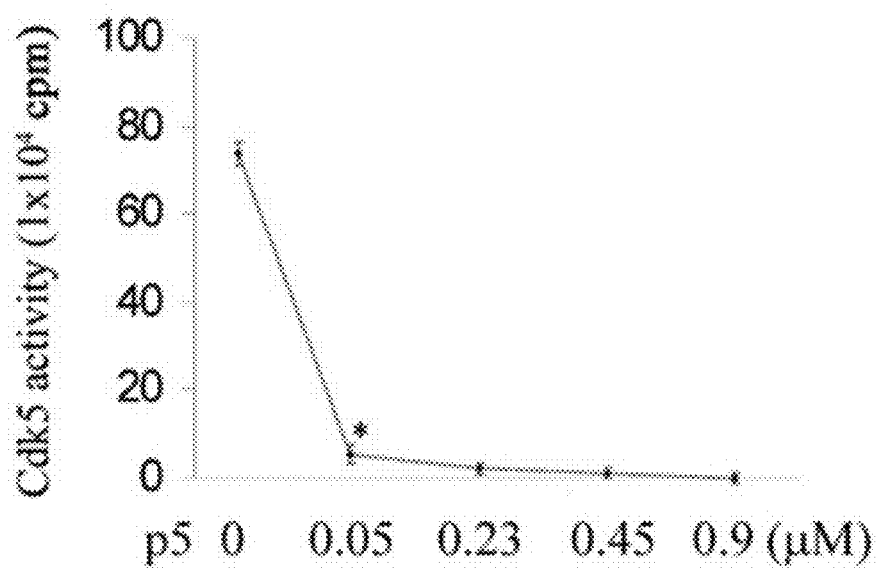
Figure 8A:
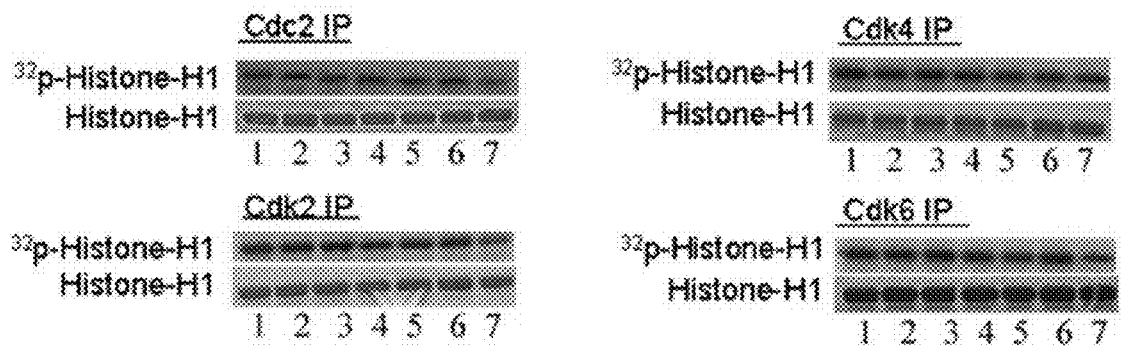
FIGS. 8A and 8B show that high concentrations of P5 do not inhibit activities of cell cycle Cdks. A dose-dependent analysis shows the effect of P5 on Cdk activities in vitro. Non-treated and non-transfected HEK293 cell lysates were subjected to immunoprecipitation using anti Cdc2, Cdk2, Cdk4, and Cdk6 antibodies. The immunoprecipitations were used for standard kinase pad assays in the presence of increasing concentrations of P5 peptide (0.05-1.8 µM).
Figure 8B:
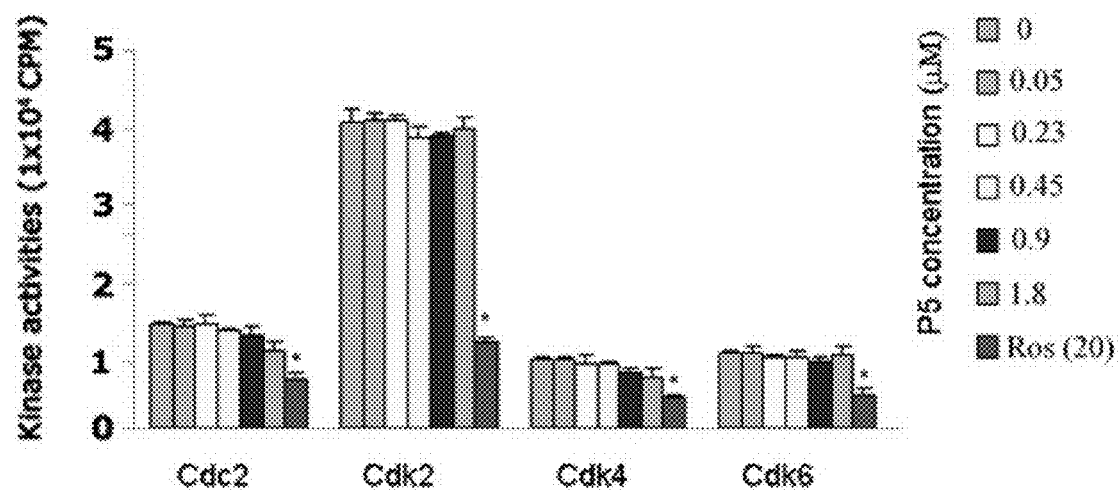

It is possible that the response to P5 is dose-dependent among cyclin dependent kinases, with Cdk5 showing maximum sensitivity since P5 derived from P25, is more likely to competitively inhibit P25 binding to Cdk5 at lower doses. To test the possibility that higher doses of P5 might inhibit other cyclin dependent kinases, four sets of HEK293 cells were immunoprecipitated with antibodies specific to Cdc2, Cdk2, Cdk4, and Cdk6, respectively. The IPs were then used as enzyme in kinase pad assays in vitro to which different concentrations of P5 peptide were added ranging from 0 to 1.8 micromolar (a dose-dependent study) (FIGS. 8 A, 8B), similar to P5 concentrations used for Cdk5 (See FIGS. 2 and 6B). The results, shown in autoradiographs in FIG. 8A suggest minimal inhibition of Cdc2 and Cdk4 activities at the highest concentration (1.8 µM). Roscovitine, in lane 7, shows a significant effect for all kinases ($p<0.01$). The pad assay data are quantified in FIG. 8B and confirm the conclusion that the cell cycle kinases showed a marked roscovitine inhibition with virtually no inhibition by P5, even at its highest concentration ($p>0.05$). Cdk5 activity, on the other hand, was virtually abolished at the lowest concentration, 0.05 µM P5 (FIG. 6B). Cdk5/P25 was selectively inhibited by P5 while related cyclin dependent kinases are unaffected even in actively cycling cells. It suggests that if P5 shows a high degree of specificity, affecting post-mitotic brain neurons without affecting actively proliferating cells.

Example 9

P5 Interaction of P35 with Tubulin

This example shows P5 interaction of P35 with tubulin may account for P5 specificity in cortical neurons.

Figure 3D:
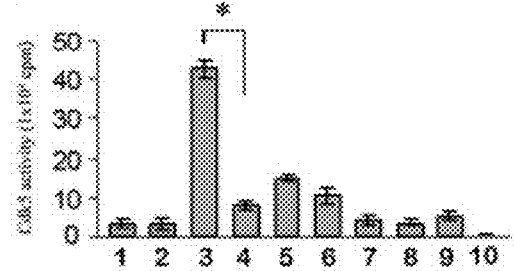

The data presented in FIG. 2 show that P5 inhibition is non-specific in vitro; it inhibits both Cdk5/P35 and Cdk5/P25 activities equally. Specificity is shown in cells, however, where P5 inhibited Cdk5/P25 activity more so than Cdk5/P35 activity in cortical neurons (FIGS. 3C and 3D, lane 3, 4, 5, and 6). A structural difference between the two activators is that P25 is a truncated version of P35 and lacks the myristolated P10 N-terminal domain of the intact P35. The P10 region is responsible for interaction of P35 with several cellular proteins such as importins, Munc18, calmodulin, microtubules, and protein kinase CK2. Microtubules, for example, bind P35 due to its P10 domain whereas they do not interact with the P25 due to the loss of P10 region of P35 truncated fragment. This suggests that P10 in P35 is involved in microtubule interaction. Microtubule binding to P35 competes with P5 preventing it from interacting with Cdk5 in the Cdk5/P35 complex. Cells, proteins like microtubules, binding to P35, may prevent P5 binding to Cdk5 in the Cdk5/P35 complex.

Figure 9A:
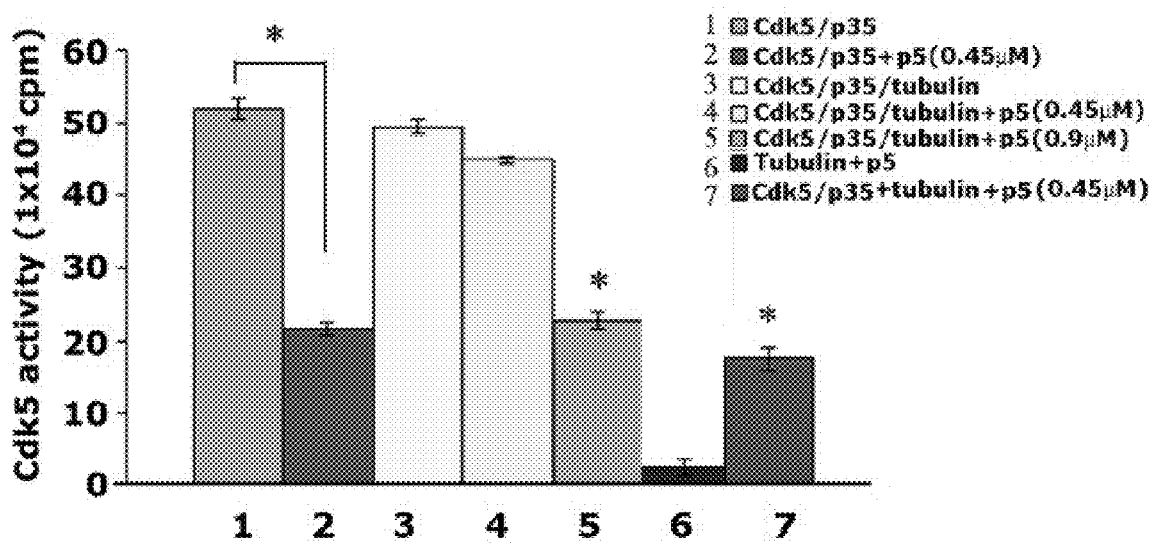
FIGS. 9A and 9B illustrate that polymerized tubulin protects Cdk5/P35 activity from P5 inhibition in vitro. Active Cdk5/P35 and Cdk5/P25 were pre-incubated with tubulin in PEM buffer supplemented with 1 mM GTP at 35° C. for 45 minutes to 1 hour (under conditions to promote polymerization). P5 at 0.45 or 0.9 µM was added and the mixture was then subjected to in vitro kinase assay. Quantification of Cdk5/P35 (FIG. 9A) and Cdk5/P25 (FIG. 9B) activities showed that P5 inhibits pre-incubated Cdk5/P25 activity approximately 50% (compare FIGS. 9B, 3 and 4) but has no effect on pre-incubated Cdk5/P35 activity (compare FIGS. 9A, 3 and 4). At a higher concentration of P5 (0.9 µM), both kinase complexes are inhibited equally (compare 5 in FIG. 9A and FIG. 9B). The importance of polymerization during pre-incubation is seen in lane 7 of both FIGS. 9A and 9B; in the presence of unpolymerized tubulin, P5 inhibits both kinases equally. The concentrations of Cdk5/P35 and Cdk5/P25 were matched to exhibit equal activity. Data represent mean±SE of three studies. (*p<0.01)
Figure 9B:
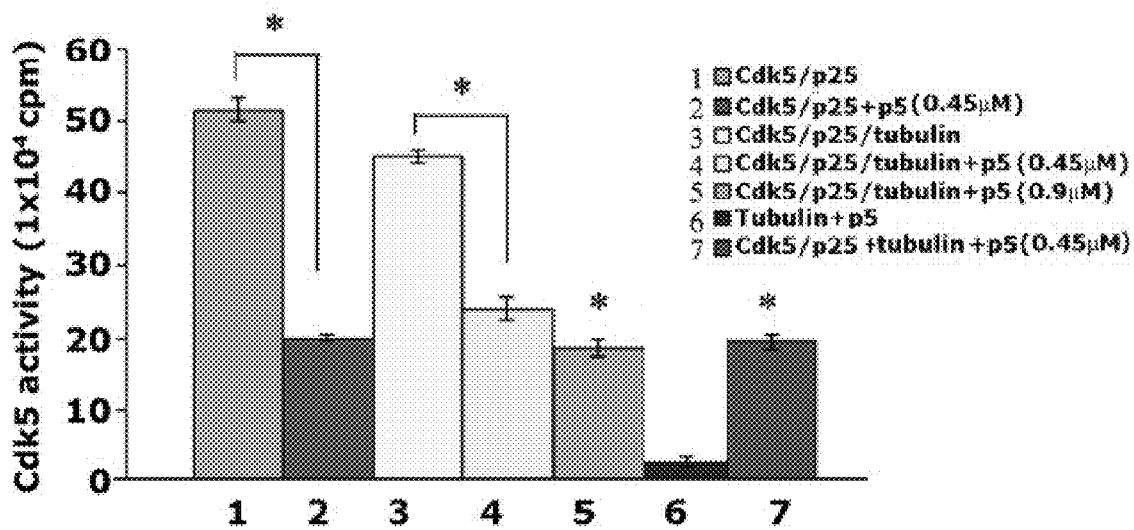

To further explore this possibility, β-tubulin (which is enriched in neurons) was used to perform a study in vitro to mimic P35 interactions in cells. Cdk5/P35 and Cdk5/P25 active kinases were pre-incubated with β-tubulin (Cdk5 kinase:tubulin=1:100) respectively at 35° C. for 45 minutes to 1 hour under conditions that would promote tubulin polymerization, followed by a Cdk5 kinase assay with/without the addition of P5. The results showed that Cdk5/P35 activity was not inhibited by 0.45 µM P5 after pre-incubation with β-tubulin (FIG. 9A, lane 4 compare to lane 1) ($p>0.05$). Cdk5/P25 activity, however, was inhibited 60% after pre-incubation at the lower P5 concentration (0.45 µM) (FIG. 9B, lane 4 compared with lane 1) ($p<0.01$). This suggests that Cdk5/P35 activity is protected from P5 by tubulin polymerization perhaps as a consequence of microtubule binding the Cdk5/P35 complex, making it less accessible to P5. At double the concentration of P5 to 0.90 µM, however, both Cdk5 complexes were inhibited (FIGS. 9A, B, lanes 5 compared with lane 1) ($p<0.01$). To confirm the role of tubulin polymerization, it was shown that in the absence of pre-incubation (unpolymerized), P5 inhibited both Cdk5/P35 and Cdk5/P25 activities equally at 0.45 µM (FIGS. 9A, 9B, lanes 7 compared with lane 1) ($p<0.01$). Albumin was used as a control protein in the same conditions and showed no differential effect of P5 on both Cdk5/P35 and Cdk5/P25 activities. These results suggest that specificity of P5 inhibition in cortical neurons probably results from P35 binding to proteins like microtubules to form a multimeric complex that sequesters the Cdk5/P35 complex from P5. On the other hand, P25, lacking the P10 domain, fails to bind these proteins, and P5 readily binds with Cdk5 in the Cdk5/P25 complex to inhibit activity.

The present results indicate that Cdk5 and its deregulation is a principal "player" responsible for tau pathology, neurofibrillary tangle (NFT) accumulation and cell death in AD. Several lines of evidence are consistent with this hypothesis. Cdk5 is stabilized and hyperactivated when complexed with P25. Neuronal stress converts P35 to its truncated form P25 by activating calpain, a calcium dependent protease, resulting in long term accumulation of P25, a major factor in the formation of hyperactivated Cdk5. Consistent with this, the ratio of P25 to P35 has been noted to be significantly higher in AD brains than in control brains, particularly in frontal cortex, although other laboratories report either a decrease in P25 or no evidence of an increased P25:P35 ratio in AD brains.

Nevertheless, overexpression of P25 in cultured neurons leads to cytoskeletal disruption, hyperphosphorylated tau, and apoptotic cell death. Cdk5 activity is deregulated in hippocampal neurons by Aβ fibrils resulting in the activation of Cdk5 and hyperphosphorylation of tau.

Probably because of its multifunctional role in the nervous system, aberrant Cdk5/P25 activity looms as a major factor in neurodegenerative disorders. This suggests that inhibitors of Cdk5 activity may be effective candidates for therapeutic development. Although several potent chemical inhibitors of Cdk5 have been identified and studied, most compete with ATP at the catalytic binding site. Accordingly, these compounds are relatively non-specific since other cyclin-dependent kinases, (as well as other kinases) are equally dependent on ATP binding. CIP, a 125 amino acid truncated peptide derived from P35, specifically inhibited Cdk5/P25 activity and significantly decreased hyperphosphorylation of tau and apoptosis induced by Aβ treatment in both HEK293 cells and cortical neurons. An effective therapeutic drug, however, should be much smaller to increase absorption efficiency (particularly across the blood-brain barrier) after injection or oral administration.

Here several truncated peptides derived from CIP were tested. P3 and P5 (only 24 residues) were identified as more effective inhibitors of Cdk5/P25 activity than CIP in vitro. Furthermore, P5 rescued cortical neurons from Aβ toxicity, tau pathology and cell death. At low doses it specifically inhibited Cdk5/P25 activity without affecting endogenous Cdk5/P35 activity in cortical neurons. At higher doses the activities of closely related Cdk kinases, such as Cdc2, Cdk2, Cdk4 and Cdk6 in proliferating HEK 293 cells were unaffected by P5. Although both complexes are inhibited equally by P5 in vitro, it is noteworthy that specificity of inhibition is displayed within cells; in cortical neurons hyperactive Cdk5/P25 is more effectively inhibited by P5 than the normal endogenous Cdk5/P35 complex. Though the factors responsible for P5 specificity in cortical neurons are not understood, it is critical to the therapeutic potential of P5. One theory is that the P10 myristolated N-terminal domain of P35, absent in P25, determines the specificity of P5 inhibition in cortical neurons. The P10 interaction in vivo with other cellular proteins such as tubulin (microtubules) and calmodulin may protect the activity of the Cdk5/P35 complex (and not the Cdk5/P25 complex) from P5 inhibition.

In FIG. 9, the addition of 0.45 µM of P5 had no effect on Cdk5/P35 following pre-incubation of the Cdk5/P35 complex with tubulin. In contrast, under Cdk5/P25 was inhibited under identical conditions. Without pre-incubation, however, P5 inhibited both complexes equally; P35 interaction with soluble tubulin did not prevent P5 inhibition. These data suggest that in cortical neurons, the relatively high affinity of P35 to microtubules sequesters the Cdk5/P35 complex from P5, interfering with P5 binding to Cdk5. The important message is that in cortical neurons, P5 inhibits the hyperactive Cdk5/P25 complex responsible for neuronal pathology without affecting the activity of the endogenous, functionally dependent Cdk5/P35.

P5 has been identified and characterized as a small, more readily diffusible peptide which specifically inhibits Cdk5/P25 activity at low doses, does not affect endogenous Cdk5/P35 essential for neuronal development and function, does not inhibit related Cdks in proliferating cells (hence would have significantly reduced side effects) and rescues neurons from Aβ toxicity, tau hyperphosphorylation and cell death.

Example 10

TFP5 In Vitro Inhibition of Cdk5/P25 and Cdk5/P35

This example shows TFP5 inhibition of both Cdk5/P25 and Cdk5/P35 activities in vitro.

Figure 17:
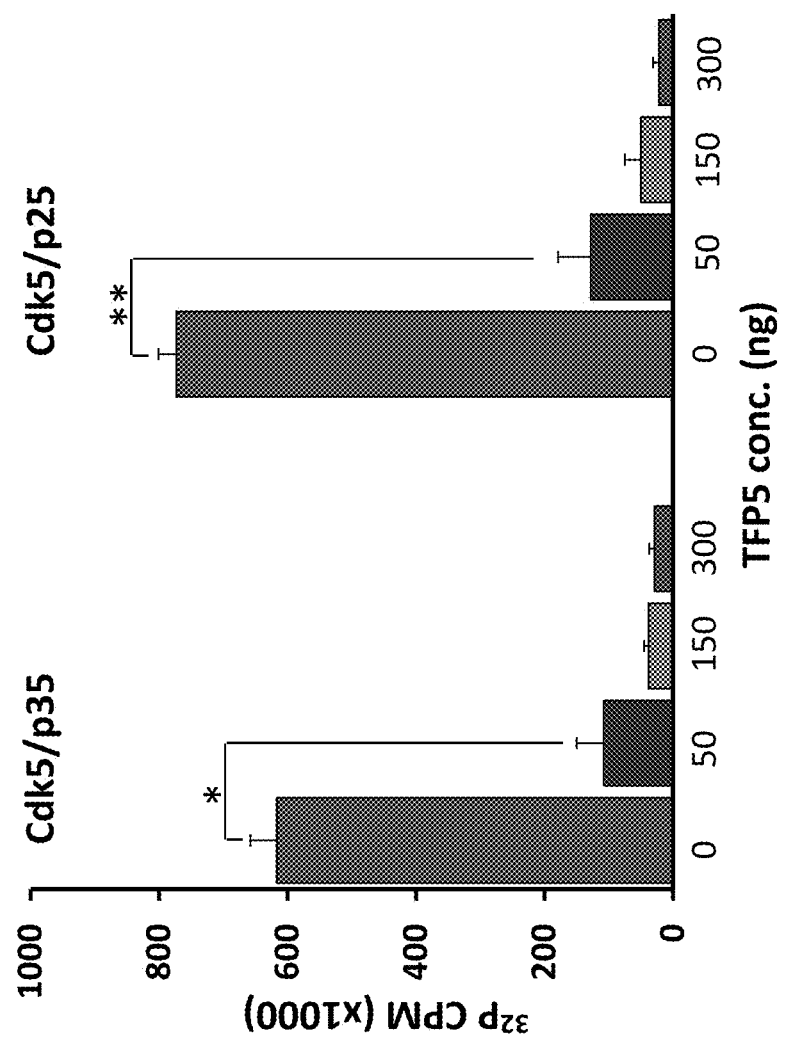
FIG. 17 is a bar graph demonstrating that in vitro, both Cdk5/p35 and Cdk5/p25 activities are significantly decreased by TFP5 at a concentration of 0.05 ng. Data represent means of four independent experiments with error bars representing SEM (*p≤0.05, **p≤0.001).

P5, a 24 amino acid peptide derived from Cdk5 regulator p35, was modified by conjugating it with TAT PTD at the C-terminal end and with FITC (using a GGG linker) at the N-terminus to produce a fluorescent (FITC-labeled) TFP5 (SEQ ID NO: 2) peptide. In a dose-dependent kinase assay the effective inhibitory concentration of TFP5 for both the Cdk5/P25 and Cdk5/P35 complexes was evaluated. His-P5 peptide was added at different concentrations to the in vitro assay containing 100 µM [γ32-P] ATP and histone H1. The results are shown in FIG. 17. Both Cdk5/p35 and Cdk5/p25 activities are significantly decreased by TFP5 at a concentration of 0.05 ng. Under these in vitro conditions, P5 inhibition was not specific for Cdk5/P25. Data represent means of four independent experiments with error bars representing SEM (*p≤0.05, **p≤0.001).

Example 11

TFP5 Inhibition of Cdk5/P25 Without Affecting Endogenous Cdk5/P35

This example shows that hyperactivation of Cdk5 induced by p25 is inhibited in vivo by TFP5 without affecting endogenous Cdk5/P35 activity in cortical neurons.

Due to their phenotypic similarity to p25 transgenic mice, the 5XFAD double transgenic mouse AD model was used to study the efficacy of TFP5 in reducing AD pathology and abnormal behavior. These 5XFAD mice over-express both mutant human amyloid precursor protein (APP695) with the Swedish (K670N, M671L), Florida (1716V), and London (V717I) Familial Alzheimer's Disease (FAD) mutations and human presenilin 1 (PS1) harboring two FAD mutations, M146L and L286V. These mice express high levels of amyloidgenesis beginning at 2 months of age, which is correlated with synaptic and behavioral dysfunction that becomes increasingly severe over a 12 month period; up-regulation of p25 and Cdk5 activity is noted at 3 months.

Figure 11A:
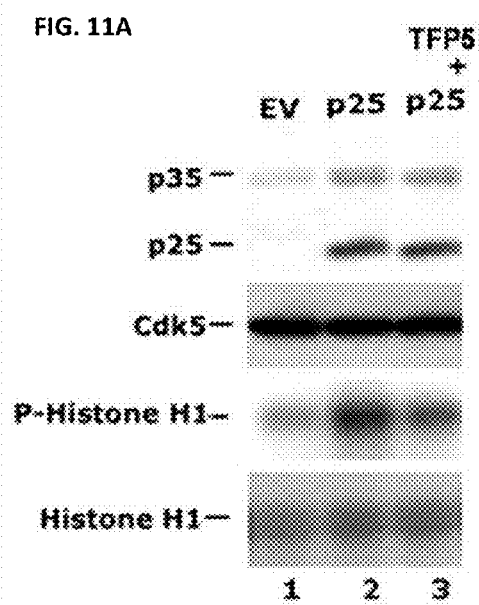
FIGS. 11A-11C illustrate that TFP5 treatment reduced hyperactivation of Cdk5 induced by P25. Cortical neurons from E18 rats were treated with 0.05 µM TFP5 and infected with and without GFP-P25 vector.
Figure 11B:
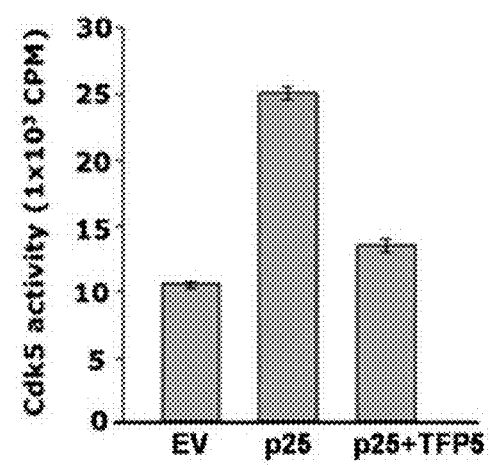
Figure 11C:
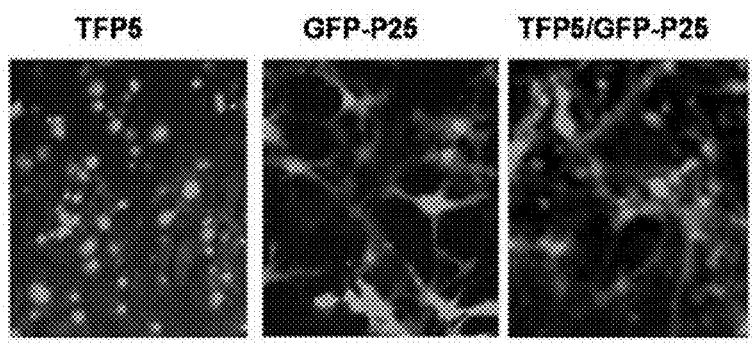

Cortical neurons from E18 rats were treated with 0.05 µM TFP5 and infected with and without GFP-P25 vector. FIGS. 11A and 11B show hyperactivation of Cdk5 upon P25 infection is reduced by TFP5 treatment. FIG. 11C illustrates the localization of TFP5 and P25 with FITC (fluorescein isothiocyanate) and GFP (green fluorescent protein), respectively. Thus, TFP5 entered and localized in the cells without any toxicity.

In separate experiments, kinase assays were performed on lysates of rat cortical neurons on day 7 in culture after transfection with either empty vector (EV) or p25 for 48 hours. Cells were treated with 0.05 µM TFP5, 2 hours post transfection and Cdk5/p35 and Cdk5/p25 activities were measured using histone as a substrate (FIG. 18A). Quantitation of the kinase activities shows significant reduction in Cdk5 activity in p25 transfected cells when treated with TFP5 but endogenous Cdk5/p35 activity was unaffected (FIG. 18B). Data represent mean of three independent experiments; SEM (*p≤0.05). FIG. 18C shows the Western blot analysis of p35, p25, Cdk5, AT8 (pTau), and total Tau on the lysate of cortical neurons performed after transfection with and without p25-RFP (red fluorescent protein). No p25 is observed in non-transfected cortical neurons (lane 2). Phospho-tau levels were elevated in p25 transfected to non-p25 transfected neuronal lysates. After TFP5 treatment; the phospho-tau level was reduced to that of non-transfected cells (compare lane 1, 2, and 3). Total tau antibody was used as a marker for equal loading. FIG. 18D is a digital image illustrating the localization of TFP5 and p25 with FITC and Red Fluorescent Protein (RFP), respectively, in cortical neurons.

Figure 13A:
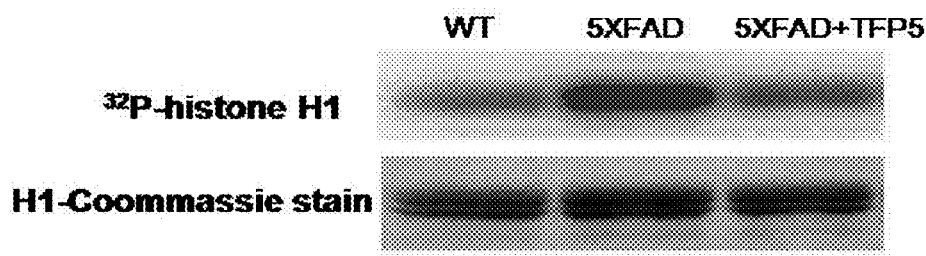
FIGS. 13A and 13B illustrate that TFP5 injection reduces hyperactivation of Cdk5 in the kinase activity 5XFAD mice. After i.p. injection of vehicle and TFP5 for three consecutive days, brain lysates were prepared from vehicle injected WT (wild-type), 5XFAD, and TFP5 injected 5XFAD mice.
Figure 13B:
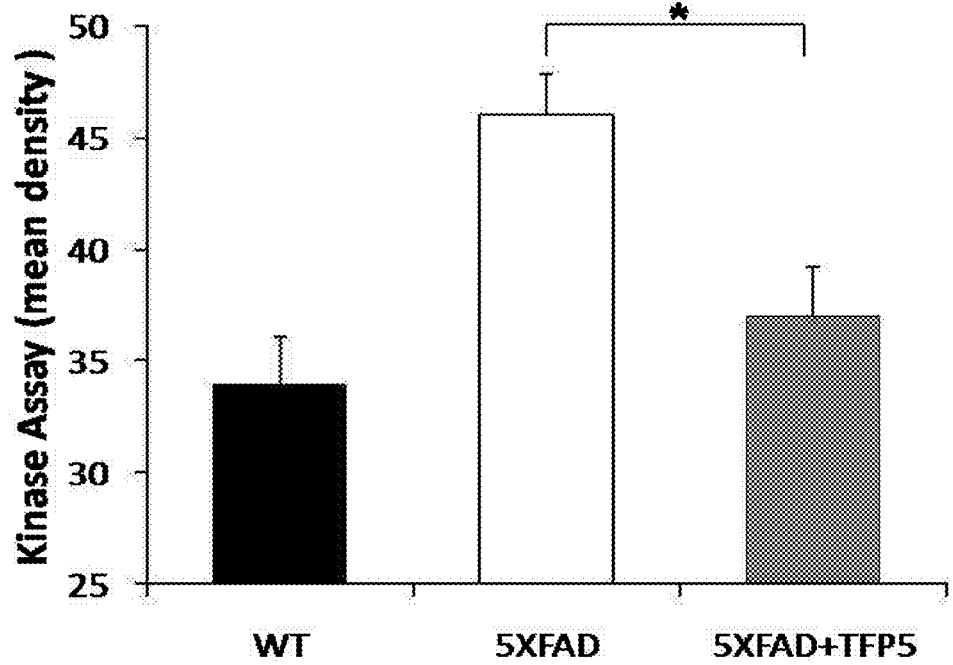

Further, brain extracts from treated and untreated 5XFAD animals show that TFP5 injection reduced activity of Cdk5 by both immunoprecipitation and kinase assay in both 6 month old (FIGS. 13A and 13B) and 12 month old mice.

These studies indicate ip-injected TFP5 (0.2 mM) crosses the BBB and localizes widely in different parts of the brain and other organs without any toxicity. Thus, TFP5 can inhibit hyperactivated Cdk5/P25 in vitro and in vivo, and is an excellent therapeutic candidate to rescue neurons from the debilitating onslaught of Aβ toxicity and hyperactivated Cdk5/P25 that characterizes some neurodegenerative disorders.

Example 12

TFP5 Crosses the Blood Brain Barrier

This example shows that TFP5 not only enters peripheral organs, but also crosses the blood brain barrier and localizes in different parts of the brain without any toxicity.

Figures 12A, 12B, 12C, 12D:
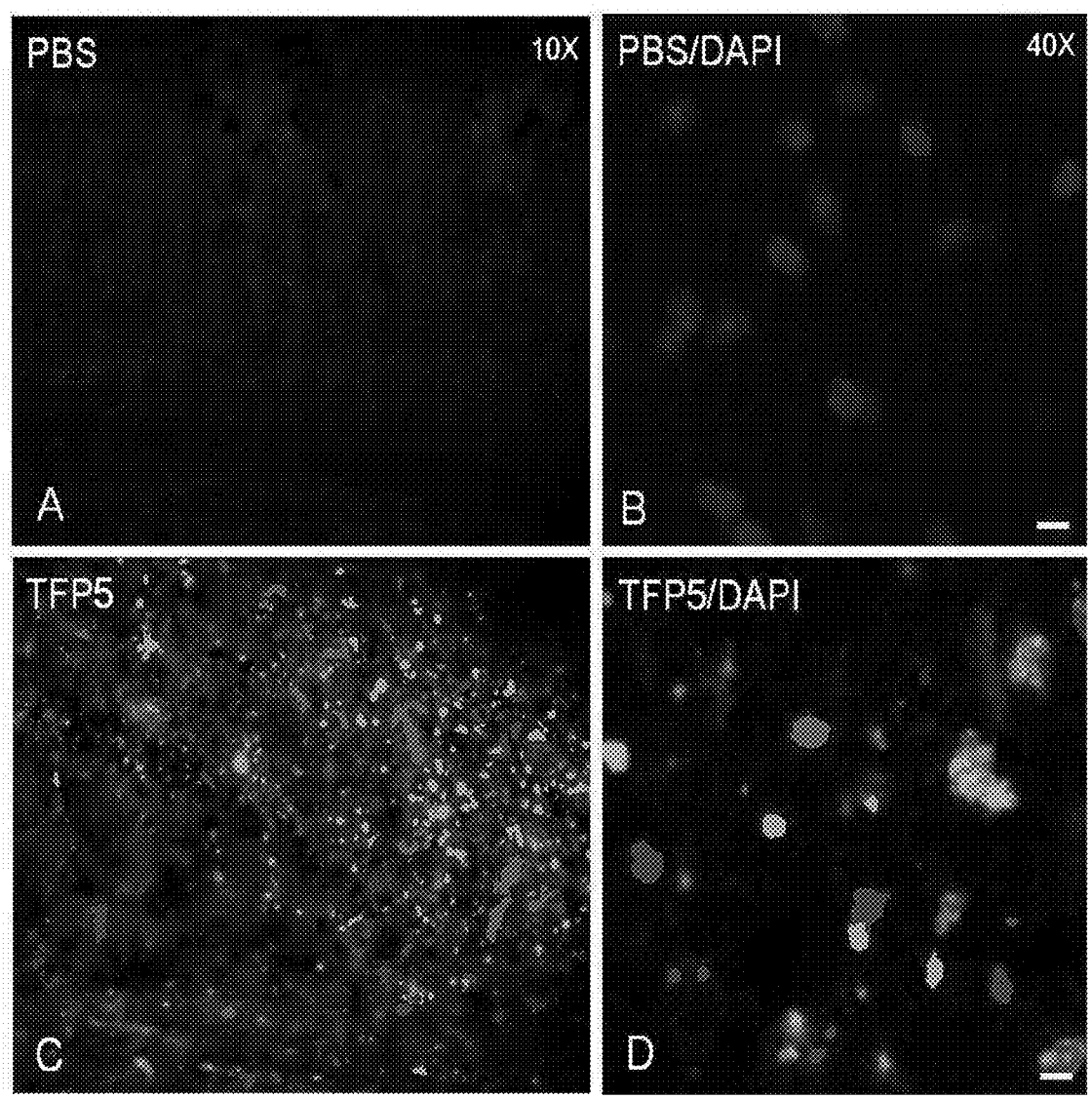
FIGS. 12A-12D include a series of fluorescent images illustrating that IP injection of TFP5 crosses the blood brain barrier and localizes in the brain. Parasagittal brain sections of six month old 5XFAD mice injected with vehicle (FIG. 12A) and TFP5 peptide in PBS injected FIG. 12C) for three consecutive days. FITC labeling indicates the presence of TFP5 in the cortex.
Figure 19:
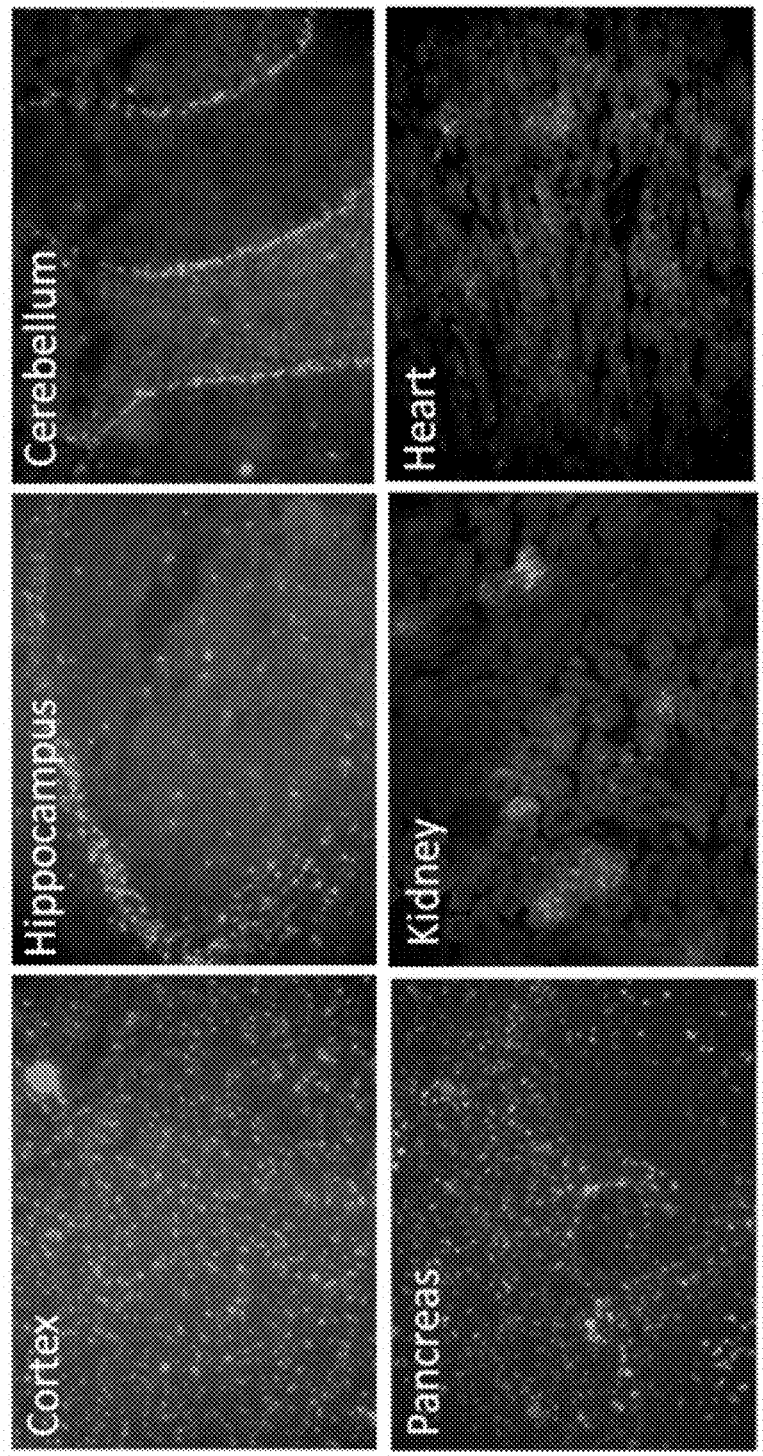
FIG. 19 is a series of digital images illustrating that TFP5 crosses the blood brain barrier after ip injection. Neuronal and non-neuronal tissues show FITC-labeled TFP5 localization at four days after a single ip injection (0.2 mM).

To determine if TFP5 crossed the BBB, parasagittal brain sections were obtained from six month old 5XFAD (amyloid precursor protein/presenilin) mice, or wild-type mice that were injected ip with vehicle (PBS; FIG. 12, panels A and B) or TFP5 peptide (0.2 mM, 50 mg/kg body weight) in PBS (phosphate buffered saline) injected (FIGS. 12C and 12D) for three consecutive days. As illustrated in FIGS. 12A-D, ip injection of TFP5 resulted in TFP5 crossing the BBB and localizing in different parts of the brain without resulting in cell death. In addition, neuronal and non-neuronal tissues show TFP5 localization at 4 days following a single ip injection (0.2 mM TFP5), as shown in Table 1 and FIG. 19.

TABLE 1

Distribution of TFP5 in various mouse tissues upon single injection

| Regions | Relative intensity of TFP5 expression Day 4 | Relative intensity of TFP5 expression Day 7 |
| --- | --- | --- |
| Brain: Cortex | ++++ | +++ |
| Hippocampus | +++ | ++ |
| Cerebellum | +++ | + |
| Pancreas | ++++ | +++ |
| Kidney | +++ | ++ |
| Heart | ++ | + |
| Liver | + | − |

++++ very high, +++ high, ++ moderate, + low, − none

Example 13

TFP5 Rescues Memory Deficits in the Y Maze Test

This example demonstrates that TFP5 treated 5XFAD mice show rescue of memory deficits in the Y maze test.

Figure 14:
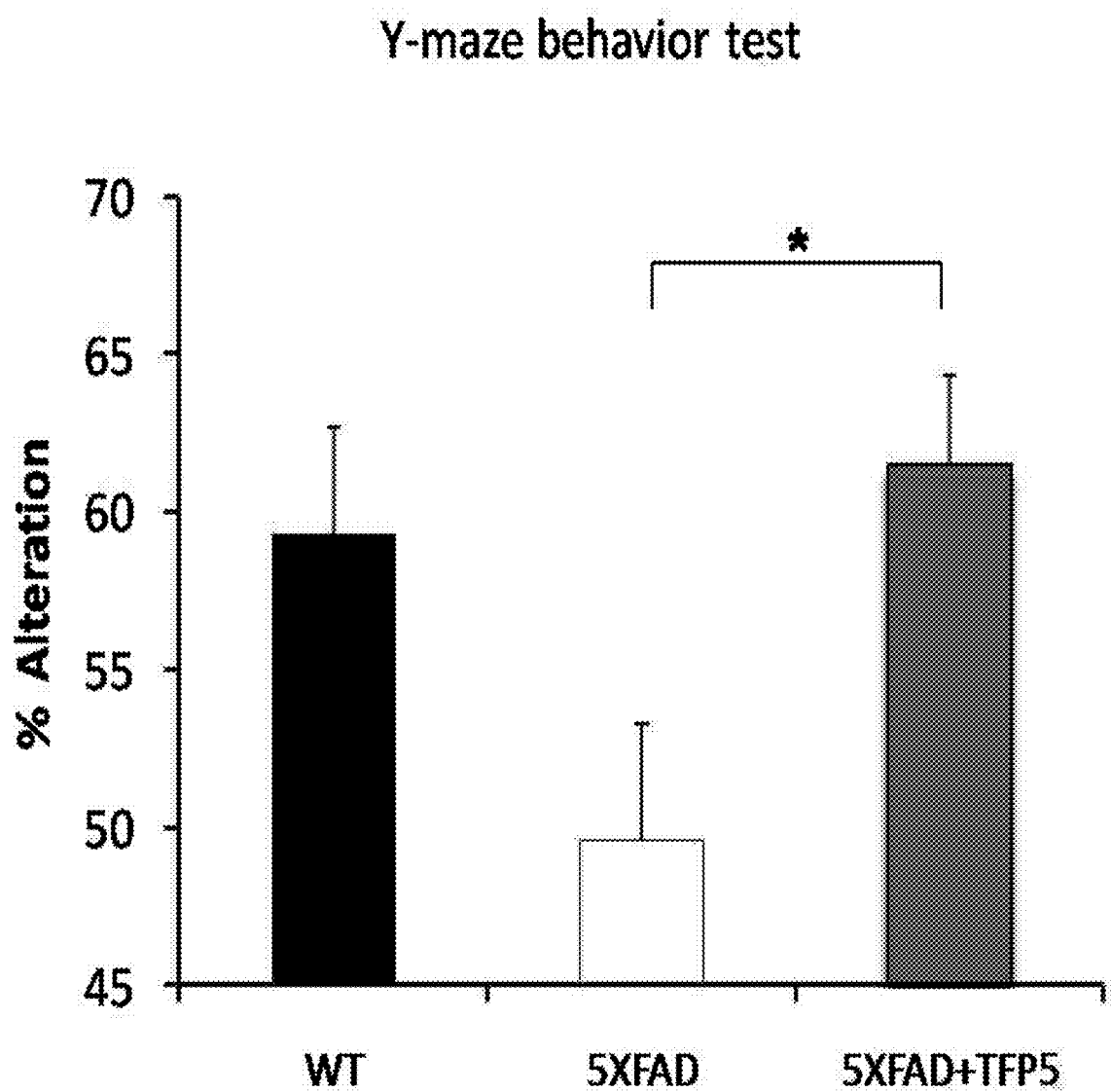
FIG. 14 is a bar graph illustrating that TFP5 injection rescues memory deficits in 5XFAD mice. Spatial working memory of 5XFAD mice and WT (wild-type) littermates were assessed by spontaneous alteration in the Y-maze after i.p. injection for three days. At six months of age, WT mice showed normal alteration performance in the Y-maze while 5XFAD performed poorly (less than 50%). After TFP5 injection, the 5XFAD mice recovered and showed normal alteration comparable to WT (n=3-12). Each column in the graph represents the mean±SEM.
Figure 20:
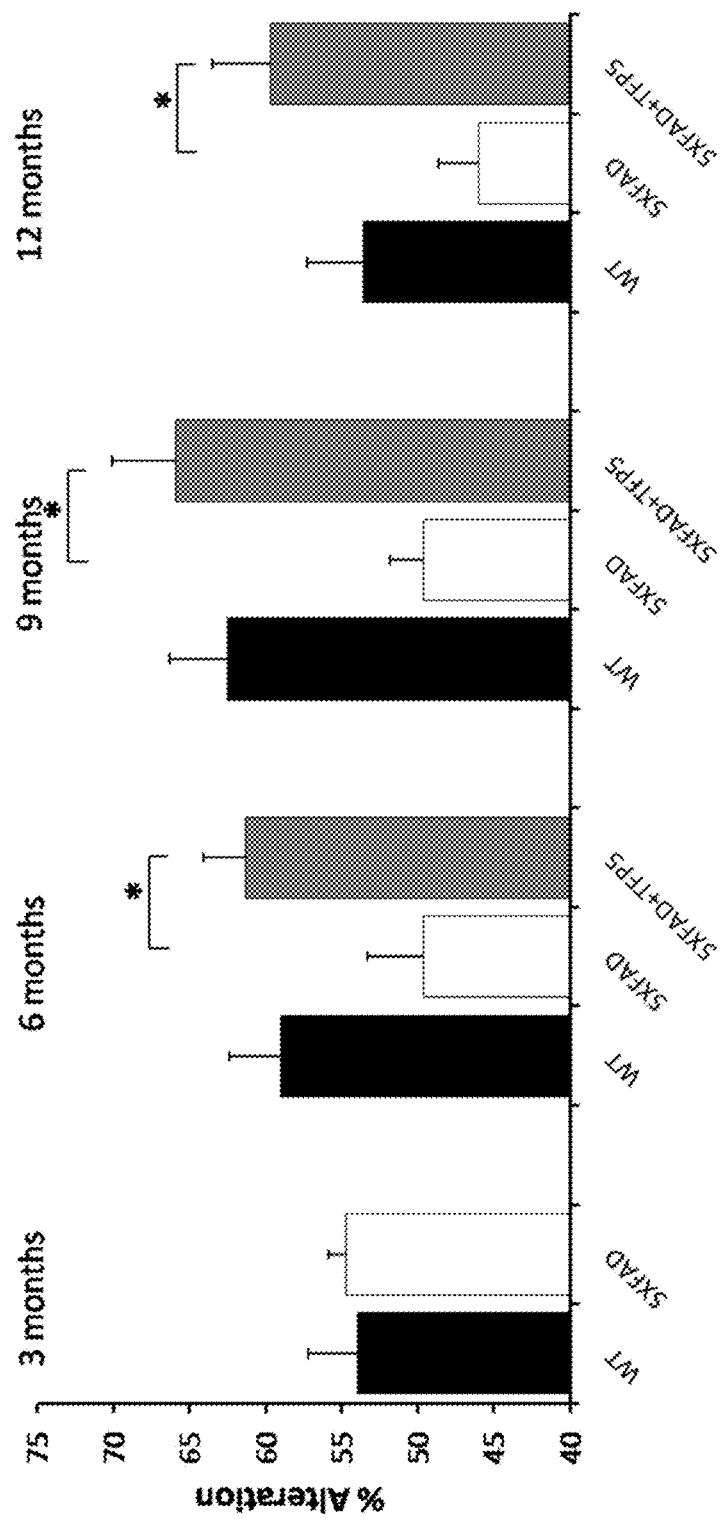
FIG. 20 is a bar graph demonstrating that TFP5 treated 5XFAD mice show rescue of memory deficits in the Y maze test. At 3, 6, 9 and 12 months old, animals received three consecutive ip injections (wild-type (WT) with vehicle, 5XFAD with vehicle and 5XFAD with 0.2 mM TFP5 peptide) were studied for spatial working memory by spontaneous alteration in the Y-maze. At 3 months, no behavioral difference between the WT and 5XFAD mice was noted. At 6, 9 and 12 months of age, WT mice showed normal alteration performance in the Y-maze, while 5XFAD performed poorly (less than 50%). However, 5XFAD mice injected with TFP5 recovered and showed normal alteration performance, compared to WT. Each data column represents the mean±SEM (n=4-12 and *p≤0.05).

At 3, 6, 9, and 12 months old, animals received three consecutive ip injections (of wild-type (WT) mice with vehicle, 5XFAD mice with vehicle, and 5XFAD mice with 0.2 mM TFP5 peptide) and were studied for spatial working memory by spontaneous alteration in the Y-maze. At 3 months, no behavioral difference between the WT and 5XFAD mice was noted. At 6, 9 and 12 months of age, WT mice showed normal alteration performance in the Y-maze, while 5XFAD performed poorly (less than 50%). However, 5XFAD mice injected with TFP5 recovered and showed normal alteration performance, compared to the WT mice (FIGS. 14 and 20). Each data column represents the mean±SEM (n=4-12 and *p≤0.05).

Example 14

TFP5 Rescues Memory Deficits in the Rota-Rod Test

This example demonstrates that TFP5 treated 5XFAD mice show rescue of memory deficits in the roto-rod test.

Figure 21:
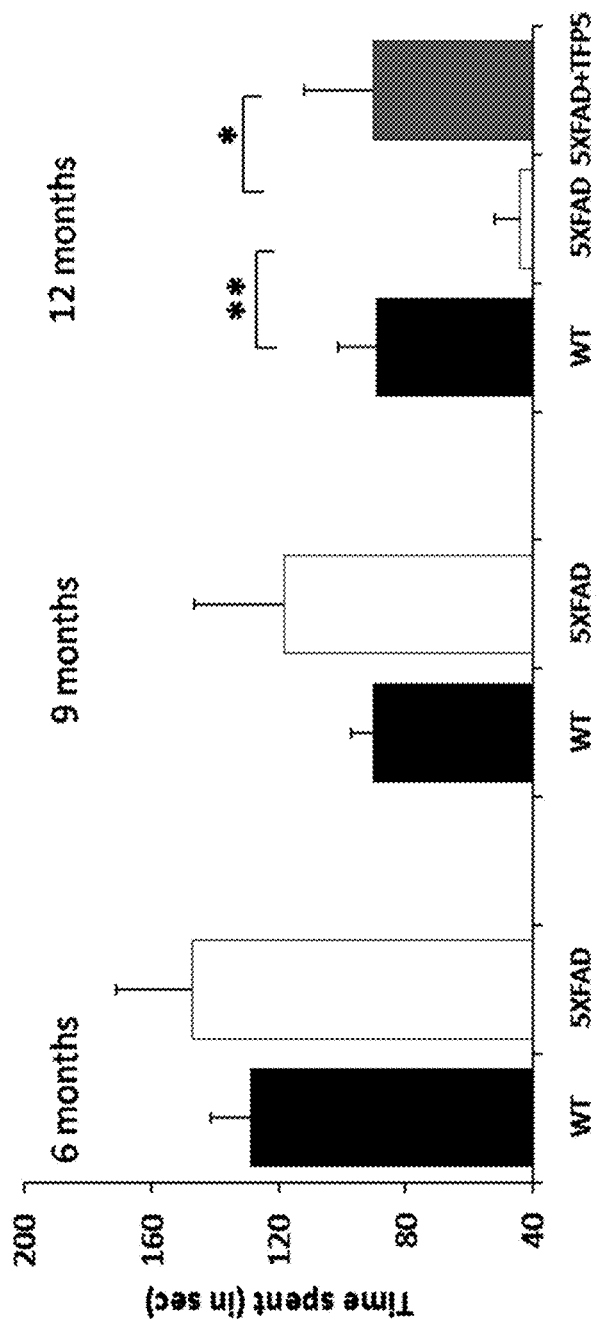
FIG. 21 is a bar graph illustrating that motor impairment of 5XFAD mice is rescued by TFP5 treatment (as measured by rota-rod analysis). Using rota-rod behavioral analysis to measure motor deficits at 6, 9, and 12 months of age, TFP5 and control animals (3 consecutive ip injections (WT with vehicle, 5XFAD with vehicle and 5XFAD with 0.2 mM TFP5 peptide) were assessed for motor behavior. No significant motor deficit was found in 5XFAD, compared with WT at 6 and 9 months but there was a significant deficit in 12 month old 5XFAD mice, compared with WT. At 12 months 5XFAD mice could not stay on the rotating rod. TFP5 treatment enhanced their performance equivalent to the WT. Each data column represents the mean±SEM. (n=4-12 and *p≤0.05, **p≤0.001).

Using a roto-rod behavioral for motor deficits at 6, 9, and 12 month TFP5 and control animals (3 consecutive ip injections of WT mice with vehicle, 5XFAD mice with vehicle and 5XFAD mice with 0.2 mM TFP5 peptide) were assessed for motor behavior. No significant motor deficit was found in 5XFAD compared with WT at 6 and 9 months but there was a significant deficit in 12 months old 5XFAD compared with WT. At 12 months 5XFAD mice could not stay on the rotating rod. TFP5 treatment enhanced their performance equivalent to the WT (FIG. 21). Each column in graph represents the mean±SEM. (n=4-12 and *p≤0.05, **p≤0.001).

Example 15

TFP5 Treatment Inhibits Hyperphosphorylation of Tau and Neurofilament Proteins

This example demonstrates that TFP5 treatment inhibits hyperphosphorylation of tau and neurofilament proteins (NFPs) in brains of 5XFAD mice.

Figure 22B:
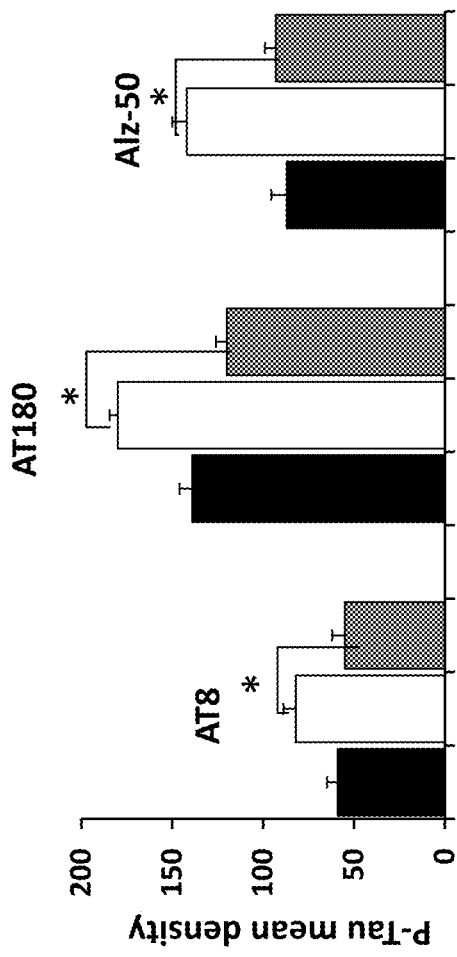
FIGS. 22A-22C illustrate TFP5 treatment inhibits hyperphosphorylation of tau and neurofilament proteins (NFPs) in brains of 5XFAD mice. Whole-brain homogenates were prepared from WT mice treated with vehicle and 5XFAD animals injected with TFP5 and vehicle. Immunoblot analysis using various phospho-tau and phospho-neurofilament (NF) protein M/H antibodies revealed a reduction of expression in the brain lysates of 5XFAD mice treated with TFP5 (FIG. 22A). AT8 recognizes phospho tau at pS202/pT205 and AT180 at pT231. SMI 31 antibody recognizes both phospho-NFH (upper band) and also phospho-tau (lower band). Equal loading was confirmed by actin staining. The density of each band was measured (FIGS. 22B and 22C). Data represent SEM± from four independent experiments.
Figure 22C:
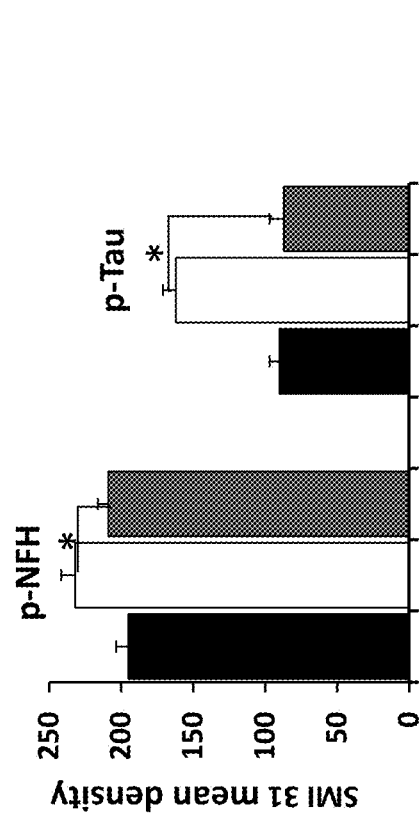
Figure 22A:
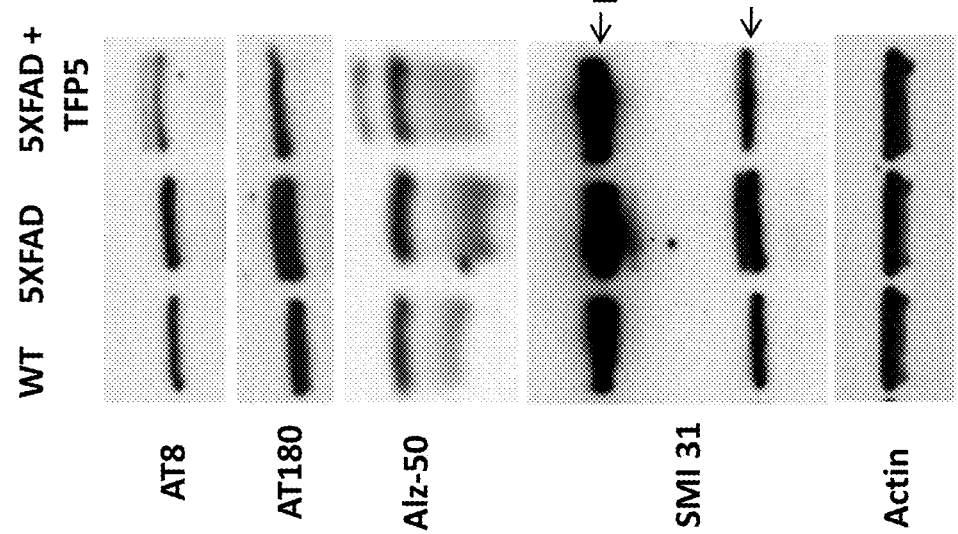

Whole-brain homogenates were prepared from WT mice treated with vehicle and 5XFAD animals injected with TFP5 and vehicle. Immunoblot analysis using various phospho-tau and phospho-NF-M/H antibodies revealed a reduction of expression in the brain lysates of 5XFAD mice treated with TFP5. AT8 recognizes phospho-tau at pS202/pT205 and AT180 at pT231. SMI 31 antibody recognizes both phospho-NFH (upper band) and also phospho-tau (lower band). Equal loading was confirmed by actin staining. The density of each band was measured (FIGS. 22B and 22C). Data represent SEM± from four independent experiments.

Figures 15A, 15B, 15C, 15D, 15E, 15F:
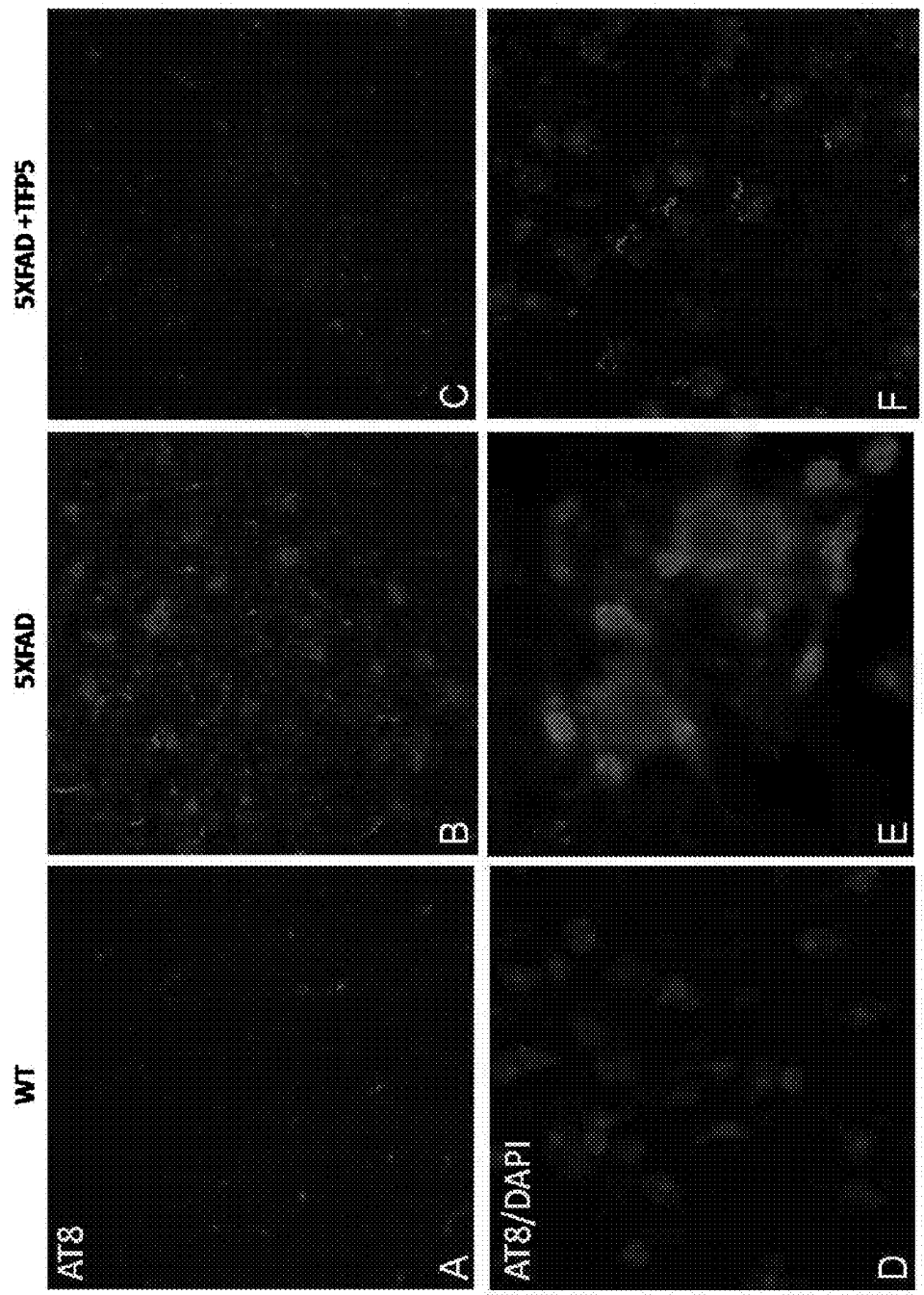
FIGS. 15A-F include a series of digital images illustrating that TFP5 reduces hyperphosphorylation of Tau (Ser2020) in the hippocampus of 5XFAD mice. AT8 antibody is used as a marker for Tau-phosphorylation in neurofibrillary tangle formation in AD. Therefore, AT8 phospho-Tau (Ser 202) antibody was used to study the phosphorylation of Tau in six month old 5XFAD mice. Confocal images for parasagittal brain sections showing part of the hippocampus of vehicle injected WT (FIG. 15A), 5XFAD (FIG. 15B) and TFP5 injected 5XFAD (FIG. 15C) mice stained with AT8 (FIGS. 15D, 15E and 15F) are the higher magnification (40×) images of (FIGS. 15A, 15B, and 15C at 20×) respectively shown along with nuclear staining DAPI.
Figures 16A, 16B, 16C, 16D, 16E, 16F:
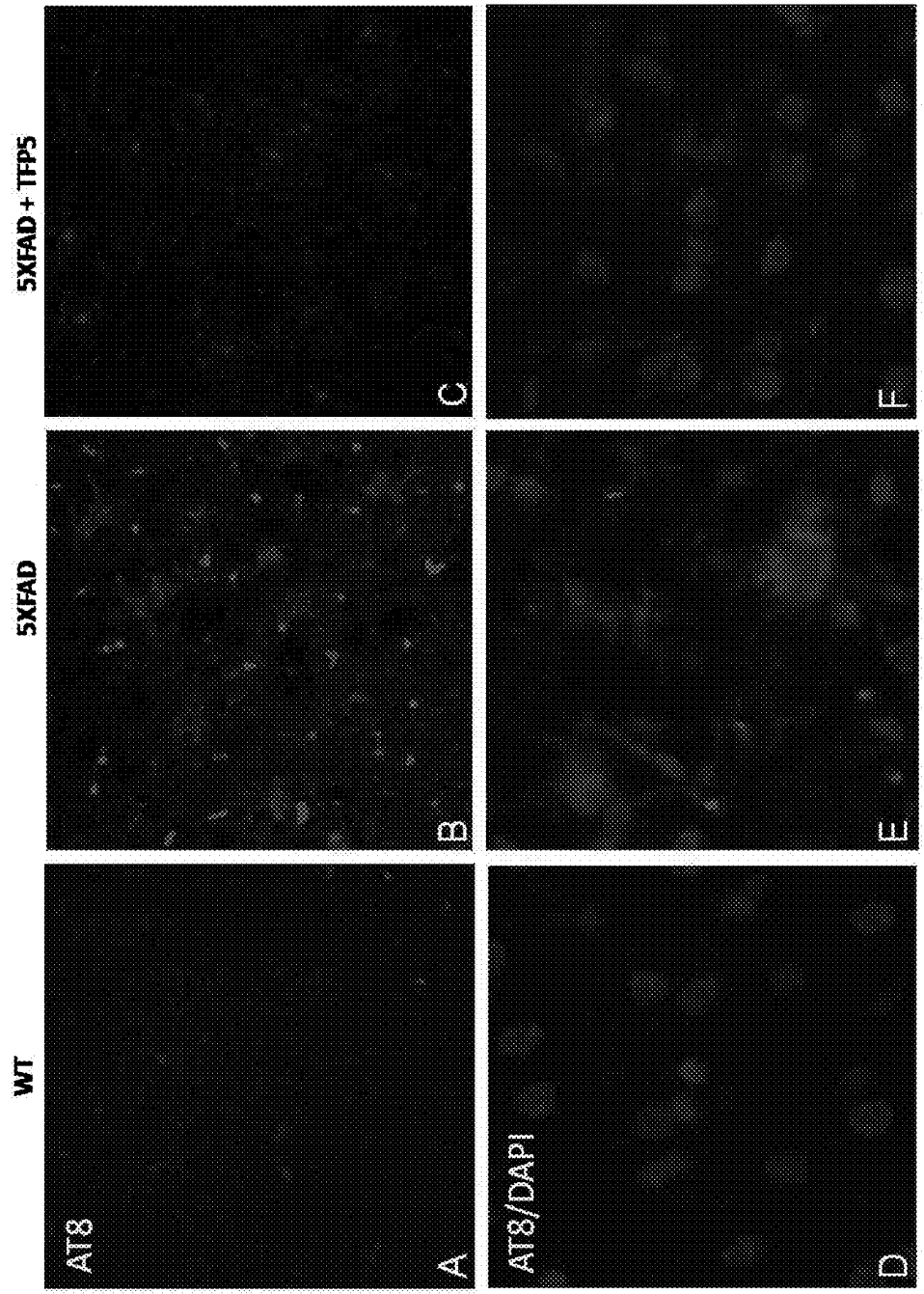
FIGS. 16A-F include a series of digital images illustrating TFP5 reduces hyperphosphorylation of Tau (Ser2020) in the cortex of 5XFAD mice. Confocal images for parasagittal brain sections showing part of the hippocampus of vehicle injected WT (FIG. 16A), 5XFAD (FIG. 16B) and TFP5 injected 5XFAD (FIG. 16C) mice stained with AT8 (FIGS. 16D, 16E and 16F) are the higher magnification (40×) images of (FIGS. 16A, 16B, and 16C at 20×) respectively shown along with nuclear staining DAPI.

In addition, TFP5 treatment was determined to reduce hyperphosphorylation of Tau (Ser2020) in the hippocampus (FIG. 15) and cortex (FIG. 16) of 5XFAD mice.

Example 16

TFP5 Treatment Inhibits Activation of Cells, Prevents Plaque Formation in Brain, and Reduces Neuronal Apoptosis This example demonstrates that TFP5 treatment inhibits and/or reduces the activation of astrocytes and microglia, reduces plaque formation, and reduces neuronal apoptosis in the brains of 5XFAD mice.

TFP5 and control animals (3, 6, 9, and 12 month old mice) were injected with a single ip injection containing vehicle or TFP3 for 3 consecutive days (WT mice with vehicle, 5XFAD mice with vehicle, and 5XFAD mice with 0.2 mM TFP5 peptide) and brain cortex sections were assessed four days after treatment by immunofluorescence using GFAP, OX42, Aβ42, and 6E10 antibodies.

Histology and Immunohistochemistry:

After performing behavior studies, the animals were perfused with PBS and one hemi-brain from each mouse was fixed in 4% paraformaldehyde/PBS and cryopreserved in 30% sucrose/PBS. Brains were sectioned sagittally on a freezing microtome at 10 microns. Serial sections were collected on a charged slide, blocked in 5% BSA and incubated overnight at 4° C. with the primary antibodies (Table 2). After washes, sections were prepared for immunofluorescence microscopy by incubating with goat anti-mouse or goat anti-rabbit secondary antibodies conjugated with either Alexa 488 or Alexa 594 (1:400 dilution), obtained from Molecular Probes, Carlsbad, Calif., USA. Sections were mounted with mounting medium containing DAPI (Vector Laboratories, Burlingame, Calif., USA) and coverslipped. In some cases, after primary antibody incubation, the sections were prepared for DAB as chromogen reaction product using ABC kit as per manufactures instructions (Vector Laboratories). The sections were counterstained with methylene green or haematoxylin, mounted, and coverslipped.

Imaging:

Fluorescent images were obtained with a Zeiss LSM-510 laser-scanning confocal microscope (Germany) and light microscopy was performed on a Nikon (Tokyo, Japan) E800 microscope with a Spot Advanced digital camera for capturing images. All images were processed and merged using Adobe Photoshop software.

TABLE 2

Antibodies used and their dilutions

| Antibody | Dilution | Company/Source |
|---|---|---|
| AT8 (Ser 202 and Thr 205) | 1:200 | Thermo Scientific |
| AT180 (Thr 231) | 1:500 | Thermo Scientific |
| Alz50 | 1:1000 | Dr. P. Davies |
| SMI-31 | 1:2000 | Covance |
| GFAP | 1:2000 | Santa Cruz |
| Cleaved caspase 3 | 1:1000 | Santa Cruz |
| 6E10 | 1:500 | Covance |
| Abeta42 | 1:500 | Covance |
| OX42 | 1:200 | Abcam |
| Cdk5 | 1:1000 | Santa Cruz |
| Total tau | 1:1000 | Santa Cruz |
| P35 | 1:1000 | Santa Cruz |

GFAP (Glial Fibrillary Acidic Protein) is used as a marker for activated astrocytes. It has been reported that 5XFAD mouse brain cortex has a very high number of activated astrocytes due to stress caused by the Aβ42 brain. Immunofluorescence of the mouse brain sections using an anti-GFAP antibody demonstrated that TFP5 treatment reduced the number of activated astrocytes in the brain of 5XFAD mice.

Activated microglia are identified by immunofluorescence using the OX42 antibody. In response to stress, microglia are activated and are increased in 5XFAD mouse brain cortex. These cells are reduced in number upon TFP5 treatment. Thus, TFP5 reduces the activation of microglia in the brain of 5XFAD mice.

Aβ42 causes the formation of plaques in AD. A significant reduction of Aβ42 is observed in 5XFAD mouse brain cortex after TFP5 injections. These results show that TFP5 reduces amyloid plaque formation in the brain of 5XFAD mice.

The specific Aβ42 antibody, 6E10, recognizes amino acid resides 1-16 of Aβ42. Significant reduction of Aβ42 is observed in the 5XFAD mouse brain cortex after three consecutive injections with TFP5. These results show that TFP5 treatment significantly reduced A-beta plaque formation in the brain of 5XFAD mice.

Cleaved caspase-3 (CC3) is a marker for apoptotic cells. After TFP3 injections, there was significant reduction in the number of apoptotic cells in brain sections from 5XFAD mice. These results show that TFP5 treatment reduces neuronal apoptosis in 5XFAD mouse brains.

Example 17

Treatment of Neurodegenerative Disease

This example describes a representative method that can be used to treat a neurodegenerative disease, such as AD, ALS, or PD, by administration of one or more agents that specifically inhibits the deregulated activity of Cdk5 responsible for neuronal pathology, thereby rescuing the cortical neuron abnormal phenotypes in vivo. Although particular methods, dosages, and modes of administrations are provided, one skilled in the art will appreciate that variations can be made without substantially affecting the treatment.

Based upon the teaching disclosed herein, a subject with a neurodegenerative disease can be treated by administering a therapeutically effective amount of a composition comprising an agent (such as TFP5) that inhibits the deregulated activity of Cdk5.

Screening Subjects

In some examples, the subject is first screened, usually using non-invasive methods (such as measuring motor skills or memory) to determine if the subject has symptoms characteristic of a neurodegenerative disease, such as AD, ALS, or PD. In other examples, the subject is screened by detecting a change in the level of Cdk5 activity.

Administration of Therapeutic Compositions

Following subject selection, a therapeutically effective dose of the composition including the agent is administered to the subject. For example, a therapeutically effective dose of an isolated peptide disclosed herein is administered to the subject to reduce or inhibit one or more symptoms associated with a neurodegenerative disease. Administration can be achieved by any method known in the art, and/or described herein, such as oral administration, inhalation, or inoculation (such as intramuscular, ip, or subcutaneous). In some examples, the agent is TFP5.

Assessment

Following the administration of one or more therapies, subjects having a neurodegenerative disease can be monitored for effective treatment, such as regression or reduction in one or more symptoms associated with a neurodegenerative disease, such as impaired motor skills or memory deficits. In particular examples, subjects are analyzed one or more times following treatment. Subjects can be monitored using any method known in the art.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated polypeptide, consisting of:
    a cyclin dependent kinase 5 (Cdk5) inhibitory domain, wherein the Cdk5 inhibitory domain consists of an amino acid sequence that has at least 95% sequence identity to the amino acid sequence set forth as SEQ ID NO: 1; and linked thereto,
    a protein transduction domain (PTD).

2. The isolated polypeptide of claim 1, wherein the Cdk5 inhibitory domain consists of the amino acid sequence set forth as SEQ ID NO: 1.

3. The isolated polypeptide of claim 1, wherein the PTD comprises a trans-activator of transcription (TAT) domain with at least 95% sequence identity to the amino acid sequence set forth as one of SEQ ID NO: 3, 4, 5, 6 or 7.

4. The isolated polypeptide of claim 3, wherein the TAT domain comprises the amino acid sequence set forth as one of SEQ ID NO: 3, 4, 5, 6 or 7.

5. The isolated polypeptide of claim 4, wherein the TAT domain consists of the amino acid sequence set forth as one of SEQ ID NO: 3, 4, 5, 6 or 7.

6. A pharmaceutical composition, comprising a therapeutically effective amount of the isolated polypeptide of claim 1 for preventing or reducing memory deficit associated with a neurodegenerative disease and a pharmaceutically acceptable carrier.

7. A method of reducing memory deficit associated with a neurodegenerative disease in a subject, comprising:
    administering to the subject with the neurodegenerative disease the pharmaceutical composition of claim 6 thereby preventing or reducing the memory deficit associated with the neurodegenerative disease in the subject.

8. The method of claim 7, wherein the neurodegenerative disease is Alzheimer's disease.

9. The isolated polypeptide of claim 3, wherein the PTD further comprises a three glycine linker.

10. The isolated polypeptide of claim 3, wherein the PTD further comprises a detectable label.

11. A composition comprising the isolated polypeptide of claim 1 and a carrier.

12. An isolated polypeptide, comprising an amino acid sequence with at least 95% sequence identity to the amino acid sequence set forth as SEQ ID NO: 2.

13. The isolated polypeptide of claim 12, wherein the isolated polypeptide comprises the amino acid sequence set forth as SEQ ID NO: 2.

14. The isolated polypeptide of claim 13, wherein the isolated polypeptide consists of the amino acid sequence set forth as SEQ ID NO: 2.

15. The isolated polypeptide of claim 12, further comprising a three glycine linker.

16. The isolated polypeptide of claim 12, further comprising a detectable label.

17. The isolated polypeptide of claim 15, further comprising fluorescein isothiocyanate.

18. The isolated polypeptide of claim 13, comprising the amino acid sequence set forth as SEQ ID NO: 17 linked to fluorescein isothiocyanate.

* * * * *

UNITED STATES PATENT AND TRADEMARK OFFICE
CERTIFICATE OF CORRECTION

PATENT NO. : 8,597,660 B2
APPLICATION NO. : 13/249003
DATED : December 3, 2013
INVENTOR(S) : Harish C. Pant et al.

Page 1 of 1

It is certified that error appears in the above-identified patent and that said Letters Patent is hereby corrected as shown below:

In the Claims:

Claim 7, column 58, line 33, "thereby preventing or reducing" should read --thereby reducing--.

Signed and Sealed this
Third Day of November, 2015

Michelle K. Lee
*Director of the United States Patent and Trademark Office*